US006864364B1

(12) United States Patent
Splawski et al.

(10) Patent No.: US 6,864,364 B1
(45) Date of Patent: Mar. 8, 2005

(54) MINK-RELATED GENES, FORMATION OF POTASSIUM CHANNELS AND ASSOCIATION WITH CARDIAC ARRHYTHMIA

(75) Inventors: Igor Splawski, Alston, MA (US); Mark T. Keating, Brookline, MA (US); Geoffrey W. Abbott, New Haven, CT (US); Federico Sesti, New Haven, CT (US); Steve A. N. Goldstein, Guilford, CT (US)

(73) Assignees: University of Utah Research Foundation, Salt Lake City, UT (US); Yale University, New Haven, CT (US)

( * ) Notice: Subject to any disclaimer, the term of this patent is extended or adjusted under 35 U.S.C. 154(b) by 0 days.

(21) Appl. No.: 09/550,163

(22) Filed: Apr. 14, 2000

Related U.S. Application Data

(60) Provisional application No. 60/129,404, filed on Apr. 15, 1999.

(51) Int. Cl.$^7$ .............................................. C07H 21/04
(52) U.S. Cl. .................. 536/23.5; 536/23.1; 435/320.1; 435/325; 435/468; 435/471; 435/252.3; 435/243; 435/254.11; 435/348; 435/349; 435/358; 435/410; 435/455
(58) Field of Search .............................. 536/23.1, 23.5, 536/24.33, 24.3, 24.31; 435/320.1, 243, 325, 252.3, 254.11, 455, 468, 471, 348, 349, 358, 410; 514/44; 424/93.2, 93.21

(56) References Cited

U.S. PATENT DOCUMENTS 5,620,892 A * 4/1997 Kurtz et al. ........... 435/354.21

FOREIGN PATENT DOCUMENTS

| WO | WO 01/14403 A1 | 3/2001 |
|---|---|---|
| WO | WO 01/27246 A1 | 4/2001 |
| WO | WO 01/57188 A2 | 8/2001 |

OTHER PUBLICATIONS

DNA—Basics of Structure and Analysis, 1998, pp. 1–6, http://www.ndsu.nodak.edu/instruct/mcclean/plsc731/dna/dna6.htm*
Murai T et al., Biochem Biophys Res Commun, 1989, May 30; 161 (1): pp. 176–181.*
Feder et al., U.S. patent 5,872,237, Sequence No. 20 & Abstract.*
Chiu et al., Optimizing energy potentials for sucess in protein tertiary structure prediction, 1998, Folding & Design, vol. 3, pp. 223–228.*
Wallace et al., Guide to molecular cloning, 1987, Methods in Enzymology, vol. 152, pp. 432–443.*
Sambrook et al, Molecular cloning: a laboratory manual, 1989, p. 11.47.*
Verma et al., Gene therapy–promises, problems and prospects, 1997, Nature, vol. 389, pp. 239–242.*
Anderson, Human gene therapy, 1998, Nature, vol. 392, pp. 25–30.*
Jorde et al., Medical Genetics, 1999, Mosby, p. 328.*
ACC # A1246239, Nov.. 4, 1998.*
ACC # A1339609, Dec., 29, 1998.*
Mountain, Gene therapy: the first decade, 2000, TIBTECH, vol. 18, pp. 119–128.*
G.W. Abbott et al., "A New Superfamily of Small Ion Channel Subunits," Biophysical Journal 76(1):A75, Jan. 1999. XP002930069.
R. Strausberg, "qi29g04.x1 Soares_NhHMPu_S1 Homo sapiens cDNA clone Image:1857942 3' similar to SW:MINK_human P15382 ISK slow voltage–gated potassium channel," Homo Sapiens, Database EMBL accession No. A1246239, Nov. 5, 1998. XP002206473.
R. Strausberg, "qq42a07.x1 Soares NhHMPu S1 Homo sapiens cDNA clone Image:1935156 3' similar to SW:Mink_human P15382 ISK slow voltage–gated potassium channel," Homo Sapiens, Database EMBL accession No. A1339609, Dec. 31, 1998. XP002206474.
R. Stausberg, "qq42e03.x1 NCI_CGAP GC6 Homo sapiens cDNA clone Image:2473948 3' similar to SW:MINK_human P15382 ISK slow voltage–gated potassium channel," Homo Sapiens, Database EMBL accession No. A1962650, Aug. 23, 1999, XP00206475.
M. Hattori et al., "Homo sapiens genomic DNA, chromosome 21q22.1, segment 23/28," Homo Sapiens, Database EMBL accession No. AP00052, May 13, 1998. XP002206476.
Y.T. Tang et al., "Human MiRP1 homologue, SEQ ID No. 2318," Homo Sapiens, Database EMBL accession No. ABB11948, Jan. 11, 2002, XP002207209.

(List continued on next page.)

*Primary Examiner*—Scott D. Priebe
*Assistant Examiner*—Brian Whiteman
(74) *Attorney, Agent, or Firm*—Rothwell Figg Ernst & Manbeck

(57) ABSTRACT

The present invention is directed to genes and gene products related to Min-K which form ion channels and to a process for diagnosis of ion channel disorders, including long QT syndrome (LQT). For example, KCNE2 forms $I_{Kr}$ potassium channels and is associated with LQT. LQT is diagnosed in accordance with the present invention by analyzing the DNA sequence of KCNE2 of an individual to be tested and comparing the respective DNA sequence to the known DNA sequence of a normal KCNE2 gene. Alternatively, these MinK-related genes of an individual to be tested can be screened for mutations which cause ion channel disorders, including LQT. Prediction of ion channel disorders, including LQT, will enable practitioners to prevent the disorders using existing medical therapy. This invention is further directed to the discovery that the HERG and KCNE2 (also known as MiRP1) proteins coassemble to form a cardiac $I_{Kr}$ potassium channel.

13 Claims, 12 Drawing Sheets

OTHER PUBLICATIONS

Y.T. Tang et al., "Human MiRP1 homologue–encoding cDNA, SEQ ID No. 968," Homo Sapiens, Datgabase EMBL accession No. ABA09192, Jan. 11, 2002. XP002207210.

Q. Wang et al., "Genetics, molecular mechanisms and management of long QT syndrome," Ann Med 30:58–65, 1998.

Abbott, G.W. et al. (1999). "a new superfamily of small ion channel subunits." *Biophysical J*. 76:A75 (Su–Pos257).

Abbott. G.W. et al. (1999). "MiRP1 forms $I_{Kr}$ potassium channels with HERG and is associated with cardiac arrhythmia." *Cell* 97:175–187.

Curran, M.E. et al. (1995). "A molecular basis for cardiac arrhythmia: HERG mutations cause long QT syndrome." *Cell* 80:795–803.

Goulding, E.H. et al. (1994). "Molecular mechanism of cyclic–nucleotide–gated channel activation." *Nature* 372:369–374.

McDonald, T.V. et al. (1997), "a minK–HERG complex regulates the cardiac potassium current$I_{kr}$," *Nature* 388:289–292.

* cited by examiner

```
         1               10                20                30                40                50                60
rMiRP1   MTTIANLTQTLEDAFKKVFITYMDSWRRNTTA-EQQALQARVDAENFYYVILYLMVMIGMFAFIVVAI
hMiRP1   MSTLSNFTQTLEDVFRRIFITYMDNWRQNTTA-EQEALQAKVDAENFYYVILYLMVMIGMFSFIIVAI
rMinK    -MALSNSTTVLP--FLASLWQETDEPGGNMSADLARRSQLRDDSK---LEALYILMVLGFFGFFTLGI
hMinK    -MILSNTTAVTP--FLTKLWQETVQQGGNMSG-LARRSPRSGDGK---LEALYVLMVLGFFGFFTLGI 70              80                90               100               110               120
rMiRP1   LVSTVKSKRREHSQDPYHQYIVED-WQQKYRS--QILHLEDSKAT-IHENLGATG--FTVSP------
hMiRP1   LVSTVKSKRREHSNDPYHQYIVED-WQEKYKS--QILNLEESKAT-IHENIGAAG--FKMSP------
rMinK    MLSYIRSKKLEHSHDPFNVYIESDAWQEKGKALFQARVLESFRACYVIENQAAVEQPATHLPELKPLS
hMinK    MLSYIRSKKLEHSNDPFNVYIESDAWQEKDKAYVQARVLESYRSCYVVENHLAIEQPNTHLPETKPSP
```

FIG. 1C

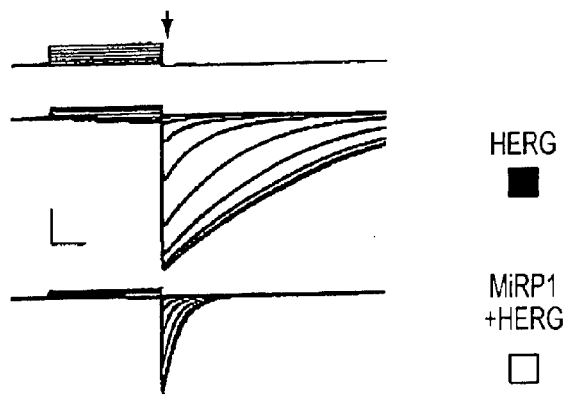
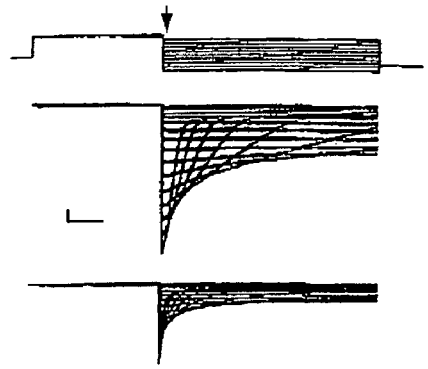
FIG. 2A
FIG. 2B
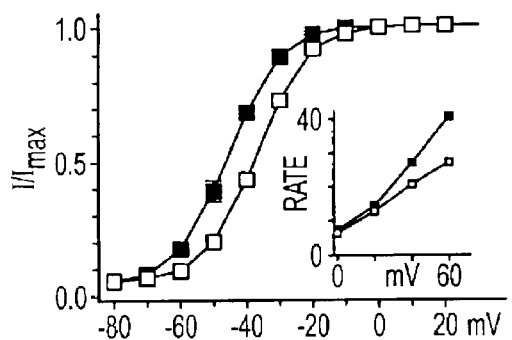
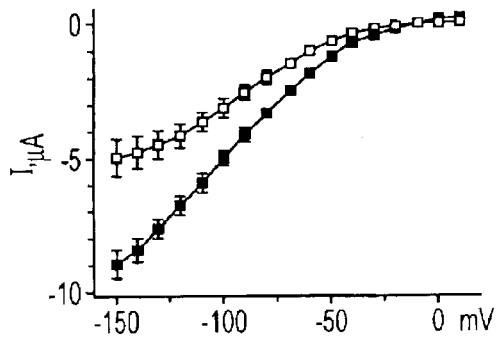
FIG. 2C
FIG. 2D
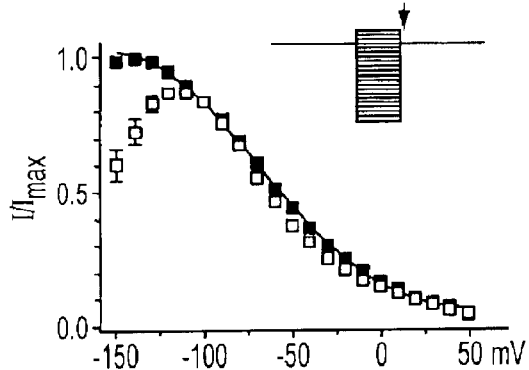
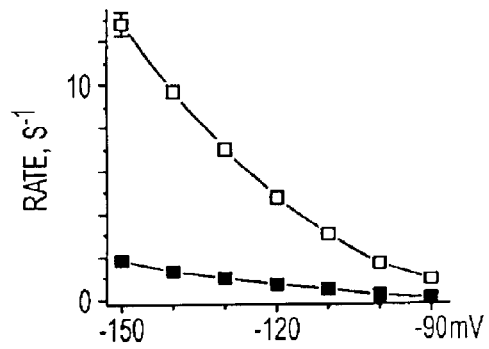
FIG. 2E
FIG. 2F

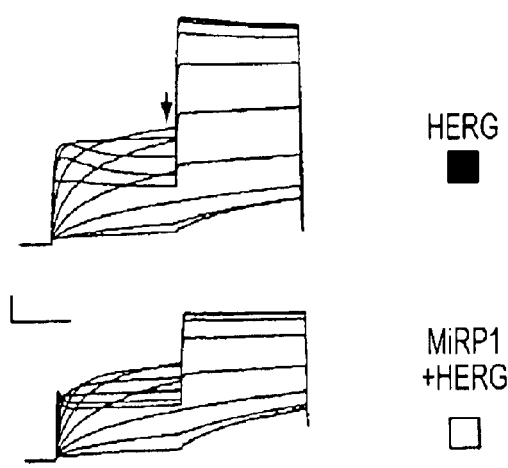
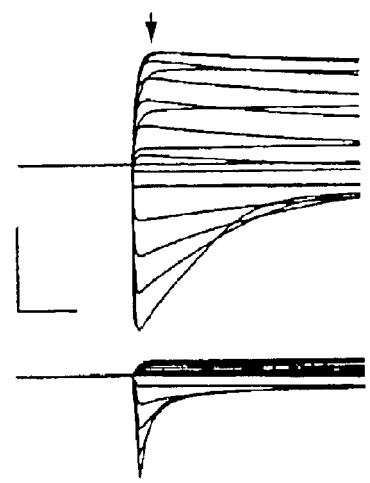
FIG. 5A
FIG. 5D
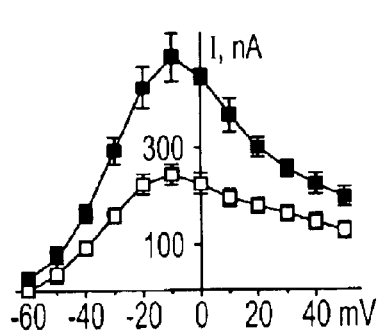
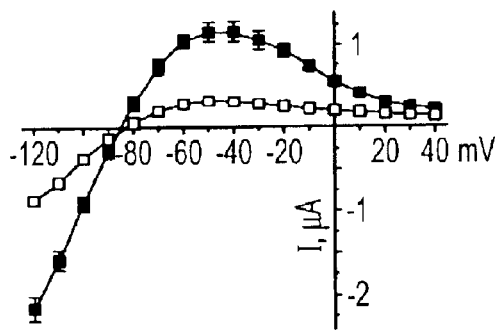
FIG. 5B
FIG. 5E
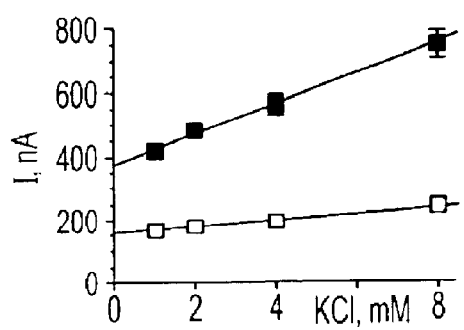
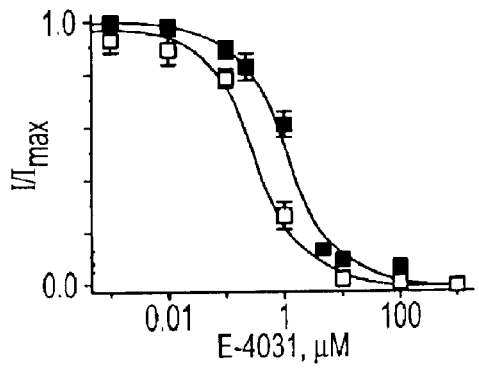
FIG. 5C
FIG. 5F

MINK-RELATED GENES, FORMATION OF POTASSIUM CHANNELS AND ASSOCIATION WITH CARDIAC ARRHYTHMIA

This application is related to U.S. provisional patent application Ser. No. 60/129,404, filed 15 Apr. 1999, incorporated herein by reference.

This application was made with Government support under Grant Nos. RO1 HL46401, RO1 GM51851 and P50-HL52338, funded by the National Institutes of Health, Bethesda, Md., and Grant No. M01 RR00064 from the U.S. Public Health Service. The federal government may have certain rights in this invention.

BACKGROUND OF THE INVENTION

The present invention is directed to genes and gene products related to Min-K which form ion channels and to a process for diagnosis of ion channel disorders, including long QT syndrome (LQT). For example, KCNE2 forms $I_{Kr}$ potassium channels in conjunction with HERG and is associated with LQT. LQT is diagnosed in accordance with the present invention by analyzing the DNA sequence of KCNE2 of an individual to be tested and comparing the respective DNA sequence to the known DNA sequence of a normal KCNE2 gene. Alternatively, these MinK-related genes of an individual to be tested can be screened for mutations which cause ion channel disorders, including LQT. Prediction of ion channel disorders, including LQT, will enable practitioners to prevent the disorders using existing medical therapy. This invention is further directed to the discovery that the HERG and KCNE2 (also known as MiRP1) proteins coassemble to form a cardiac $I_{Kr}$ potassium channel. This knowledge can be used to coexpress these two proteins in a cell, and such a transformed cell can be used for screening for drugs which will be useful in treating or preventing LQT. The invention is further directed to mutations in the human KCNE2 gene which have been discovered in families with LQT.

The publications and other materials used herein to illuminate the background of the invention or provide additional details respecting the practice, are incorporated by reference, and for convenience are respectively grouped in the appended List of References.

Cardiac arrhythmias are a common cause of morbidity and mortality, accounting for approximately 11% of all natural deaths (Kannel, 1987; Willich et al., 1987). In general, presymptomatic diagnosis and treatment of individuals with life-threatening ventricular tachyarrhythmias is poor, and in some cases medical management actually increases the risk of arrhythmia and death (Cardiac Arrhythmia Suppression Trial II Investigators, 1992). These factors make early detection of individuals at risk for cardiac arrhythmias and arrhythmia prevention high priorities.

Both genetic and acquired factors contribute to the risk of developing cardiac arrhythmias. Long QT syndrome (LQT) is an inherited cardiac arrhythmia that causes abrupt loss of consciousness, syncope, seizures and sudden death from ventricular tachyarrhythmias, specifically torsade de pointes and ventricular fibrillation (Ward, 1964; Romano, 1965; Schwartz et al., 1975; Moss et al., 1991). This disorder usually occurs in young, otherwise healthy individuals (Ward, 1964; Romano, 1965; Schwartz et al., 1975). Most LQT gene carriers manifest prolongation of the QT interval on electrocardiograms, a sign of abnormal cardiac repolarization (Vincent et al., 1992). The clinical features of LQT result from episodic cardiac arrhythmias, specifically repolarization-related ventricular tachyarrhythmias like torsade de pointes, named for the characteristic undulating nature of the electrocardiogram in this arrhythmia and ventricular fibrillation (Schwartz et al., 1975; Moss and McDonald, 1971). Torsade de pointes may degenerate into ventricular fibrillation, a particularly lethal arrhythmia. Although LQT is not a common diagnosis, ventricular arrhythmias are very common; more than 300,000 United States citizens die suddenly every year (Kannel, et al., 1987; Willich et al., 1987) and, in many cases, the underlying mechanism may be aberrant cardiac repolarization. LQT, therefore, provides a unique opportunity to study life-threatening cardiac arrhythmias at the molecular level.

Both inherited and acquired forms of LQT have been defined. Acquired LQT and secondary arrhythmias can result from cardiac ischemia, bradycardia and metabolic abnormalities such as low serum potassium or calcium concentration (Zipes, 1987). LQT can also result from treatment with certain medications, including antibiotics, antihistamines, general anesthetics, and, most commonly, antiarrhythmic medications (Zipes, 1987). Inherited forms of LQT can result from mutations in at least five different genes. In previous studies, LQT loci were mapped to chromosome 11p15.5 (KVLQT1 or LQT1) (Keating et al., 1991a; Keating et al., 1991b), 7q35-36 (HERG or LQT2), 3p21-24 (SCN5A or LQT3) (Jiang et al., 1994). Of these, the most common cause of inherited LQT is KVLQT1. Our data indicate that mutations in this gene are responsible for more than 50% of inherited LQT. Recently, a fourth LQT locus (LQT4) was mapped to 4q25-27 (Schott et al., 1995). Also, KCNE1 (LQT5) has been associated with long QT syndrome (Splawski et al., 1997b; Duggal et al., 1998). These genes encode ion channels involved in generation of the cardiac action potential. Mutations can lead to channel dysfunction and delayed myocellular repolarization. Because of regional heterogeneity of channel expression with the myocardium, the aberrant cardiac repolarization creates a substrate for arrhythmia. KVLQT1 and KCNE1 are also expressed in the inner ear (Neyroud et al., 1997; Vetter et al., 1996). We and others demonstrated that homozygous or compound heterozygous mutations in each of these genes can cause deafness and the severe cardiac phenotype of the Jervell and Lange-Nielsen syndrome (Neyroud et al., 1997; Splawski et al., 1997a; Schultze-Bahr et al., 1997; Tyson et al., 1997). Loss of functional channels in the ear apparently disrupts the production of endolymph, leading to deafness.

Presymptomatic diagnosis of LQT is currently based on prolongation of the QT interval on electrocardiograms. QTc (QT interval corrected for heart rate; Bazzett, 1920) greater than 0.44 second has traditionally classified an individual as affected. Most LQT patients, however, are young, otherwise healthy individuals, who do not have electrocardiograms. Moreover, genetic studies have shown that QTc is neither sensitive nor specific (Vincent et al., 1992). The spectrum of QTc intervals for gene carriers and non-carriers overlaps, leading to misclassifications. Non-carriers can have prolonged QTc intervals and be diagnosed as affected. Conversely, some LQT gene carriers have QTc intervals of <0.44 second but are still at increased risk for arrhythmia. Correct presymptomatic diagnosis is important for effective, gene-specific treatment of LQT.

Autosomal dominant and autosomal recessive forms of this disorder have been reported. Autosomal recessive LQT (also known as Jervell and Lange-Nielsen syndrome) has been associated with congenital neural deafness; this form of LQT is rare (Jervell and Lange-Nielsen, 1957). Autosomal dominant LQT (Romano-Ward syndrome) is more common, and is not associated with other phenotypic abnormalities (Romano et al., 1963; Ward, 1964). A disorder very similar to inherited LQT can also be acquired, usually as a result of pharmacologic therapy (Schwartz et al., 1975; Zipes, 1987).

The data have implications for the mechanism of arrhythmias in LQT. Two hypotheses for LQT have previously been proposed (Schwartz et al., 1994). One suggests that a predominance of left autonomic innervation causes abnormal cardiac repolarization and arrhythmias. This hypothesis is supported by the finding that arrhythmias can be induced in dogs by removal of the right stellate ganglion. In addition, anecdotal evidence suggests that some LQT patients are effectively treated by β-adrenergic blocking agents and by left stellate ganglionectomy (Schwartz et al., 1994). The second hypothesis for LQT-related arrhythmias suggests that mutations in cardiac-specific ion channel genes, or genes that modulate cardiac ion channels, cause delayed myocellular repolarization. Delayed myocellular repolarization could promote reactivation of L-type calcium channels, resulting in secondary depolarizations (January and Riddle, 1989). These secondary depolarizations are the likely cellular mechanism of torsade de pointes arrhythmias (Surawicz, 1989). This hypothesis is supported by the observation that pharmacologic block of potassium channels can induce QT prolongation and repolarization-related arrhythmias in humans and animal models (Antzelevitch and Sicouri, 1994). The discovery that one form of LQT results from mutations in a cardiac potassium channel gene supports the myocellular hypothesis.

In theory, mutations in a cardiac sodium channel gene could cause LQT. Voltage-gated sodium channels mediate rapid depolarization in ventricular myocytes, and also conduct a small current during the plateau phase of the action potential (Attwell et al., 1979). Subtle abnormalities of sodium channel function (e.g., delayed sodium channel inactivation or altered voltage-dependence of channel inactivation) could delay cardiac repolarization, leading to QT prolongation and arrhythmias. In 1992, Gellens and colleagues cloned and characterized a cardiac sodium channel gene, SCN5A (Gellens et al., 1992). The structure of this gene was similar to other, previously characterized sodium channels, encoding a large protein of 2016 amino acids. These channel proteins contain four homologous domains (DI–DIV), each of which contains six putative membrane spanning segments (S1–S6). SCN5A was recently mapped to chromosome 3p21, making it an excellent candidate gene for LQT3 (George et al., 1995), and this gene was then proved to be associated with LQT3 (Wang et al., 1995a).

In 1994, Warmke and Ganetzky identified a novel human cDNA, human ether a-go-go related gene (HERG, Warmke and Ganetzky, 1994). HERG was localized to human chromosome 7 by PCR analysis of a somatic cell hybrid panel (Warmke and Ganetzky, 1994) making it a candidate for LQT2. It has predicted amino acid sequence homology to potassium channels. HERG was isolated from a hippocampal cDNA library by homology to the Drosophila ether a-go-go gene (eag), which encodes a calcium-modulated potassium channel (Bruggemann et al., 1993). HERG is not the human homolog of eag, however, sharing only ~50% amino acid sequence homology. HERG has been shown to be associated with LQT2 (Curran et al., 1995).

LQT1 was found to be linked with the gene KVLQT1 (Q. Wang et al., 1996). Sixteen families with mutations in KVLQT1 were identified and characterized and it was shown that in all sixteen families there was complete linkage between LQT1 and KVLQT1. KVLQT1 was mapped to chromosome 11p15.5 making it a candidate gene for LQT1. KVLQT1 encodes a protein with structural characteristics of potassium channels, and expression of the gene as measured by Northern blot analysis demonstrated that KVLQT1 is most strongly expressed in the heart. One intragenic deletion and ten different missense mutations which cause LQT were identified in KVLQT1. These data define KVLQT1 as a novel cardiac potassium channel gene and show that mutations in this gene cause susceptibility to ventricular tachyarrhythmias and sudden death.

It was known that one component of the $I_{Ks}$ channel is minK, a 130 amino acid protein with a single putative transmembrane domain (Takumi et al., 1988; Goldstein and Miller, 1991; Hausdorff et al., 1991; Takumi et al., 1991; Busch et al., 1992; Wang and Goldstein, 1995; KW Wang et al., 1996). The size and structure of this protein made it unlikely that minK alone forms functional channels (Attali et al., 1993; Lesage et al., 1993). Evidence was presented that KVLQT1 and minK coassemble to form the cardiac $I_{Ks}$ potassium channel (Sanguinetti et al., 1996b). $I_{Ks}$ dysfunction is a cause of cardiac arrhythmia. It was later shown that mutations in KCNE1 (which encodes minK) also can result in LQT (Splawski et al., 1997b).

It is desired to identify other genes which are involved with LQT and which can be used for the diagnosis of LQT.

SUMMARY OF THE INVENTION

The present invention is directed to MinK-related genes, their protein products, their association to form ion channels, such as potassium channels, and their association with ion channel disorders, such as cardiac arrhythmia.

In one aspect of the present invention, the DNA and protein sequences are provided for human KCNE2, rat KCNE2, human KCNE3, mouse KCNE3, human KCNE4 and mouse KCNE4. These genes are alternatively referred to as MiRP1, MiRP2 and MiRP3, respectively.

In a second aspect of the present invention, the coassembly of HERG and KCNE2 to form an $I_{Kr}$ potassium channel is provided.

In a third aspect of the present invention, the association of KCNE2 with cardiac arrhythmia is provided. The knowledge that these two proteins coassemble to form the $I_{Kr}$ channel is useful for developing an assay to screen for drugs which are useful in treating or preventing LQT. By coexpressing both genes in a cell such as an oocyte it is possible to screen for drugs which have an effect on the $I_{Kr}$ channel, both in its wild-type and in its mutated forms. This knowledge is also useful for the analysis of the KCNE2 gene for an early diagnosis of subjects with LQT.

In a fourth aspect of the present invention, mutations in KCNE2 which are associated with LQT are provided.

In a fifth aspect of the present invention, analysis of the KCNE2 gene is provided for an early diagnosis of subjects with LQT. The diagnostic method comprises analyzing the DNA sequence of the KCNE2 gene of an individual to be tested and comparing it with the DNA sequence of the native, non-variant gene. In a second embodiment, the KCNE1 gene of an individual to be tested is screened for mutations which cause LQT. The ability to predict LQT will enable physicians to prevent the disease with medical therapy such as beta blocking agents.

In a sixth aspect of the present invention, drug candidates are screened to identify drugs that are useful for treating or preventing LQT.

In a seventh aspect of the present invention, drugs useful for treating LQT and other related or unrelated disorders are screened for their risk of causing LQT or such disorders because they may interact and block an ion channel.

In an eighth aspect of the present invention, pharmacogenomics of the genotype and drug reactions are provided.

BRIEF DESCRIPTION OF THE FIGURES

FIGS. 1A–1C show that MiRP1 is expressed in the heart and related to MinK. FIG. 1A: Rat MiRP1 tissue distribution. Northern blot of indicated rat tissues performed with an rKCNE1fragment (acc. no. D85797, 387 bp); 2 μg poly(A)$^+$ mRNA per tissue per lane. FIG. 1B: The blot in panel a probed for β-actin. FIG. 1C: Predicted peptide sequences for rat and human MiRP1 SEQ ID NO: 4 and SEQ ID NO: 2, respectively, and MinK SEQ ID NO: 21 and SEQ ID NO: 22, respectively. The putative transmembrane segment is underlined; identical residues are lightly shaded; three hMiRP1 positions associated with arrhythmia are darkly shaded (Q9, M54, I57). MiRP1 contains consensus sequences for 2 N-linked glycosylation sites (N6, N29) and 2 protein kinase C-mediated phosphorylation sites (T71, S74). Rat and human KCNE1 cDNAs contain in-frame termination codons without intervening ATGs in their 5' upstream sequences and an A in the position −3 relative to the predicted initiator methionine; accession numbers for human and rat KCNE1 are AF071002 and AF071003, respectively.

FIGS. 2A–2F show that rMiRP1 is an ion channel subunit. Attributes of channels formed with HERG (■) or rMiRP1 and HERG (□) subunits were assessed in 0.3 mM Ca$^{2+}$, 100 mM KCl solution by the indicated protocols, as described in the Examples. FIG. 2A: Raw current traces by protocol 1 (inset); scale bars 1 μA and 1 s. FIG. 2B: Raw current traces by protocol 3 (inset), otherwise as in FIG. 2A. FIG. 2C: Steady-state activation by protocol 1; tail currents measured at arrow, mean±s.e.m. for groups of 10 oocytes, normalized to I$_{Max}$ (40 mV). Lines according to the Boltzmann function: $1/\{1+\exp[(V_{1/2}-V)/V_s]\}$ where $V_{1/2}$ is half maximal voltage and $V_s$ the slope factor; error bars represent s.e.m. $V_{1/2}$ was −46±1 and −37±1 mV and $V_s$ 11.4±0.2 and 11.7±0.1 for HERG and rMiRP1+HERG channels, respectively. (2C, inset) Activation rates at various voltages by protocol 2, groups of 3 oocytes, normalized to the rate at 60 mV. FIG. 2D: Peak tail currents by protocol 3; fit as in FIG. 2C; mean±s.e.m. for groups of 10 oocytes; peak at −150 mV for HERG and rMiRP1+HERG channels was −8.8±0.5 and −4.9±0.7 μA, respectively. FIG. 2E: Steady-state inactivation by protocol 4 (inset); mean±s.e.m. for groups of 8 oocytes, normalized to peak (−140 mV). FIG. 2F: Deactivation rates at various voltages by protocol 3; current relaxation was fit with a single exponential (I=Ae$^{-t/\tau}$) with groups of 8 oocytes; for HERG and rMiRP1+HERG channels at −120 mV, τ$^{-1}$ was 1.5±0.2 and 0.21±0.01 s, and A was 7.9±0.4, and 4.2±0.5 μA, respectively.

FIG. 3A: Single channel currents at various voltages; scale bars 0.5 pA and 0.2 s. FIG. 3B: All points histograms computed at −90 mV from the patches in panel a with roughly 30,000 events (150 transitions) recorded prior to deactivation and does not reflect P$_o$. FIG. 3C: Current-voltage relationships for single HERG or rMiRP1+HERG channels in cell-attached patches (n=5) held at the indicated voltages; all points histograms were constructed with 1.3×10$^5$ events at each voltage, ~400 transitions. Slope conductances were 12.9±2.0 and 8.2±1.4 pS, for HERG and rMiRP1+HERG channels, respectively. Filtered at 0.5 kHz.

FIG. 4A: Deactivation of single channels in cell-attached patches as in FIG. 3; scale bars 2 pA and 0.75 s. FIG. 4B: Ensemble of 50–70 trials performed as in panel a at −100 mV; capacitance transients were neutralized by null trace subtraction. Histograms were fit with a single exponential function (I=I$_o$+Ie$^{-t/\tau}$); τ$^{-1}$=300 ms, I$_o$=−8 pA and I=−20 pA for HERG channels; τ$^{-1}$=131 ms, I$_o$=−10 pA and I=−24 pA for channels containing rMiRP1 and HERG subunits. Scale bars 10 pA and 0.5 s.

FIGS. 5A–5F show that rMiRP1/HERG channels (□) but not HERG channels (■) are similar to native I$_{Kr}$ channels in their regulation by K$^+$ and deactivation rate. Performed in 1 mM Ca$^{2+}$, 4 mM KCl solution by protocols as described in the Examples. FIG. 5A: Raw current traces by protocol 6; scale bars 0.1 μA, 1 s. FIG. 5B: Current-voltage relationship at end of the activating pulse (arrow); mean±s.e.m. for groups of 7 oocytes; studied as in FIG. 5A. FIG. 5C: Variation of current amplitude with external KCl; mean±s.e.m. for groups of 8 cells studied as in panel a at 0 mV. Solid lines are linear fits to the data; for HERG, the relation gives a slope=46±2 and intercept=377±6 nA (R=0.998); for rMiRP1/HERG, slope=11.7±0.4 and intercept 155±2 nA (R=0.999). FIG. 5D: Raw current traces by protocol 3; 1 s pre-pulse and test pulse durations; scale bars 1 pA and 250 ms. FIG. 5E: Current-voltage relationship at peak (arrow in FIG. 5D); mean±s.e.m. for groups of 5 oocytes; at −50 mV currents were 1200±100 and 300±60 nA while at −120 mV they were −2200±100 and −900±70 for HERG and rMiRP1/HERG channels, respectively. FIG. 5F: Steady-state block by various concentrations of E-4031 in 20 KCl solution assessed by protocol 5 and plotted as the fraction of unblocked current for groups of 6 oocytes; inhibition constants are reported in the text. Neither channel type showed block with the initial pulse.

FIG. 6A: Expression in COS cells of rMiRP1-HA (M1), HERG-cmyc (H) and connexin43-cmyc (C). Lanes contain total cell lysate (TL) or immunoprecipitations (IP) performed with anti-cmyc antibody. SDS-PAGE (10–16%) and western blot visualization with anti-HA antibody. Cells were transfected with subunits as follows: lanes 1,2: M1+H; lane 3: H; lane 4: M1; lane 5: M1+C; bars mark 32.7, 30.2 and 24 kDa. FIG. 6B: rMiRP1 forms complexes with HERG in preference to MinK in vitro. Lanes contain immunoprecipitates using anti-cmyc antibody of $^{35}$S-methionine labeled translation products generated with rabbit reticulocyte lysate and were visualized by autoradiography. Reaction mixtures contained subunits, rMiRP1 (M1), rMinK (m) and HERG-cmyc (H), as follows: lane 1: M1+H; lane2: m+H; lane3: M1+m+H; bars 30.2 and 24 kDa.

FIG. 7A: The first 20 current traces for a cell expressing HERG channels; fraction of unblocked current in the first pulse for this cell was=0.99. FIG. 7B: The first 20 current traces for a cell expressing hMiRP1/HERG channels; fraction of unblocked current in the first pulse for this cell was=0.64. FIG. 7C: Relaxation to equilibrium blockade for the cells in panel a (HERG channels, ■, τ=38 cycles) and panel b (hMiRP1/HERG channels, □, τ=4 cycles).

FIG. 8A: Raw current traces with wild type (WT), T8A, Q9E or M54T-hMiRP1 and HERG in CHO cells by protocol 6 with 1 mM $Ca^{2+}$, 4 mM KCl solution (Examples); scale bars represent 15 pA for WT, and 50 pA for T8A, Q9E and M54T-hMiRP1 and 0.5 s. FIG. 8B: Tail currents elicited by depolarizing to 20 mV (not shown) and repolarizing to voltages from −20 to −120 mV, otherwise as in FIG. 8A; scale bars represent 50 pA for WT, 100 pA for T8A and M54T, 500 pA for Q9E-hMiRP1 and 0.1 s. FIG. 8C: Activation: isochronal Po curves for WT (□), T8A (△), Q9E (●) and M54T-hMiRP1 (▲); curves are mean±s.e.m. for groups of 10–14 cells and are fit as in FIG. 2C; half-maximal activation voltage and slope factors are reported in Table 1. FIG. 8D: Deactivation: fast component, for WT (□), T8A (△), Q9E (●) and M54T-hMiRP1 (▲); values for fast and slow rates and their weights were estimated by fitting raw current traces to a double exponential function (Table 1).

FIG. 9A: Raw current traces of Q9E-hMiRP1 expressed with HERG in CHO cells by protocol 6; scale bars 0.1 pA and 0.1 s. FIG. 9B: Variation of peak tail current amplitude at equilibrium with varying doses of clarithromycin after activation at +20 mV; half-maximal blocking concentrations are in the text, Hill coefficients were 1.7±0.2 and 1.7±0.1 for WT (□) and Q9E-hMiRP1 (○), respectively. FIG. 9C: Current-voltage relationship as in panel a, mean±s.e.m. for groups of 6 cells in the absence (●) or presence (○) of 0.5 mM clarithromycin. Data were fitted using the Boltzman equation in FIG. 2C and multiplied by the reciprocal of the fraction of unblocked current; with 0.5 mM clarithromycin the $V_{1/2}$ for wild type was −30±8 mV (not shown) while it was −25±5 mV for Q9E-hMiRP1 (shown); slope factors were unchanged. In 1 mM $Ca^{2+}$, 1 mM KCl solution and 0.5 mM clarithromycin (not shown), the $V_{1/2}$ for wild type was −32±6 mV and for Q9E-hMiRP1 was −29±10 mV; slope factors were again unchanged.

SUMMARY OF THE SEQUENCE LISTING

Figure 1A:
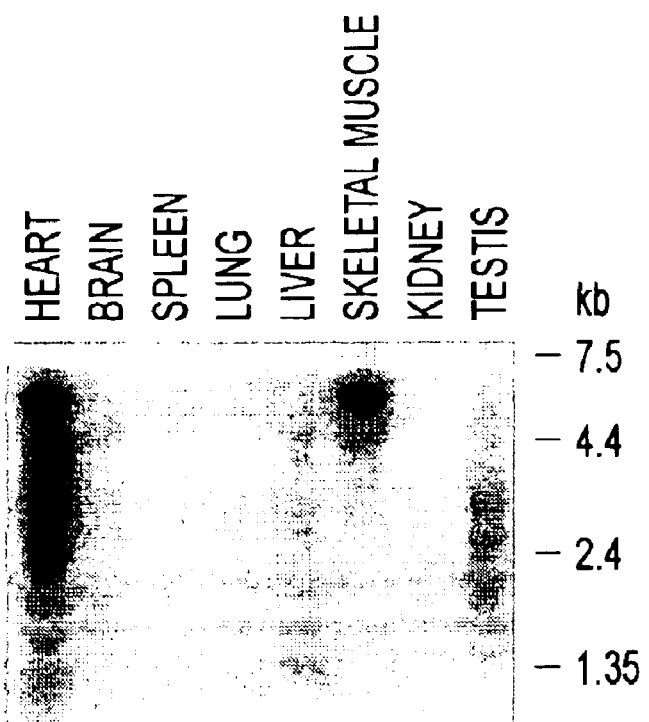
Figure 1B:
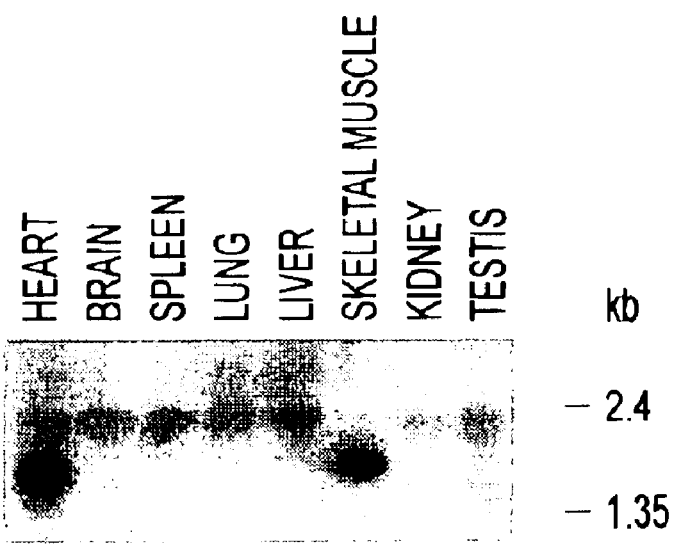

SEQ ID NO:1 is the DNA sequence for human KCNE2. SEQ ID NO:2 is the protein sequence for human KCNE2. SEQ ID NO:3 is the DNA sequence for rat KCNE2. SEQ ID NO:4 is the protein sequence for rat KCNE2. SEQ ID NO:5 is the DNA sequence for human KCNE3. SEQ ID NO:6 is the protein sequence for human KCNE3. SEQ ID NO:7 is the DNA sequence for mouse KCNE3. SEQ ID NO:8 is the protein sequence for mouse KCNE3. SEQ ID NO:9 is the DNA sequence for human KCNE4. SEQ ID NO:10 is the protein sequence for human KCNE4. SEQ ID NO:11 is the DNA sequence for mouse KCNE4. SEQ ID NO:12 is the protein sequence for mouse KCNE4. SEQ ID Nos:13–18 are the DNA sequences for amplification primers for mutation screening. SEQ ID NO:19 is the amino acid sequence for HA residues used for epitope-tagging. SEQ ID NO:20 is the amino acid sequence for cmyc residues used for epitope-tagging. SEQ ID NO:21 is the amino acid sequence for rat MinK. SEQ ID NO:22 is the amino acid sequence for human MinK.

DETAILED DESCRIPTION OF THE INVENTION

The present invention is directed to the determination of the sequence of several MinK-related genes as herein described, their association to form ionic channels, such as potassium channels, and their association with ion channel disorders, such as cardiac arrhythmia. The present invention is also directed to molecular variants of the MinK-related genes, particularly KCNE2 which cause or are involved in the pathogenesis of LQT. Alternatively, these MinK-related genes of an individual to be tested can be screened for mutations which cause ion channel disorders, including LQT. Prediction of ion channel disorders, including LQT, will enable practitioners to prevent the disorders using existing medical therapy. It is also directed to the determination that HERG and MiRP1 (KCNE2) coassemble to form cardiac $I_{Kr}$ potassium channels.

More specifically, the present invention relates to mutations in the KCNE2 gene and their use in the diagnosis of LQT. The present invention is further directed to methods of screening humans for the presence of KCNE2 gene variants which cause LQT. Since LQT can now be detected earlier (i.e., before symptoms appear) and more definitively, better treatment options will be available in those individuals identified as having LQT. The present invention is also directed to methods for screening for drugs useful in treating or preventing LQT1. The present invention is further directed to methods for screening drugs for adverse effects on ion channels. Finally, the present invention is directed to correlating a genotype with a drug interaction, i.e., pharmacogenomics.

The present invention provides methods of screening the MinK-related genes, e.g., the KCNE2 gene to identify mutations. Such methods may further comprise the step of amplifying a portion of the MinK-related genes, e.g., the KCNE2 gene, and may further include a step of providing a set of polynucleotides which are primers for amplification of said portion of the KCNE2 gene. The method is useful for identifying mutations for use in either diagnosis or prognosis of ion channel disorders, such as LQT which is associated with KCNE2.

The present invention further demonstrates that KCNE2 (encoding KCNE2) is also involved in LQT. The KCNE2 protein and HERG coassemble to form a $K^+$ channel. The present invention thus provides methods of screening the KCNE2 gene to identify mutations. Such methods may further comprise the step of amplifying a portion of the KCNE2 gene, and may further include a step of providing a set of polynucleotides which are primers for amplification of said portion of the KCNE2 gene. The method is useful for identifying mutations for use in either diagnosis of LQT or prognosis of LQT.

The present invention is also directed to a method for screening drug candidates to identify drugs useful for treating or preventing ion channel disorders, such as LQT. LQT drug screening is performed by coexpressing mutant HERG and/or KCNE2 genes in cells, such as oocytes, mammalian cells or transgenic animals (e.g., knockout mice), and assaying the effect of a drug candidate on the $I_{Kr}$ channel. The effect is compared to the $I_{Kr}$ channel activity of the wild-type HERG and KCNE2 genes.

The present invention is further directed to a method for screening drugs used or contemplated for use in treating or preventing LQT or other cardiovascular disorders or non-cardiovascular disorders for adverse effects on ion channels, such as the $I_{Kr}$ channel. Drug screening is performed by coexpressing HERG and/or KCNE2 genes in cells, such as oocytes or mammalian cells and assaying the effect of a drug on the $I_{Kr}$ channel. The effect is compared to the $I_{Kr}$ channel activity in the absence of the drug.

The invention is finally directed to a method for determining the effect of a genotype to a reaction with a drug. For example, the method is able to correlate the presence of a particular allele with an improved or adverse reaction to a drug used to treat or prevent an ion channel disorder, such as LQT.

Proof that the KCNE2 gene is involved in causing LQT is obtained by finding sequences in DNA extracted from affected kindred members which create abnormal KCNE2 gene products or abnormal levels of the gene products. Such LQT susceptibility alleles will co-segregate with the disease in kindreds. They will also be present at a much higher frequency in non-kindred individuals with LQT than in individuals in the general population. The key is to find mutations which are serious enough to cause obvious disruption to the normal function of the gene product. These mutations can take a number of forms. The most severe forms would be frame shift mutations or large deletions which would cause the gene to code for an abnormal protein or one which would significantly alter protein expression. Less severe disruptive mutations would include small in-frame deletions and nonconservative base pair substitutions which would have a significant effect on the protein produced, such as changes to or from a cysteine residue, from a basic to an acidic amino acid or vice versa, from a hydrophobic to hydrophilic amino acid or vice versa, or other mutations which would affect secondary or tertiary protein structure. Silent mutations or those resulting in conservative amino acid substitutions would not generally be expected to disrupt protein function.

According to the diagnostic and prognostic method of the present invention, alteration of the wild-type KCNE2 gene is detected. In addition, the method can be performed by detecting the wild-type KCNE2 gene and confirming the lack of a cause of LQT as a result of this locus. "Alteration of a wild-type gene" encompasses all forms of mutations including deletions, insertions and point mutations in the coding and noncoding regions. Deletions may be of the entire gene or of only a portion of the gene. Point mutations may result in stop codons, frameshift mutations or amino acid substitutions. Somatic mutations are those which occur only in certain tissues and are not inherited in the germline. Germline mutations can be found in any of a body's tissues and are inherited. Point mutational events may occur in regulatory regions, such as in the promoter of the gene, leading to loss or diminution of expression of the mRNA. Point mutations may also abolish proper RNA processing, leading to loss of expression of the KCNE2 gene product, or to a decrease in mRNA stability or translation efficiency.

Useful diagnostic techniques include, but are not limited to fluorescent in situ hybridization (FISH), direct DNA sequencing, PFGE analysis, Southern blot analysis, single stranded conformation analysis (SSCA), RNase protection assay, allele-specific oligonucleotide (ASO), dot blot analysis and PCR-SSCP, as discussed in detail further below. Also useful is the recently developed technique of DNA microchip technology.

The presence of LQT may be ascertained by testing any tissue of a human for mutations of KCNE2 gene. For example, a person who has inherited a germline KCNE2 mutation would be prone to develop LQT. This can be determined by testing DNA from any tissue of the person's body. Most simply, blood can be drawn and DNA extracted from the cells of the blood. In addition, prenatal diagnosis can be accomplished by testing fetal cells, placental cells or amniotic cells for mutations of the KCNE2 gene. Alteration of a wild-type KCNE2 allele, whether, for example, by point mutation or deletion, can be detected by any of the means discussed herein.

There are several methods that can be used to detect DNA sequence variation. Direct DNA sequencing, either manual sequencing or automated fluorescent sequencing can detect sequence variation. Another approach is the single-stranded conformation polymorphism assay (SSCP) (Orita et al., 1989). This method does not detect all sequence changes, especially if the DNA fragment size is greater than 200 bp, but can be optimized to detect most DNA sequence variation. The reduced detection sensitivity is a disadvantage, but the increased throughput possible with SSCP makes it an attractive, viable alternative to direct sequencing for mutation detection on a research basis. The fragments which have shifted mobility on SSCP gels are then sequenced to determine the exact nature of the DNA sequence variation. Other approaches based on the detection of mismatches between the two complementary DNA strands include clamped denaturing gel electrophoresis (CDGE) (Sheffield et al., 1991), heteroduplex analysis (HA) (White et al., 1992) and chemical mismatch cleavage (CMC) (Grompe et al., 1989). None of the methods described above will detect large deletions, duplications or insertions, nor will they detect a regulatory mutation which affects transcription or translation of the protein. Other methods which might detect these classes of mutations such as a protein truncation assay or the asymmetric assay, detect only specific types of mutations and would not detect missense mutations. A review of currently available methods of detecting DNA sequence variation can be found in a recent review by Grompe (1993). Once a mutation is known, an allele specific detection approach such as allele specific oligonucleotide (ASO) hybridization can be utilized to rapidly screen large numbers of other samples for that same mutation. Such a technique can utilize probes which are labeled with gold nanoparticles to yield a visual color result (Elghanian et al., 1997).

A rapid preliminary analysis to detect polymorphisms in DNA sequences can be performed by looking at a series of Southern blots of DNA cut with one or more restriction enzymes, preferably with a large number of restriction enzymes. Each blot contains a series of normal individuals and a series of LQT cases. Southern blots displaying hybridizing fragments (differing in length from control DNA when probed with sequences near or including the KCNE2 locus) indicate a possible mutation. If restriction enzymes which produce very large restriction fragments are used, then pulsed field gel electrophoresis (PFGE) is employed.

Detection of point mutations may be accomplished by molecular cloning of the KCNE2 alleles and sequencing the alleles using techniques well known in the art. Also, the gene or portions of the gene may be amplified, e.g., by PCR or other amplification technique, and the amplified gene or amplified portions of the gene may be sequenced.

There are six well known methods for a more complete, yet still indirect, test for confirming the presence of a susceptibility allele: 1) single stranded conformation analysis (SSCP) (Orita et al., 1989); 2) denaturing gradient gel electrophoresis (DGGE) (Wartell et al., 1990; Sheffield et al., 1989); 3) RNase protection assays (Finkelstein et al., 1990; Kinszler et al., 1991); 4) allele-specific oligonucleotides (ASOs) (Conner et al., 1983); 5) the use of proteins which recognize nucleotide mismatches, such as the E. coli mutS protein (Modrich, 1991); and 6) allele-specific PCR (Ruano and Kidd, 1989). For allele-specific PCR, primers are used which hybridize at their 3' ends to a particular KCNE2 mutation. If the particular mutation is not present, an amplification product is not observed. Amplification Refractory Mutation System (ARMS) can also be used, as disclosed in European Patent Application Publication No. 0332435 and in Newton et al., 1989. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Such a method is particularly useful for screening relatives of an affected individual for the presence of the mutation found in that individual. Other techniques for detecting insertions and deletions as known in the art can be used.

In the first three methods (SSCP, DGGE and RNase protection assay), a new electrophoretic band appears. SSCP detects a band which migrates differentially because the sequence change causes a difference in single-strand, intramolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligonucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences.

Mismatches, according to the present invention, are hybridized nucleic acid duplexes in which the two strands are not 100% complementary. Lack of total homology may be due to deletions, insertions, inversions or substitutions. Mismatch detection can be used to detect point mutations in the gene or in its mRNA product. While these techniques are less sensitive than sequencing, they are simpler to perform on a large number of samples. An example of a mismatch cleavage technique is the RNase protection method. In the practice of the present invention, the method involves the use of a labeled riboprobe which is complementary to the human wild-type KCNE2 gene coding sequence. The riboprobe and either mRNA or DNA isolated from the person are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA. The riboprobe need not be the full length of the mRNA or gene but can be a segment of either. If the riboprobe comprises only a segment of the mRNA or gene, it will be desirable to use a number of these probes to screen the whole mRNA sequence for mismatches.

In similar fashion, DNA probes can be used to detect mismatches, through enzymatic or chemical cleavage. See, e.g., Cotton et al., 1988; Shenk et al., 1975; Novack et al., 1986. Alternatively, mismatches can be detected by shifts in the electrophoretic mobility of mismatched duplexes relative to matched duplexes. See, e.g., Cariello, 1988. With either riboprobes or DNA probes, the cellular mRNA or DNA which might contain a mutation can be amplified using PCR (see below) before hybridization. Changes in DNA of the KCNE2 gene can also be detected using Southern hybridization, especially if the changes are gross rearrangements, such as deletions and insertions.

DNA sequences of the KCNE2 gene which have been amplified by use of PCR may also be screened using allele-specific probes. These probes are nucleic acid oligomers, each of which contains a region of the gene sequence harboring a known mutation. For example, one oligomer may be about 30 nucleotides in length, corresponding to a portion of the gene sequence. By use of a battery of such allele-specific probes, PCR amplification products can be screened to identify the presence of a previously identified mutation in the gene. Hybridization of allele-specific probes with amplified KCNE2 sequences can be performed, for example, on a nylon filter. Hybridization to a particular probe under high stringency hybridization conditions indicates the presence of the same mutation in the tissue as in the allele-specific probe.

The newly developed technique of nucleic acid analysis via microchip technology is also applicable to the present invention. In this technique, literally thousands of distinct oligonucleotide probes are built up in an array on a silicon chip. Nucleic acid to be analyzed is fluorescently labeled and hybridized to the probes on the chip. It is also possible to study nucleic acid-protein interactions using these nucleic acid microchips. Using this technique one can determine the presence of mutations or even sequence the nucleic acid being analyzed or one can measure expression levels of a gene of interest. The method is one of parallel processing of many, even thousands, of probes at once and can tremendously increase the rate of analysis. Several papers have been published which use this technique. Some of these are Hacia et al., 1996; Shoemaker et al., 1996; Chee et al., 1996; Lockhart et al., 1996; DeRisi et al., 1996; Lipshutz et al., 1995. This method has already been used to screen people for mutations in the breast cancer gene BRCA1 (Hacia et al., 1996). This new technology has been reviewed in a news article in Chemical and Engineering News (Borman, 1996) and been the subject of an editorial (Editorial, Nature Genetics, 1996). Also see Fodor (1997).

The most definitive test for mutations in a candidate locus is to directly compare genomic KCNE2 sequences from patients with those from a control population. Alternatively, one could sequence messenger RNA after amplification, e.g., by PCR, thereby eliminating the necessity of determining the exon structure of the candidate gene.

Mutations from patients falling outside the coding region of KCNE2 can be detected by examining the non-coding regions, such as introns and regulatory sequences near or within the genes. An early indication that mutations in noncoding regions are important may come from Northern blot experiments that reveal messenger RNA molecules of abnormal size or abundance in patients as compared to control individuals.

Alteration of KCNE2 mRNA expression can be detected by any techniques known in the art. These include Northern blot analysis, PCR amplification and RNase protection. Diminished mRNA expression indicates an alteration of the wild-type gene. Alteration of wild-type genes can also be detected by screening for alteration of wild-type KCNE2 protein. For example, monoclonal antibodies immunoreactive with KCNE2 can be used to screen a tissue. Lack of cognate antigen would indicate a mutation. Antibodies specific for products of mutant alleles could also be used to detect mutant gene product. Such immunological assays can be done in any convenient formats known in the art. These include Western blots, immunohistochemical assays and ELISA assays. Any means for detecting an altered KCNE2 protein can be used to detect alteration of the wild-type KCNE2 gene. Functional assays, such as protein binding determinations, can be used. In addition, assays can be used which detect KCNE2 biochemical function. Finding a mutant KCNE2 gene product indicates alteration of a wild-type KCNE2 gene.

A mutant KCNE2 gene or gene product can also be detected in other human body samples, such as serum, stool, urine and sputum. The same techniques discussed above for detection of mutant genes or gene products in tissues can be applied to other body samples. By screening such body samples, a simple early diagnosis can be achieved for LQT.

The primer pairs of the present invention are useful for determination of the nucleotide sequence of a particular KCNE2 allele using PCR. The pairs of single-stranded DNA primers for KCNE2 can be annealed to sequences within or surrounding the KCNE2 gene in order to prime amplifying DNA synthesis of the gene itself. A complete set of these primers allows synthesis of all of the nucleotides of the gene coding sequences, i.e., the exons. The set of primers preferably allows synthesis of both intron and exon sequences. Allele-specific primers can also be used. Such primers anneal only to particular KCNE2 mutant alleles, and thus will only amplify a product in the presence of the mutant allele as a template.

In order to facilitate subsequent cloning of amplified sequences, primers may have restriction enzyme site sequences appended to their 5' ends. Thus, all nucleotides of the primers are derived from KCNE2 sequence or sequences adjacent to KCNE2, except for the few nucleotides necessary to form a restriction enzyme site. Such enzymes and sites are well known in the art. The primers themselves can be synthesized using techniques which are well known in the art. Generally, the primers can be made using oligonucleotide synthesizing machines which are commercially available. Given the sequence of KCNE2, design of particular primers is well within the skill of the art. The present invention adds to this by presenting data on the intron/exon boundaries thereby allowing one to design primers to amplify and sequence all of the exonic regions completely.

The nucleic acid probes provided by the present invention are useful for a number of purposes. They can be used in Southern hybridization to genomic DNA and in the RNase protection method for detecting point mutations already discussed above. The probes can be used to detect PCR amplification products. They may also be used to detect mismatches with the KCNE2 gene or mRNA using other techniques.

It has been discovered that individuals with the wild-type KCNE2 gene do not have LQT. However, mutations which interfere with the function of the KCNE2 gene product are involved in the pathogenesis of LQT. Thus, the presence of an altered (or a mutant) KCNE2 gene which produces a protein having a loss of function, or altered function, directly causes LQT which increases the risk of cardiac arrhythmias. In order to detect a KCNE2 gene mutation, a biological sample is prepared and analyzed for a difference between the sequence of the allele being analyzed and the sequence of the wild-type allele. Mutant KCNE2 alleles can be initially identified by any of the techniques described above. The mutant alleles are then sequenced to identify the specific mutation of the particular mutant allele. Alternatively, mutant alleles can be initially identified by identifying mutant (altered) proteins, using conventional techniques. The mutant alleles are then sequenced to identify the specific mutation for each allele. The mutations, especially those which lead to an altered function of the protein, are then used for the diagnostic and prognostic methods of the present invention.

It has also been discovered that the HERG protein coassembles with the MiRP1 (KCNE2) protein. Thus, mutations in KCNE2 which interfere in the function of the KCNE2 gene product are involved in the pathogenesis of LQT. Thus, the presence of an altered (or a mutant) KCNE2 gene which produces a protein having a loss of function, or altered function, directly causes LQT which increases the risk of cardiac arrhythmias. In order to detect a KCNE2 gene mutation, a biological sample is prepared and analyzed for a difference between the sequence of the allele being analyzed and the sequence of the wild-type allele. Mutant KCNE2 alleles can be initially identified by any of the techniques described above. The mutant alleles are then sequenced to identify the specific mutation of the particular mutant (altered) proteins, using conventional techniques. The mutant alleles are then sequenced to identify the specific mutation for each allele. The mutations, especially those which lead to an altered function of the protein, are then used for the diagnostic and prognostic methods of the present invention.

The Examples describe several features of the present invention as now presented. The KCNE peptides are an emerging superfamily required for normal ion channel function. MinK, encoded by KCNE1, has 129 amino acids, a single transmembrane segment, and is expressed in numerous tissues (Takumi et al., 1988; Swanson et al., 1993). Inherited mutations of MinK are associated with LQTS and congenital deafness (Schulze-Bahr et al., 1997; Splawski et al., 1997; Tyson et al., 1997; Duggal et al., 1998). The molecular basis for these disturbances is understood: $I_{Ks}$ channels, essential to normal function of the heart and auditory system, are co-assemblies of MinK and KvLQT1, a pore-forming subunit (Barhanin et al., 1996; Sanguinetti et al., 1996; Vetter et al., 1996). While channels containing only KvLQT1 subunits can function in experimental cells, $I_{Ks}$ channels have slower activation and deactivation kinetics, larger single-channel conductance, higher affinity for Class III antiarrhythmics and greater sensitivity to second messengers (Sanguinetti et al., 1996; Busch et al., 1997; Kaczmarek and Blumenthal, 1997; Sesti and Goldstein, 1998; Yang and Sigworth, 1998). These properties are due to intimate physical association of MinK and KVlQT1 subunits (Goldstein and Miller, 1991; Wang et al., 1996; Tai et al., 1997; Sesti and Goldstein, 1998; Tai and Goldstein, 1998). Despite its functional and clinical significance, this type of mixed complex was thought uncommon as MinK homologs, or subunits subserving a similar function, had been unknown.

Here we have delineated the chromosomal location, cDNA sequence and predicted product, wild type behavior and arrhythmia-association of the first gene homologous to KCNE1 (MinK). MiRP1, encoded by KCNE2, has 123 amino acids, a single predicted transmembrane segment, and is expressed in cardiac and skeletal muscle. Like MinK, MiRP1 co-assembles with a pore-forming subunit to create stable complexes whose functional attributes resemble those of a native cardiac potassium channel. While MinK/KvLQT1 complexes recreate the behaviors of $I_{Ks}$ channels, MiRP1/HERG complexes recapitulate those of $I_{Kr}$ channels. Compared to channels formed by HERG subunits alone, those containing MiRP1 show altered voltage-dependent activation, kinetics of deactivation, unitary conductance, sensitivity to regulation by external $K^+$ and pharmacology. In mutant form, MiRP1 is associated with inherited and acquired cardiac arrhythmia. MinK and MiRP1 are revealed to be essential for normal cardiac ion channel function.

KCNE peptides are incorporated into a variety of channel assemblies in native cells. Functional specificity is inferred from the absence of effects when rMiRP1 was co-expressed with seven different K$^+$ channel subunits in oocytes. Specific binding is indicated by the preferential association of MiRP1 rather than MinK with HERG in vitro (FIG. 6) even though MinK/HERG assemblies can form (FIG. 6; McDonald et al., 1997). While a role for KCNE peptides in channels other than I$_{Kr}$ and I$_{Ks}$ seems probable, studies of human and mouse MiRP2 (KCNE3) and mouse MiRP3 (KCNE4) have indicated only that they do not alter HERG or KvLQT1 currents nor activate channel subunits endogenous to oocytes.

MiRP1/HERG complexes function like native cardiac I$_{Kr}$ channels. Channels formed only with HERG subunits are known to differ from native I$_{Kr}$ channels in gating, conductance, regulation by K$^+$ and block by methanesulfonanilides (Sanguinetti et al., 1995; Trudeau et al., 1995; Spector et al., 1996; Zou et al., 1997; Ho et al., 1998) and (Shibasaki, 1987; Sanguinetti and Jurkiewicz, 1992; Yang et al., 1994; Veldkamp et al., 1995; Ho et al., 1996; Howarth et al., 1996). The idea that native I$_{Kr}$ channels are formed by co-assembly of MiRP1 and HERG subunits is consistent with 6 observations reported here.

Figure 7B:
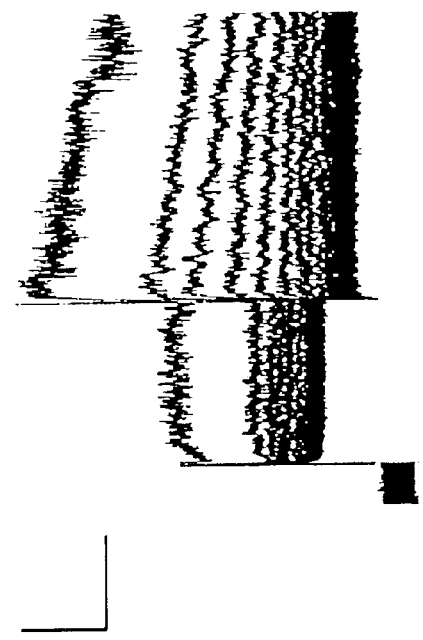
FIGS. 7A–7C show that channels formed with hMiRP1 and HERG (but not those with HERG alone) are blocked by E-4031 with biphasic kinetics. CHO cells expressing channel subunits as indicated were stepped from −80 mV to +20 mV for 1 s and then to −40 mV for 2 s with a 0.5 s intercycle interval. Cells were studied for 4 cycles before drug application, held closed at −80 mV for 1 min in the presence of 1 μM E-4031 (bar), and then studied for 30–70 cycles in the continued presence of the drug.
Figure 7A:
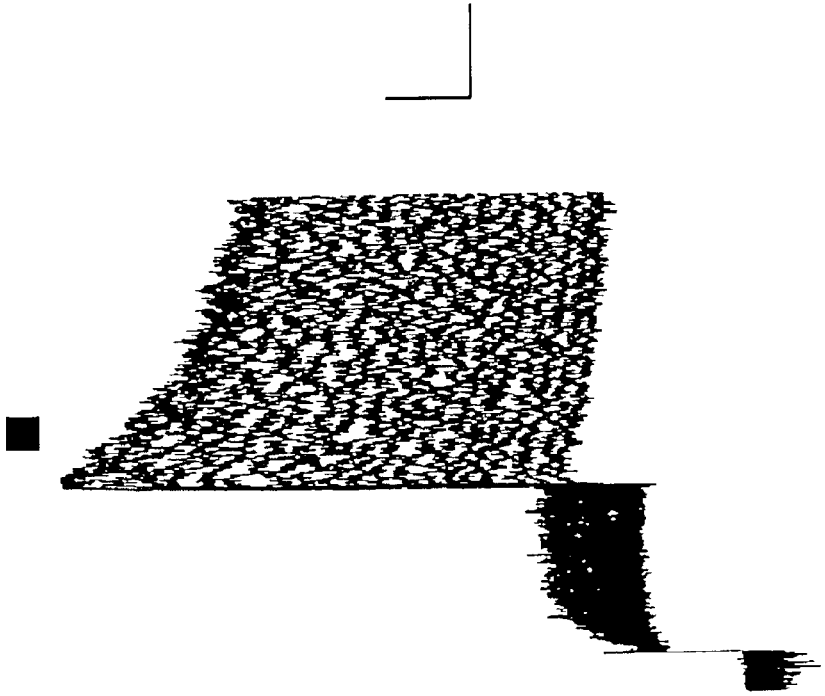

First, the single-channel conductance of channels containing MiRP1 is smaller than that of HERG channels but the same as that of I$_{Kr}$ channels in isolated rabbit and human cardiocytes (Shibasaki, 1987; Veldkamp et al., 1995; Zou et al., 1997). Second, MiRP1/HERG complexes and I$_{Kr}$ channels in murine and human cardiac myocytes deactivate 3-fold more rapidly than channels formed only of HERG subunits (Yang et al., 1994; Sanguinetti et al., 1995; London et al., 1997; Wang et al., 1997). Third, MiRP1/HERG complexes, like I$_{Kr}$ channels in murine atrial and guinea pig ventricular myocytes, are less sensitive to regulation by external K$^+$ than HERG channels (Shibasaki, 1987; Scamps and Carmeliet, 1989; Sanguinetti and Jurkiewicz, 1992; Sanguinetti et al., 1995; Yang and Roden, 1996; Yang et al., 1997). Fourth, MiRP1 and HERG subunits co-assemble in stable fashion. Fifth, a hallmark of native I$_{Kr}$ channels is that blockade by methanesulfonanilide Class III antiarrhythmics proceeds in two phases, a fast phase seen with the first test pulse and a slow phase (Carmeliet, 1992). Conversely, HERG channels require repetitive pulsing to voltages positive to the threshold for activation before significant blockade develops (Spector et al., 1996). Like native I$_{Kr}$ channels in cardiac myocytes, channels formed by assembly of hMiRP1 and HERG show biphasic E-4031 blockade—mixed complexes are significantly inhibited with the first test pulse and slowly relax to equilibrium blockade (FIG. 7B, c) while channels formed by HERG subunits alone are inhibited only after repetitive test pulses (FIG. 7A). Finally, Q9E-hMiRP1 increases clarithromycin sensitivity of MiRP1/HERG channels in vitro (FIG. 9). Clarithromycin is known to block I$_{Kr}$ currents in isolated guinea pig and canine ventricular myocytes and, at high doses, to induce a prolonged QT interval and TdP in humans (Daleau et al., 1995; Antzelevitch et al., 1996; Katapadi et al., 1997). That the mutant was isolated from a patient with clarithromycin-induced Torsades de pointes (TdP) and VF supports the thesis that native cardiac I$_{Kr}$ channels are formed with hMiRP1.

hKCNE2 is an arrhythmia susceptibility gene. Molecular genetic data supporting the hypothesis that mutations in the gene for MiRP1 predispose to arrhythmia include identification of 3 missense mutations associated with LQTS and/or VF. Q9E-hMiRP1 was identified in 1 of 20 individuals with drug-induced arrhythmia. M54T-hMiRP1 and I57T-hMiRP1 were each isolated in 1 of 230 individuals with inherited or sporadic arrhythmias. Non-genetic data supporting the hypothesis include the observations that I$_{Kr}$ dysfunction is known to cause LQTS and arrhythmia susceptibility, that MiRP1 and HERG coassemble to form I$_{Kr}$-like channels and that arrhythmia-associated mutations in KCNE2 have deleterious effects on channels formed in vitro. The alternative explanation, that these are common polymorphisms, has been disproved.

MinK and MiRP1 mutants associated with arrhythmia have common effects. Four mutants of MinK have been associated with inherited LQTS: T71, D76N, S74L and TL58,59PP (Schulze-Bahr et al., 1997; Splawski et al., 1997; Tyson et al., 1997; Duggal et al., 1998). Formation of I$_{Ks}$ channels with S74L and/or D76N-MinK decreases K$^+$ flux (and prolongs the cardiac action potential) by shifting V$_{1/2}$ for activation to more depolarized voltages, speeding deactivation (Splawski et al., 1997; Sesti and Goldstein, 1998) and decreasing single-channel conductance (Sesti and Goldstein, 1998). In a similar fashion, MiRP1 mutants associated with prolongation of the QT interval decrease K$^+$ current by increasing the voltage-dependence of activation and speeding deactivation. Currents through channels formed with Q9E-hMiRP1 are further reduced compared to wild type when exposed to clarithromycin as they are more sensitive to drug blockade (FIG. 9).

Arrhythmia-associated mutations in MiRP1, MinK, HERG and KvLQT1 produce changes in channel function of similar magnitude. Q9E-hMiRP1 impedes activation and increases sensitivity to macrolide antibiotics (causing a 60% reduction in current relative to wild type at 0 mV with 0.5 mM clarithromycin). M54T-hMiRP1 forms I$_{Kr}$ channels which deactivate twice as fast as wild type, showing a 54% reduction in $\tau_{fast}$ (Table 1). Similarly, loss-of-function mutations in HERG and KvLQT1 caused 50–80% reduction in peak currents (Sanguinetti et al., 1996; Wollnik et al., 1997) while other LQTS-associated HERG mutants increased deactivation rates by reducing $\tau_{fast}$ from 49–84% (Chen et al., 1999). S74L and D76N-MinK mutations associated with LQTS form I$_{Ks}$ channels with 40–70% reduced single channel conductance and deactivation rates that are 33–75% faster (Sesti and Goldstein, 1998). Conversely, T8A-hMiRP1 was not disease-associated and functioned like wild type except for a negative shift of 8 mV in the V$_{1/2}$ for activation. This is not expected to cause arrhythmia, as the allele should enhance the capacity of I$_{Kr}$ channels to achieve myocardial repolarization.

The occurrence of TdP during treatment with medications that prolong the cardiac action potential is unpredictable. TdP is a recognized risk of treatment with various antiarrhythmic agents including quinidine (Roden et al., 1986), sotalol (Hohnloser and Woosley, 1994) and ibutilide (Ellenbogen et al., 1996), the antihistamine terfenadine (Woosley et al., 1993), the gastrointestinal prokinetic agent cisapride (Carlsson et al., 1997) and the macrolide antibiotics erythromycin (Daleau et al., 1995; Antzelevitch et al., 1996) and clarithromycin (Kundu et al., 1997; Lee et al., 1998). In each case, the agents diminish cardiac K$^+$ currents, in some cases by inhibition of I$_{Kr}$ channels. Baseline characteristics that identify patients at risk for drug-induced TdP include inherited prolongation of QT interval, hypokalemia, female gender and slow heart rate, each of which prolongs the action potential duration; these observations led Roden (1998) to develop the concept of a repolarizalion reserve, that is, excess capacity of the myocardium to effect orderly and rapid repolarization via normal mechanisms. Risk factors for TdP reduce this reserve and make the precipitation of arrhythmia by further stressors more likely.

Thus, a plausible scenario for a prolonged QT interval at baseline in the patient carrying Q9E-hMiRP1 is formation of channels that activate less readily and, therefore, pass less K$^+$ to accomplish repolarization in a timely fashion. Three additional factors leading to decreased K$^+$ current may have predisposed this patient to TdP and VF. First, clarithromycin blocks cardiac I$_{Kr}$ channels; this effect would be more pronounced in the patient as Q9E-hMiRP1 channels are 3-fold more sensitive to the drug. Second, concurrent hypokalemia diminishes I$_{Kr}$ channel activity and further increases inhibition by the macrolide antibiotic. Third, female gender is an independent risk factor, possibly due to gender-specific differences in I$_{Kr}$ density, as seen in rabbit ventricular myocytes (Makkar et al., 1993; Drici et al., 1998; Ebert et al., 1998). Our results support the idea that acquired arrhythmia can result from inheritance of a mutant channel subunit that reduces cardiac repolarization capacity but is well-tolerated until provocative stimuli further decrease the ability of the myocardium to repolarize normally.

Definitions

The present invention employs the following definitions and methods of use, which are, where appropriate, referenced to KCNE2. However, such definitions and methods of use are also applicable to KCNE3 and KCNE4.

"Amplification of Polynucleotides" utilizes methods such as the polymerase chain reaction (PCR), ligation amplification (or ligase chain reaction, LCR) and amplification methods based on the use of Q-beta replicase. Also useful are strand displacement amplification (SDA), thermophilic SDA, and nucleic acid sequence based amplification (3SR or NASBA). These methods are well known and widely practiced in the art. See, e.g., U.S. Pat. Nos. 4,683,195 and 4,683,202 and Innis et al., 1990 (for PCR); Wu and Wallace, 1989 (for LCR); U.S. Pat. Nos. 5,270,184 and 5,455,166 and Walker et al., 1992 (for SDA); Spargo et al., 1996 (for thermophilic SDA) and U.S. Pat. No. 5,409,818, Fahy et al., 1991 and Compton, 1991 for 3SR and NASBA. Reagents and hardware for conducting PCR are commercially available. Primers useful to amplify sequences from the KCNE2 region are preferably complementary to, and hybridize specifically to sequences in the KCNE2 region or in regions that flank a target region therein. KCNE2 sequences generated by amplification may be sequenced directly. Alternatively, but less desirably, the amplified sequence(s) may be cloned prior to sequence analysis. A method for the direct cloning and sequence analysis of enzymatically amplified genomic segments has been described by Scharf et al., 1986.

"Analyte polynucleotide" and "analyte strand" refer to a single- or double-stranded polynucleotide which is suspected of containing a target sequence, and which may be present in a variety of types of samples, including biological samples.

"Antibodies." The present invention also provides polyclonal and/or monoclonal antibodies and fragments thereof, and immunologic binding equivalents thereof, which are capable of specifically binding to the KCNE2 polypeptide and fragments thereof or to polynucleotide sequences from the KCNE2 region. The term "antibody" is used both to refer to a homogeneous molecular entity, or a mixture such as a serum product made up of a plurality of different molecular entities. Polypeptides may be prepared synthetically in a peptide synthesizer and coupled to a carrier molecule (e.g., keyhole limpet hemocyanin) and injected over several months into rabbits. Rabbit sera is tested for immunoreactivity to the KCNE2 polypeptide or fragment. Monoclonal antibodies may be made by injecting mice with the protein polypeptides, fusion proteins or fragments thereof. Monoclonal antibodies will be screened by ELISA and tested for specific immunoreactivity with KCNE2 polypeptide or fragments thereof. See, Harlow and Lane, 1988. These antibodies will be useful in assays as well as pharmaceuticals.

Once a sufficient quantity of desired polypeptide has been obtained, it may be used for various purposes. A typical use is the production of antibodies specific for binding. These antibodies may be either polyclonal or monoclonal, and may be produced by in vitro or in vivo techniques well known in the art. For production of polyclonal antibodies, an appropriate target immune system, typically mouse or rabbit, is selected. Substantially purified antigen is presented to the immune system in a fashion determined by methods appropriate for the animal and by other parameters well known to immunologists. Typical sites for injection are in footpads, intramuscularly, intraperitoneally, or intradermally. Of course, other species may be substituted for mouse or rabbit. Polyclonal antibodies are then purified using techniques known in the art, adjusted for the desired specificity.

An immunological response is usually assayed with an immunoassay. Normally, such immunoassays involve some purification of a source of antigen, for example, that produced by the same cells and in the same fashion as the antigen. A variety of immunoassay methods are well known in the art. See, e.g., Harlow and Lane, 1988, or Goding, 1986.

Monoclonal antibodies with affinities of $10^{-8}$ M$^{-1}$ or preferably $10^{-9}$ to $10^{-10}$ M$^{-1}$ or stronger will typically be made by standard procedures as described, e.g., in Harlow and Lane, 1988 or Goding, 1986. Briefly, appropriate animals will be selected and the desired immunization protocol followed. After the appropriate period of time, the spleens of such animals are excised and individual spleen cells fused, typically, to immortalized myeloma cells under appropriate selection conditions. Thereafter, the cells are clonally separated and the supernatants of each clone tested for their production of an appropriate antibody specific for the desired region of the antigen.

Other suitable techniques involve in vitro exposure of lymphocytes to the antigenic polypeptides, or alternatively, to selection of libraries of antibodies in phage or similar vectors. See Huse et al., 1989. The polypeptides and antibodies of the present invention may be used with or without modification. Frequently, polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced (see U.S. Pat. No. 4,816,567).

"Binding partner" refers to a molecule capable of binding a ligand molecule with high specificity, as for example, an antigen and an antigen-specific antibody or an enzyme and its inhibitor. In general, the specific binding partners must bind with sufficient affinity to immobilize the analyte copy/complementary strand duplex (in the case of polynucleotide hybridization) under the isolation conditions. Specific binding partners are known in the art and include, for example, biotin and avidin or streptavidin, IgG and protein A, the numerous, known receptor-ligand couples, and complementary polynucleotide strands. In the case of complementary polynucleotide binding partners, the partners are normally at least about 15 bases in length, and may be at least 40 bases in length. It is well recognized by those of skill in the art that lengths shorter than 15 (e.g., 8 bases), between 15 and 40, and greater than 40 bases may also be used. The polynucleotides may be composed of DNA, RNA, or synthetic nucleotide analogs. Further binding partners can be identified using, e.g., the two-hybrid yeast screening assay as described herein.

A "biological sample" refers to a sample of tissue or fluid suspected of containing an analyte polynucleotide or polypeptide from an individual including, but not limited to, e.g., plasma, serum, spinal fluid, lymph fluid, the external sections of the skin, respiratory, intestinal, and genitourinary tracts, tears, saliva, blood cells, tumors, organs, tissue and samples of in vitro cell culture constituents.

"Encode". A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

"Isolated" or "substantially pure". An "isolated" or "substantially pure" nucleic acid (e.g., an RNA, DNA or a mixed polymer) is one which is substantially separated from other cellular components which naturally accompany a native human sequence or protein, e.g., ribosomes, polymerases, many other human genome sequences and proteins. The term embraces a nucleic acid sequence or protein which has been removed from its naturally occurring environment, and includes recombinant or cloned DNA isolates and chemically synthesized analogs or analogs biologically synthesized by heterologous systems.

"KCNE2 Allele" refers, respectively, to normal alleles of the KCNE2 locus as well as alleles of KCNE2 carrying variations that cause LQT.

"KCNE2 Locus", "KCNE2 Gene", "KCNE2 Nucleic Acids" or "KCNE2 Polynucleotide" each refer to polynucleotides, all of which are in the KCNE2 region, respectively, that are likely to be expressed in normal tissue, certain alleles of which result in LQT. The KCNE2 locus is intended to include coding sequences, intervening sequences and regulatory elements controlling transcription and/or translation. The KCNE2 locus is intended to include all allelic variations of the DNA sequence. The terms "KCNE2" and "MiRP1" may be used interchangeably. Similarly, the KCNE3 locus is intended to include coding sequences, intervening sequences and regulatory elements controlling transcription and/or translation. The KCNE3 locus is intended to include all allelic variations of the DNA sequence. The terms "KCNE3" and "MiRP2" may be used interchangeably. Similarly, the KCNE4 locus is intended to include coding sequences, intervening sequences and regulatory elements controlling transcription and/or translation. The KCNE4 locus is intended to include all allelic variations of the DNA sequence. The terms "KCNE4" and "MiRP3" may be used interchangeably.

These terms, when applied to a nucleic acid, refer to a nucleic acid which encodes a human KCNE2 polypeptide, fragment, homolog or variant, including, e.g., protein fusions or deletions. The nucleic acids of the present invention will possess a sequence which is either derived from, or substantially similar to a natural KCNE2-encoding gene or one having substantial homology with a natural KCNE2-encoding gene or a portion thereof.

The KCNE2 gene or nucleic acid includes normal alleles of the KCNE2 gene, respectively, including silent alleles having no effect on the amino acid sequence of the KCNE2 polypeptide as well as alleles leading to amino acid sequence variants of the KCNE2 polypeptide that do not substantially affect its function. These terms also include alleles having one or more mutations which adversely affect the function of the KCNE2 polypeptide. A mutation may be a change in the KCNE2 nucleic acid sequence which produces a deleterious change in the amino acid sequence of the KCNE2 polypeptide, resulting in partial or complete loss of KCNE2 function, respectively, or may be a change in the nucleic acid sequence which results in the loss of effective KCNE2 expression or the production of aberrant forms of the KCNE2 polypeptide.

The KCNE2 nucleic acid may be that shown in SEQ ID NO:1 (human) or SEQ ID NO:3 (rat) or it may be an allele as described above or a variant or derivative differing from that shown by a change which is one or more of addition, insertion, deletion and substitution of one or more nucleotides of the sequence shown. Changes to the nucleotide sequence may result in an amino acid change at the protein level, or not, as determined by the genetic code. Similar considerations and scope apply to human KCNE3 (SEQ ID NO:5), mouse KCNE3 (SEQ ID NO:7), human KCNE4 (SEQ ID NO:9) and mouse KCNE4 (SEQ ID NO: 11) as described herein for KCNE2.

Thus, nucleic acid according to the present invention may include a sequence different from the sequence shown in SEQ ID NOs:1 and 3 yet encode a polypeptide with the same amino acid sequence as shown in these figures. That is, nucleic acids of the present invention include sequences which are degenerate as a result of the genetic code. On the other hand, the encoded polypeptide may comprise an amino acid sequence which differs by one or more amino acid residues from the amino acid sequence shown in SEQ ID NOs:2 and 4. Nucleic acid encoding a polypeptide which is an amino acid sequence variant, derivative or allele of the amino acid sequence shown in SEQ ID NOs:2 and 4 is also provided by the present invention.

The KCNE2 gene, respectively, also refers to (a) any DNA sequence that (i) hybridizes to the complement of the DNA sequences that encode the amino acid sequence set forth in SEQ ID NO:1 (human) or SEQ ID NO:3 (rat) under highly stringent conditions (Ausubel et al., 1992) and (ii) encodes a gene product functionally equivalent to KCNE2, or (b) any DNA sequence that (i) hybridizes to the complement of the DNA sequences that encode the amino acid sequence set forth in SEQ ID Nos:2 and 4 under less stringent conditions, such as moderately stringent conditions (Ausubel et al., 1992) and (ii) encodes a gene product functionally equivalent to KCNE2. The invention also includes nucleic acid molecules that are the complements of the sequences described herein.

The polynucleotide compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The present invention provides recombinant nucleic acids comprising all or part of the KCNE2 region. The recombinant construct may be capable of replicating autonomously in a host cell. Alternatively, the recombinant construct may become integrated into the chromosomal DNA of the host cell. Such a recombinant polynucleotide comprises a polynucleotide of genomic, cDNA, semi-synthetic, or synthetic origin which, by virtue of its origin or manipulation, 1) is not associated with all or a portion of a polynucleotide with which it is associated in nature; 2) is linked to a polynucleotide other than that to which it is linked in nature; or 3) does not occur in nature. Where nucleic acid according to the invention includes RNA, reference to the sequence shown should be construed as reference to the RNA equivalent, with U substituted for T.

Therefore, recombinant nucleic acids comprising sequences otherwise not naturally occurring are provided by this invention. Although the wild-type sequence may be employed, it will often be altered, e.g., by deletion, substitution or insertion. cDNA or genomic libraries of various types may be screened as natural sources of the nucleic acids of the present invention, or such nucleic acids may be provided by amplification of sequences resident in genomic DNA or other natural sources, e.g., by PCR. The choice of cDNA libraries normally corresponds to a tissue source which is abundant in mRNA for the desired proteins. Phage libraries are normally preferred, but other types of libraries may be used. Clones of a library are spread onto plates, transferred to a substrate for screening, denatured and probed for the presence of desired sequences.

The DNA sequences used in this invention will usually comprise at least about five codons (15 nucleotides), more usually at least about 7–15 codons, and most preferably, at least about 35 codons. One or more introns may also be present. This number of nucleotides is usually about the minimal length required for a successful probe that would hybridize specifically with a KCNE2-encoding sequence. In this context, oligomers of as low as 8 nucleotides, more generally 8–17 nucleotides, can be used for probes, especially in connection with chip technology.

Techniques for nucleic acid manipulation are described generally, for example, in Sambrook et al., 1989 or Ausubel et al., 1992. Reagents useful in applying such techniques, such as restriction enzymes and the like, are widely known in the art and commercially available from such vendors as New England BioLabs, Boehringer Mannheim, Amersham, Promega, U.S. Biochemicals, New England Nuclear, and a number of other sources. The recombinant nucleic acid sequences used to produce fusion proteins of the present invention may be derived from natural or synthetic sequences. Many natural gene sequences are obtainable from various cDNA or from genomic libraries using appropriate probes. See, GenBank, National Institutes of Health.

As used herein, a "portion" of the KCNE2 locus or region or allele is defined as having a minimal size of at least about eight nucleotides, or preferably about 15 nucleotides, or more preferably at least about 25 nucleotides, and may have a minimal size of at least about 40 nucleotides. This definition includes all sizes in the range of 8–40 nucleotides as well as greater than 40 nucleotides. Thus, this definition includes nucleic acids of 8, 12, 15, 20, 25, 40, 60, 80, 100, 200, 300, 400, 500 nucleotides, or nucleic acids having any number of nucleotides within these ranges of values (e.g., 9, 10, 11, 16, 23, 30, 38, 50, 72, 121, etc., nucleotides), or nucleic acids having more than 500 nucleotides. The present invention includes all novel nucleic acids having at least 8 nucleotides derived from SEQ ID NOs:1, 3, 5, 7, 9 and 11, its complement or functionally equivalent nucleic acid sequences. The present invention does not include nucleic acids which exist in the prior art. That is, the present invention includes all nucleic acids having at least 8 nucleotides derived from SEQ ID Nos:1, 3, 5, 7, 9 and 11 with the proviso that it does not include nucleic acids existing in the prior art.

"KCNE2 protein" or "KCNE2 polypeptide" refers to a protein or polypeptide encoded by the KCNE2 locus, variants or fragments thereof. The terms "KCNE2" and "MiRP1" are used interchangeably. Similarly, KCNE3 protein refers to a protein encoded by the KCNE3 locus, variants and fragments thereof. The terms "KCNE3" and "MiRP2" are used interchangeably. Similarly, KCNE4 protein refers to a protein encoded by the KCNE3 locus, variants and fragments thereof. The terms "KCNE4" and "MiRP3" are used interchangeably. The term "polypeptide" refers to a polymer of amino acids and its equivalent and does not refer to a specific length of the product; thus, peptides, oligopeptides and proteins are included within the definition of a polypeptide. This term also does not refer to, or exclude modifications of the polypeptide, for example, glycosylations, acetylations, phosphorylations, and the like. Included within the definition are, for example, polypeptides containing one or more analogs of an amino acid (including, for example, unnatural amino acids, etc.), polypeptides with substituted linkages as well as other modifications known in the art, both naturally and non-naturally occurring. Ordinarily, such polypeptides will be at least about 50% homologous to the native KCNE2 sequence, preferably in excess of about 90%, and more preferably at least about 95% homologous. Also included are proteins encoded by DNA which hybridize under high or low stringency conditions, to KCNE2-encoding nucleic acids and closely related polypeptides or proteins retrieved by antisera to the KCNE2 protein (s).

The KCNE2 polypeptide may be that shown in SEQ ID NOs:2 (human) and 4 (rat) which may be in isolated and/or purified form, free or substantially free of material with which it is naturally associated. The polypeptide may, if produced by expression in a prokaryotic cell or produced synthetically, lack native post-translational processing, such as glycosylation. Alternatively, the present invention is also directed to polypeptides which are sequence variants, alleles or derivatives of the KCNE2 polypeptide. Such polypeptides may have an amino acid sequence which differs from that set forth in SEQ ID Nos:2 or 4 by one or more of addition, substitution, deletion or insertion of one or more amino acids. Preferred such polypeptides have KCNE2 function. Similar considerations and scope apply to human KCNE3 (SEQ ID NO:6), mouse KCNE3 (SEQ ID NO:8), human KCNE4 (SEQ ID NO:10) and mouse KCNE4 (SEQ ID NO:12) as described herein for KCNE2.

Substitutional variants typically contain the exchange of one amino acid for another at one or more sites within the protein, and may be designed to modulate one or more properties of the polypeptide, such as stability against proteolytic cleavage, without the loss of other functions or properties. Amino acid substitutions may be made on the basis of similarity in polarity, charge, solubility, hydrophobicity, hydrophilicity, and/or the amphipathic nature of the residues involved. Preferred substitutions are ones which are conservative, that is, one amino acid is replaced with one of similar shape and charge. Conservative substitutions are well known in the art and typically include substitutions within the following groups: glycine, alanine; valine, isoleucine, leucine; aspartic acid, glutamic acid; asparagine, glutamine; serine, threonine; lysine, arginine; and tyrosine, phenylalanine.

Certain amino acids may be substituted for other amino acids in a protein structure without appreciable loss of interactive binding capacity with structures such as, for example, antigen-binding regions of antibodies or binding sites on substrate molecules or binding sites on proteins interacting with the KCNE2 polypeptide. Since it is the interactive capacity and nature of a protein which defines that protein's biological functional activity, certain amino acid substitutions can be made in a protein sequence, and its underlying DNA coding sequence, and nevertheless obtain a protein with like properties. In making such changes, the hydropathic index of amino acids may be considered. The importance of the hydrophobic amino acid index in conferring interactive biological function on a protein is generally understood in the art (Kyte and Doolittle, 1982). Alternatively, the substitution of like amino acids can be made effectively on the basis of hydrophilicity. The importance of hydrophilicity in conferring interactive biological function of a protein is generally understood in the art (U.S. Pat. No. 4,554,101). The use of the hydrophobic index or hydrophilicity in designing polypeptides is further discussed in U.S. Pat. No. 5,691,198.

The length of polypeptide sequences compared for homology will generally be at least about 16 amino acids, usually at least about 20 residues, more usually at least about 24 residues, typically at least about 28 residues, and preferably more than about 35 residues.

"Operably linked" refers to a juxtaposition wherein the components so described are in a relationship permitting them to function in their intended manner. For instance, a promoter is operably linked to a coding sequence if the promoter affects its transcription or expression.

The term peptide mimetic or mimetic is intended to refer to a substance which has the essential biological activity of the KCNE2 polypeptide. A peptide mimetic may be a peptide-containing molecule that mimics elements of protein secondary structure (Johnson et al., 1993). The underlying rationale behind the use of peptide mimetics is that the peptide backbone of proteins exists chiefly to orient amino acid side chains in such a way as to facilitate molecular interactions, such as those of antibody and antigen, enzyme and substrate or scaffolding proteins. A peptide mimetic is designed to permit molecular interactions similar to the natural molecule. A mimetic may not be a peptide at all, but it will retain the essential biological activity of natural KCNE2 polypeptide.

"Probes". Polynucleotide polymorphisms associated with KCNE2 alleles which predispose to LQT are detected by hybridization with a polynucleotide probe which forms a stable hybrid with that of the target sequence, under stringent to moderately stringent hybridization and wash conditions. If it is expected that the probes will be perfectly complementary to the target sequence, high stringency conditions will be used. Hybridization stringency may be lessened if some mismatching is expected, for example, if variants are expected with the result that the probe will not be completely complementary. Conditions are chosen which rule out nonspecific/adventitious bindings, that is, which minimize noise. (It should be noted that throughout this disclosure, if it is simply stated that "stringent" conditions are used that it is meant to be read as "high stringency" conditions are used.) Since such indications identify neutral DNA polymorphisms as well as mutations, these indications need further analysis to demonstrate detection of a KCNE1 susceptibility allele.

Probes for KCNE2 alleles may be derived from the sequences of the KCNE2 region, its cDNA, functionally equivalent sequences, or the complements thereof The probes may be of any suitable length, which span all or a portion of the KCNE2 region, and which allow specific hybridization to the region. If the target sequence contains a sequence identical to that of the probe, the probes may be short, e.g., in the range of about 8–30 base pairs, since the hybrid will be relatively stable under even stringent conditions. If some degree of mismatch is expected with the probe, i.e., if it is suspected that the probe will hybridize to a variant region, a longer probe may be employed which hybridizes to the target sequence with the requisite specificity.

The probes will include an isolated polynucleotide attached to a label or reporter molecule and may be used to isolate other polynucleotide sequences, having sequence similarity by standard methods. For techniques for preparing and labeling probes see, e.g., Sambrook et al., 1989 or Ausubel et al., 1992. Other similar polynucleotides may be selected by using homologous polynucleotides. Alternatively, polynucleotides encoding these or similar polypeptides may be synthesized or selected by use of the redundancy in the genetic code. Various codon substitutions may be introduced, e.g., by silent changes (thereby producing various restriction sites) or to optimize expression for a particular system. Mutations may be introduced to modify the properties of the polypeptide, perhaps to change the polypeptide degradation or turnover rate.

Probes comprising synthetic oligonucleotides or other polynucleotides of the present invention may be derived from naturally occurring or recombinant single- or double-stranded polynucleotides, or be chemically synthesized. Probes may also be labeled by nick translation, Klenow fill-in reaction, or other methods known in the art.

Portions of the polynucleotide sequence having at least about eight nucleotides, usually at least about 15 nucleotides, and fewer than about 9 kb, usually fewer than about 1.0 kb, from a polynucleotide sequence encoding KCNE2 are preferred as probes. This definition therefore includes probes of sizes 8 nucleotides through 9000 nucleotides. Thus, this definition includes probes of 8, 12, 15, 20, 25, 40, 60, 80, 100, 200, 300, 400 or 500 nucleotides or probes having any number of nucleotides within these ranges of values (e.g., 9, 10, 11, 16, 23, 30, 38, 50, 72, 121, etc., nucleotides), or probes having more than 500 nucleotides. The probes may also be used to determine whether mRNA encoding KCNE2 is present in a cell or tissue. The present invention includes all novel probes having at least 8 nucleotides derived from SEQ ID Nos:1, 3, 5, 7, 9 and 11, its complement or functionally equivalent nucleic acid sequences. The present invention does not include probes which exist in the prior art. That is, the present invention includes all probes having at least 8 nucleotides derived from SEQ ID NOs:1, 3, 5, 7, 9 and 11, with the proviso that they do not include probes existing in the prior art.

Similar considerations and nucleotide lengths are also applicable to primers which may be used for the amplification of all or part of the KCNE2 gene. Thus, a definition for primers includes primers of 8, 12, 15, 20, 25, 40, 60, 80, 100, 200, 300, 400, 500 nucleotides, or primers having any number of nucleotides within these ranges of values (e.g., 9, 10, 11, 16, 23, 30, 38, 50, 72, 121, etc. nucleotides), or primers having more than 500 nucleotides, or any number of nucleotides between 500 and 9000. The primers may also be used to determine whether mRNA encoding KCNE2 is present in a cell or tissue. The present invention includes all novel primers having at least 8 nucleotides derived from the KCNE2 locus for amplifying the KCNE2 gene, its complement or functionally equivalent nucleic acid sequences. The present invention does not include primers which exist in the prior art. That is, the present invention includes all primers having at least 8 nucleotides with the proviso that it does not include primers existing in the prior art.

"Protein modifications or fragments" are provided by the present invention for KCNE2 polypeptides or fragments thereof which are substantially homologous to primary structural sequence but which include, e.g., in vivo or in vitro chemical and biochemical modifications or which incorporate unusual amino acids. Such modifications include, for example, acetylation, carboxylation, phosphorylation, glycosylation, ubiquitination, labeling, e.g., with radionuclides, and various enzymatic modifications, as will be readily appreciated by those well skilled in the art. A variety of methods for labeling polypeptides and of substituents or labels useful for such purposes are well known in the art, and include radioactive isotopes such as $^{32}P$, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods of labeling polypeptides are well known in the art. See Sambrook et al., 1989 or Ausubel et al., 1992.

Besides substantially full-length polypeptides, the present invention provides for biologically active fragments of the polypeptides. Significant biological activities include ligand-binding, immunological activity and other biological activities characteristic of KCNE2 polypeptides. Immunological activities include both immunogenic function in a target immune system, as well as sharing of immunological epitopes for binding, serving as either a competitor or substitute antigen for an epitope of the KCNE2 protein. As used herein, "epitope" refers to an antigenic determinant of a polypeptide. An epitope could comprise three amino acids in a spatial conformation which is unique to the epitope. Generally, an epitope consists of at least five such amino acids, and more usually consists of at least 8–10 such amino acids. Methods of determining the spatial conformation of such amino acids are known in the art.

For immunological purposes, tandem-repeat polypeptide segments may be used as immunogens, thereby producing highly antigenic proteins. Alternatively, such polypeptides will serve as highly efficient competitors for specific binding. Production of antibodies specific for KCNE2 polypeptides or fragments thereof is described below.

The present invention also provides for fusion polypeptides, comprising KCNE2 polypeptides and fragments. Homologous polypeptides may be fusions between two or more KCNE2 polypeptide sequences or between the sequences of KCNE2 and a related protein. Likewise, heterologous fusions may be constructed which would exhibit a combination of properties or activities of the derivative proteins. For example, ligand-binding or other domains may be "swapped" between different new fusion polypeptides or fragments. Such homologous or heterologous fusion polypeptides may display, for example, altered strength or specificity of binding. Fusion partners include immunoglobulins, bacterial β-galactosidase, trpE, protein A, β-lactamase, alpha amylase, alcohol dehydrogenase and yeast alpha mating factor. See Godowski et al., 1988.

Fusion proteins will typically be made by either recombinant nucleic acid methods, as described below, or may be chemically synthesized. Techniques for the synthesis of polypeptides are described, for example, in Merrifield (1963).

"Protein purification" refers to various methods for the isolation of the KCNE2 polypeptides from other biological material, such as from cells transformed with recombinant nucleic acids encoding KCNE2, and are well known in the art. For example, such polypeptides may be purified by immunoaffinity chromatography employing, e.g., the antibodies provided by the present invention. Various methods of protein purification are well known in the art, and include those described in Deutscher, 1990 and Scopes, 1982.

The terms "isolated", "substantially pure", and "substantially homogeneous" are used interchangeably to describe a protein or polypeptide which has been separated from components which accompany it in its natural state. A monomeric protein is substantially pure when at least about 60 to 75% of a sample exhibits a single polypeptide sequence. A substantially pure protein will typically comprise about 60 to 90% W/W of a protein sample, more usually about 95%, and preferably will be over about 99% pure. Protein purity or homogeneity may be indicated by a number of means well known in the art, such as polyacrylamide gel electrophoresis of a protein sample, followed by visualizing a single polypeptide band upon staining the gel. For certain purposes, higher resolution may be provided by using HPLC or other means well known in the art which are utilized for purification.

A KCNE2 protein is substantially free of naturally associated components when it is separated from the native contaminants which accompany it in its natural state. Thus, a polypeptide which is chemically synthesized or synthesized in a cellular system different from the cell from which it naturally originates will be substantially free from its naturally associated components. A protein may also be rendered substantially free of naturally associated components by isolation, using protein purification techniques well known in the art.

A polypeptide produced as an expression product of an isolated and manipulated genetic sequence is an "isolated polypeptide", as used herein, even if expressed in a homologous cell type. Synthetically made forms or molecules expressed by heterologous cells are inherently isolated molecules.

"Recombinant nucleic acid" is a nucleic acid which is not naturally occurring, or which is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

"Regulatory sequences" refers to those sequences normally within 100 kb of the coding region of a locus, but they may also be more distant from the coding region, which affect the expression of the gene (including transcription of the gene, and translation, splicing, stability or the like of the messenger RNA).

"Substantial homology or similarity". A nucleic acid or fragment thereof is "substantially homologous" ("or substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95–98% of the nucleotide bases.

Identity means the degree of sequence relatedness between two polypeptide or two polynucleotides sequences as determined by the identity of the match between two strings of such sequences. Identity can be readily calculated. While there exist a number of methods to measure identity between two polynucleotide or polypeptide sequences, the term "identity" is well known to skilled artisans (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). Methods commonly employed to determine identity between two sequences include, but are not limited to those disclosed in *Guide to Huge Computers*, Martin J. Bishop, ed., Academic Press, San Diego, 1994, and Carillo, H., and Lipman, D. (1988). Preferred methods to determine identity are designed to give the largest match between the two sequences tested. Such methods are codified in computer programs. Preferred computer program methods to determine identity between two sequences include, but are not limited to, GCG program package (Devereux et al. (1984), BLASTP, BLASTN, FASTA (Altschul et al. (1990); Altschul et al. (1997)).

Alternatively, substantial homology or (similarity) exists when a nucleic acid or fragment thereof will hybridize to another nucleic acid (or a complementary strand thereof) under selective hybridization conditions, to a strand, or to its complement. Selectivity of hybridization exists when hybridization which is substantially more selective than total lack of specificity occurs. Typically, selective hybridization will occur when there is at least about 55% homology over a stretch of at least about 14 nucleotides, preferably at least about 65%, more preferably at least about 75%, and most preferably at least about 90%. See, Kanehisa, 1984. The length of homology comparison, as described, may be over longer stretches, and in certain embodiments will often be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1000 mM, typically less than 500 mM, and preferably less than 200 mM. However, the combination of parameters is much more important than the measure of any single parameter. The stringency conditions are dependent on the length of the nucleic acid and the base composition of the nucleic acid, and can be determined by techniques well known in the art. See, e.g., Wetmur and Davidson, 1968.

Probe sequences may also hybridize specifically to duplex DNA under certain conditions to form triplex or other higher order DNA complexes. The preparation of such probes and suitable hybridization conditions are well known in the art.

The terms "substantial homology" or "substantial identity", when referring to polypeptides, indicate that the polypeptide or protein in question exhibits at least about 30% identity with an entire naturally-occurring protein or a portion thereof, usually at least about 70% identity, more usually at least about 80% identity, preferably at least about 90% identity, and more preferably at least about 95% identity.

Homology, for polypeptides, is typically measured using sequence analysis software. See, e.g., the Sequence Analysis Software Package of the Genetics Computer Group, University of Wisconsin Biotechnology Center, 910 University Avenue, Madison, Wis. 53705. Protein analysis software matches similar sequences using measures of homology assigned to various substitutions, deletions and other modifications. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine.

"Substantially similar function" refers to the function of a modified nucleic acid or a modified protein, with reference to the wild-type KCNE2 nucleic acid or wild-type KCNE2 polypeptide. The modified polypeptide will be substantially homologous to the wild-type KCNE2 polypeptide and will have substantially the same function. The modified polypeptide may have an altered amino acid sequence and/or may contain modified amino acids. In addition to the similarity of function, the modified polypeptide may have other useful properties, such as a longer half-life. The similarity of function (activity) of the modified polypeptide may be substantially tie same as the activity of the wild-type KCNE2 polypeptide. Alternatively, the similarity of function (activity) of the modified polypeptide may be higher than the activity of the wild-type KCNE2 polypeptide. The modified polypeptide is synthesized using conventional techniques, or is encoded by a modified nucleic acid and produced using conventional techniques. The modified nucleic acid is prepared by conventional techniques. A nucleic acid with a function substantially similar to the wild-type KCNE2 gene function produces the modified protein described above.

A polypeptide "fragment", "portion" or "segment" is a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids.

The polypeptides of the present invention, if soluble, may be coupled to a solid-phase support, e.g., nitrocellulose, nylon, column packing materials (e.g., Sepharose beads), magnetic beads, glass wool, plastic, metal, polymer gels, cells, or other substrates. Such supports may take the form, for example, of beads, wells, dipsticks, or membranes.

"Target region" refers to a region of the nucleic acid which is amplified and/or detected. The term "target sequence" refers to a sequence with which a probe or primer will form a stable hybrid under desired conditions.

The practice of the present invention employs, unless otherwise indicated, conventional techniques of chemistry, molecular biology, microbiology, recombinant DNA, genetics, and immunology. See, e.g., Maniatis et al., 1982; Sambrook et al., 1989; Ausubel et al., 1992; Glover, 1985; Anand, 1992; Guthrie and Fink, 1991. A general discussion of techniques and materials for human gene mapping, including mapping of human chromosome 1, is provided, e.g., in White and Lalouel, 1988.

Preparation of Recombinant or Chemically Synthesized Nucleic Acids; Vectors, Transformation, Host Cells Large amounts of the polynucleotides of the present invention may be produced by replication in a suitable host cell. Natural or synthetic polynucleotide fragments coding for a desired fragment will be incorporated into recombinant polynucleotide constructs, usually DNA constructs, capable of introduction into and replication in a prokaryotic or eukaryotic cell. Usually the polynucleotide constructs will be suitable for replication in a unicellular host, such as yeast or bacteria, but may also be intended for introduction to (with and without integration within the genome) cultured mammalian or plant or other eukaryotic cell lines. The purification of nucleic acids produced by the methods of the present invention are described, e.g., in Sambrook et al., 1989 or Ausubel et al., 1992.

The polynucleotides of the present invention may also be produced by chemical synthesis, e.g., by the phosphoramidite method described by Beaucage and Caruthers (1981) or the triester method according to Matteucci and Caruthers (1981) and may be performed on commercial, automated oligonucleotide synthesizers. A double-stranded fragment may be obtained from the single-stranded product of chemical synthesis either by synthesizing the complementary strand and annealing the strand together under appropriate conditions or by adding the complementary strand using DNA polymerase with an appropriate primer sequence.

Polynucleotide constructs prepared for introduction into a prokaryotic or eukaryotic host may comprise a replication system recognized by the host, including the intended polynucleotide fragment encoding the desired polypeptide, and will preferably also include transcription and translational initiation regulatory sequences operably linked to the polypeptide encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Such vectors may be prepared by means of standard recombinant techniques well known in the art and discussed, for example, in Sambrook et al., 1989 or Ausubel et al., 1992.

An appropriate promoter and other necessary vector sequences will be selected so as to be functional in the host, and may include, when appropriate, those naturally associated with the KCNE2 gene. Examples of workable combinations of cell lines and expression vectors are described in Sambrook et al., 1989 or Ausubel et al., 1992; see also, e.g., Metzger et al., 1988. Many usefull vectors are known in the art and may be obtained from such vendors as Stratagene, New England Biolabs, Promega Biotech, and others. Promoters such as the trp, lac and phage promoters, tRNA promoters and glycolytic enzyme promoters may be used in prokaryotic hosts. Useful yeast promoters include promoter regions for metallothionein, 3-phosphoglycerate kinase or other glycolytic enzymes such as enolase or glyceraldehyde-3-phosphate dehydrogenase, enzymes responsible for maltose and galactose utilization, and others. Vectors and promoters suitable for use in yeast expression are further described in Hitzeman et al., EP 73,675A. Appropriate non-native mammalian promoters might include the early and late promoters from SV40 (Fiers et al., 1978) or promoters derived from murine Molony leukemia virus, mouse tumor virus, avian sarcoma viruses, adenovirus II, bovine papilloma virus or polyoma. Insect promoters may be derived from baculovirus. In addition, the construct may be joined to an amplifiable gene (e.g., DHFR) so that multiple copies of the gene may be made. For appropriate enhancer and other expression control sequences, see also *Enhancers and Eukaryotic Gene Expression*, Cold Spring Harbor Press, Cold Spring Harbor, N.Y. (1983). See also, e.g., U.S. Pat. Nos. 5,691,198; 5,735,500; 5,747,469 and 5,436,146.

While such expression vectors may replicate autonomously, they may also replicate by being inserted into the genome of the host cell, by methods well known in the art.

Expression and cloning vectors will likely contain a selectable marker, a gene encoding a protein necessary for survival or growth of a host cell transformed with the vector. The presence of this gene ensures growth of only those host cells which express the inserts. Typical selection genes encode proteins that a) confer resistance to antibiotics or other toxic substances, e.g. ampicillin, neomycin, methotrexate, etc., b) complement auxotrophic deficiencies, or c) supply critical nutrients not available from complex media, e.g., the gene encoding D-alanine racemase for Bacilli. The choice of the proper selectable marker will depend on the host cell, and appropriate markers for different hosts are well known in the art.

The vectors containing the nucleic acids of interest can be transcribed in vitro, and the resulting RNA introduced into the host cell by well-known methods, e.g., by injection (see, Kubo et al., 1988), or the vectors can be introduced directly into host cells by methods well known in the art, which vary depending on the type of cellular host, including electroporation; transfection employing calcium chloride, rubidium chloride calcium phosphate, DEAE-dextran, or other substances; microprojectile bombardment; lipofection; infection (where the vector is an infectious agent, such as a retroviral genome); and other methods. See generally, Sambrook et al., 1989 and Ausubel et al., 1992. The introduction of the polynucleotides into the host cell by any method known in the art, including, inter alia, those described above, will be referred to herein as "transformation." The cells into which have been introduced nucleic acids described above are meant to also include the progeny of such cells.

Large quantities of the nucleic acids and polypeptides of the present invention may be prepared by expressing the KCNE2 nucleic acid or portions thereof in vectors or other expression vehicles in compatible prokaryotic or eukaryotic host cells. The most commonly used prokaryotic hosts are strains of *Escherichia coli*, although other prokaryotes, such as *Bacillus sublilis* or Pseudomonas may also be used.

Mammalian or other eukaryotic host cells, such as those of yeast, filamentous fungi, plant, insect, or amphibian or avian species, may also be useful for production of the proteins of the present invention. Propagation of mammalian cells in culture is per se well known. See, Jakoby and Pastan (eds.) (1979). Examples of commonly used mammalian host cell lines are VERO and HeLa cells, Chinese hamster ovary (CHO) cells, and WI38, BHK, and COS cell lines, although it will be appreciated by the skilled practitioner that other cell lines may be appropriate, e.g., to provide higher expression, desirable glycosylation patterns, or other features. An example of a commonly used insect cell line is SF9.

Clones are selected by using markers depending on the mode of the vector construction. The marker may be on the same or a different DNA molecule, preferably the same DNA molecule. In prokaryotic hosts, the transformant may be selected, e.g., by resistance to ampicillin, tetracycline or other antibiotics. Production of a particular product based on temperature sensitivity may also serve as an appropriate marker.

Prokaryotic or eukaryotic cells transformed with the polynucleotides of the present invention will be useful not only for the production of the nucleic acids and polypeptides of the present invention, but also, for example, in studying the characteristics of KCNE2 polypeptides.

The probes and primers based on the KCNE2 gene sequence disclosed herein are used to identify homologous KCNE2 gene sequences and proteins in other species. These gene sequences and proteins are used in the diagnostic/prognostic, therapeutic and drug screening methods described herein for the species from which they have been isolated.

Methods of Use: Drug Screening

The invention is particularly useful for screening compounds by using KCNE2, KCNE3 or KCNE4 proteins in transformed cells, transfected oocytes or transgenic animals. Since mutations in either the KCNE2 protein can alter the functioning of the cardiac $I_{Kr}$ potassium channel, candidate drugs are screened for effects on the channel using oocytes or using cells containing either a normal KCNE2 protein and a mutant HERG protein, respectively, or a mutant HERG and a mutant KCNE2 protein. The drug is added to the cells in culture, e.g., stably transformed cells, or administered to a transgenic animal, e.g., a knockout mouse, and the effect on the induced current of the $I_{Ks}$ potassium channel is compared to the induced current of a cell or animal containing the wild-type HERG and KCNE2. Drug candidates which alter the induced current to a more normal level are useful for treating or preventing LQT. Suitable electrophysiology methods which can be used for drug screening are described in the Examples. These methods can be applied to oocytes or stably transformed cells. In this manner, the effect of drugs on voltage-gated ion channels which include KCNE2, KCNE3 or KCNE4 can be determined.

This invention is particularly useful for screening compounds by using the KCNE2 polypeptide or binding fragment thereof in any of a variety of drug screening techniques.

The KCNE2 polypeptide or fragment employed in such a test may either be free in solution, affixed to a solid support, or borne on a cell surface. One method of drug screening utilizes eucaryotic or procaryotic host cells which are stably transformed with recombinant polynucleotides expressing the polypeptide or fragment, preferably in competitive binding assays. Such cells, either in viable or fixed form, can be used for standard binding assays. One may measure, for example, for the formation of complexes between a KCNE2 polypeptide or fragment and the agent being tested, or examine the degree to which the formation of a complex between a KCNE2 polypeptide or fragment and a known ligand is interfered with by the agent being tested.

Thus, the present invention provides methods of screening for drugs comprising contacting such an agent with a KCNE2 polypeptide or fragment thereof and assaying (i) for the presence of a complex between the agent and the KCNE2 polypeptide or fragment, or (ii) for the presence of a complex between the KCNE2 polypeptide or fragment and a ligand, by methods well known in the art. In such competitive binding assays the KCNE2 polypeptide or fragment is typically labeled. Free KCNE2 polypeptide or fragment is separated from that present in a protein:protein complex, and the amount of free (i.e., uncomplexed) label is a measure of the binding of the agent being tested to KCNE2 or its interference with KCNE2:ligand binding, respectively. One may also measure the amount of bound, rather than free, KCNE2. It is also possible to label the ligand rather than the KCNE2 and to measure the amount of ligand binding to KCNE2 in the presence and in the absence of the drug being tested.

Another technique for drug screening provides high throughput screening for compounds having suitable binding affinity to the KCNE2 polypeptides and is described in detail in Geysen (published PCT application WO 84/03564). Briefly stated, large numbers of different small peptide test compounds are synthesized on a solid substrate, such as plastic pins or some other surface. The peptide test compounds are reacted with KCNE2 polypeptide and washed. Bound KCNE2 polypeptide is then detected by methods well known in the art.

Purified KCNE2 can be coated directly onto plates for use in the aforementioned drug screening techniques. However, non-neutralizing antibodies to the polypeptide can be used to capture antibodies to immobilize the KCNE2 polypeptide on the solid phase.

This invention also contemplates the use of competitive drug screening assays in which neutralizing antibodies capable of specifically binding the KCNE2 polypeptide compete with a test compound for binding to the KCNE2 polypeptide or fragments thereof In this manner, the antibodies can be used to detect the presence of any peptide which shares one or more antigenic determinants of the KCNE2 polypeptide.

The above screening methods are not limited to assays employing only KCNE2 but are also applicable to studying KCNE2-protein complexes. The effect of drugs on the activity of this complex is analyzed.

In accordance with these methods, the following assays are examples of assays which can be used for screening for drug candidates.

A mutant KCNE2 (per se or as part of a fusion protein) is mixed with a wild-type protein (per se or as part of a fusion protein) to which wild-type KCNE2 binds. This mixing is performed in both the presence of a drug and the absence of the drug, and the amount of binding of the mutant KCNE2 with the wild-type protein is measured. If the amount of the binding is more in the presence of said drug than in the absence of said drug, the drug is a drug candidate for treating LQT resulting from a mutation in KCNE2.

A wild-type KCNE2 (per se or as part of a fusion protein) is mixed with a wild-type protein (per se or as part of a fusion protein) to which wild-type KCNE2 binds. This mixing is performed in both the presence of a drug and the absence of the drug, and the amount of binding of the wild-type KCNE2 with the wild-type protein is measured. If the amount of the binding is more in the presence of said drug than in the absence of said drug, the drug is a drug candidate for treating LQT resulting from a mutation in KCNE2.

A mutant protein, which as a wild-type protein binds to KCNE2 (per se or as part of a fusion protein) is mixed with a wild-type KCNE2 (per se or as part of a fusion protein). This mixing is performed in both the presence of a drug and the absence of the drug, and the amount of binding of the mutant protein with the wild-type KCNE2 is measured. If the amount of the binding is more in the presence of said drug than in the absence of said drug, the drug is a drug candidate for treating LQT resulting from a mutation in the gene encoding the protein.

Methods of Use: Pharmacogenomics

The KCNE2 molecules (as well as KCNE3 and KCNE4 molecules) of the present invention, as well as agents, or modulators which have a stimulatory or inhibitory effect on KCNE2 activity (e.g., KCNE2 gene expression) as identified by a screening assay described herein can be administered to individuals to treat (prophylactically or therapeutically) disorders associated with aberrant KCNE2 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a KCNE2 molecule or KCNE2 modulator as well as tailoring the dosage and/or therapeutic regimen of treatment with a KCNE2 molecule or KCNE2 modulator.

Pharmacogenomics deals with clinically significant hereditary variations in the response to drugs due to altered drug disposition and abnormal action in affected persons. See, for example, Eichelbaum et al. (1996) and Linder et al. (1997). In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as commonly-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict a drug response. According to this method, if a gene that encodes a drug target is known (e.g., a KCNE2 protein or KCNE2 receptor of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C 19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification. Similar analysis with the MinK-related peptides correlates genotype and drug effects.

Alternatively, a method termed the "gene expression profiling", can be utilized to identify genes that predict drug response. For example, the gene expression of an animal dosed with a drug (e.g., a KCNE2 molecule or KCNE2 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a KCNE2 molecule or KCNE2 modulator, such as a modulator identified by one of the exemplary screening assays described herein.

Methods of Use: Rational Drug Design

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. Several approaches for use in rational drug design include analysis of three-dimensional structure, alanine scans, molecular modeling and use of anti-id antibodies. These techniques are well known to those skilled in the art, including those described in U.S. Pat. Nos. 5,837,492; 5,800,998 and 5,891,628, each incorporated herein by reference.

Thus, one may design drugs which have, e.g., improved KCNE2 polypeptide activity or stability or which act as inhibitors, agonists, antagonists, etc. of KCNE2 polypeptide activity. By virtue of the availability of cloned KCNE2 sequences, sufficient amounts of the KCNE2 polypeptide may be made available to perform such analytical studies as x-ray crystallography. In addition, the knowledge of the KCNE2 protein sequences provided herein will guide those employing computer modeling techniques in place of, or in addition to x-ray crystallography.

The polypeptide of the invention may also be used for screening compounds developed as a result of combinatorial library technology. Combinatorial library technology provides an efficient way of testing a potential vast number of different substances for ability to modulate activity of a polypeptide. Such libraries and their use are known in the art. The use of peptide libraries is preferred. See, for example, WO 97/02048.

Briefly, a method of screening for a substance which modulates activity of a polypeptide may include contacting one or more test substances with the polypeptide in a suitable reaction medium, testing the activity of the treated polypeptide and comparing that activity with the activity of the polypeptide in comparable reaction medium untreated with the test substance or substances. A difference in activity between the treated and untreated polypeptides is indicative of a modulating effect of the relevant test substance or substances.

Prior to, or as well as being screened for modulation of activity, test substances may be screened for ability to interact with the polypeptide, e.g., in a yeast two-hybrid system (e.g., Bartel et al., 1993; Fields and Song, 1989; Chevray and Nathans, 1992; Lee et al., 1995). This system may be used as a coarse screen prior to testing a substance for actual ability to modulate activity of the polypeptide. Alternatively, the screen could be used to screen test substances for binding to an KCNE2 specific binding partner, or to find mimetics of the KCNE2 polypeptide.

Following identification of a substance which modulates or affects polypeptide activity, the substance may be further investigated. Furthermore, it may be manufactured and/or used in preparation, i.e., manufacture or formulation, or a composition such as a medicament, pharmaceutical composition or drug. These may be administered to individuals.

Thus, the present invention extends in various aspects not only to a substance identified using a nucleic acid molecule as a modulator of polypeptide activity, in accordance with what is disclosed herein, but also a pharmaceutical composition, medicament, drug or other composition comprising such a substance, a method comprising administration of such a composition comprising such a substance, a method comprising administration of such a composition to a patient, e.g., for treatment (which may include preventative treatment) of LQT, use of such a substance in the manufacture of a composition for administration, e.g., for treatment of LQT, and a method of making a pharmaceutical composition comprising admixing such a substance with a pharmaceutically acceptable excipient, vehicle or carrier, and optionally other ingredients.

A substance identified as a modulator of polypeptide function may be peptide or non-peptide in nature. Non-peptide "small molecules" are often preferred for many in vivo pharmaceutical uses. Accordingly, a mimetic or mimic of the substance (particularly if a peptide) may be designed for pharmaceutical use.

The designing of mimetics to a known pharmaceutically active compound is a known approach to the development of pharmaceuticals based on a "lead" compound. This might be desirable where the active compound is difficult or expensive to synthesize or where it is unsuitable for a particular method of administration, e.g., pure peptides are unsuitable active agents for oral compositions as they tend to be quickly degraded by proteases in the alimentary canal. Mimetic design, synthesis and testing is generally used to avoid randomly screening large numbers of molecules for a target property.

There are several steps commonly taken in the design of a mimetic from a compound having a given target property. First, the particular parts of the compound that are critical and/or important in determining the target property are determined. In the case of a peptide, this can be done by systematically varying the amino acid residues in the peptide, e.g., by substituting each residue in turn. Alanine scans of peptide are commonly used to refine such peptide motifs. These parts or residues constituting the active region of the compound are known as its "pharmacophore".

Once the pharmacophore has been found, its structure is modeled according to its physical properties, e.g., stereochemistry, bonding, size and/or charge, using data from a range of sources, e.g., spectroscopic techniques, x-ray diffraction data and NMR. Computational analysis, similarity mapping (which models the charge and/or volume of a pharmacophore, rather than the bonding between atoms) and other techniques can be used in this modeling process.

In a variant of this approach, the three-dimensional structure of the ligand and its binding partner are modeled. This can be especially useful where the ligand and/or binding partner change conformation on binding, allowing the model to take account of this in the design of the mimetic.

A template molecule is then selected onto which chemical groups which mimic the pharmacophore can be grafted. The template molecule and the chemical groups grafted onto it can conveniently be selected so that the mimetic is easy to synthesize, is likely to be pharmacologically acceptable, and does not degrade in vivo, while retaining the biological activity of the lead compound. Alternatively, where the mimetic is peptide-based, further stability can be achieved by cyclizing the peptide, increasing its rigidity. The mimetic or mimetics found by this approach can then be screened to see whether they have the target property, or to what extent they exhibit it. Further optimization or modification can then be carried out to arrive at one or more final mimetics for in vivo or clinical testing.

Methods of Use: Nucleic Acid Diagnosis and Diagnostic Kits

In order to detect the presence of a KCNE2 allele predisposing an individual to LQT, a biological sample such as blood is prepared and analyzed for the presence or absence of susceptibility alleles of KCNE2. In order to detect the presence of LQT or as a prognostic indicator, a biological sample is prepared and analyzed for the presence or absence of mutant alleles of KCNE2. Results of these tests and interpretive information are returned to the health care provider for communication to the tested individual. Such diagnoses may be performed by diagnostic laboratories, or, alternatively, diagnostic kits are manufactured and sold to health care providers or to private individuals for self-diagnosis.

Initially, the screening method involves amplification of the relevant KCNE2 sequences. In another preferred embodiment of the invention, the screening method involves a non-PCR based strategy. Such screening methods include two-step label amplification methodologies that are well known in the art. Both PCR and non-PCR based screening strategies can detect target sequences with a high level of sensitivity.

The most popular method used today is target amplification. Here, the target nucleic acid sequence is amplified with polymerases. One particularly preferred method using polymerase-driven amplification is the polymerase chain reaction (PCR). The polymerase chain reaction and other polymerase-driven amplification assays can achieve over a million-fold increase in copy number through the use of polymerase-driven amplification cycles. Once amplified, the resulting nucleic acid can be sequenced or used as a substrate for DNA probes.

When the probes are used to detect the presence of the target sequences the biological sample to be analyzed, such as blood or serum, may be treated, if desired, to extract the nucleic acids. The sample nucleic acid may be prepared in various ways to facilitate detection of the target sequence, e.g. denaturation, restriction digestion, electrophoresis or dot blotting. The targeted region of the analyte nucleic acid usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Analyte nucleic acid and probe are incubated under conditions which promote stable hybrid formation of the target sequence in the probe with the putative targeted sequence in the analyte. The region of the probes which is used to bind to the analyte can be made completely complementary to the targeted region of KCNE2. Therefore, high stringency conditions are desirable in order to prevent false positives. However, conditions of high stringency are used only if the probes are complementary to regions of the chromosome which are unique in the genome. The stringency of hybridization is determined by a number of factors during hybridization and during the washing procedure, including temperature, ionic strength, base composition, probe length, and concentration of formamide. These factors are outlined in, for example, Maniatis et al., 1982 and Sambrook et al., 1989. Under certain circumstances, the formation of higher order hybrids, such as triplexes, quadraplexes, etc., may be desired to provide the means of detecting target sequences.

Detection, if any, of the resulting hybrid is usually accomplished by the use of labeled probes. Alternatively, the probe may be unlabeled, but may be detectable by specific binding with a ligand which is labeled, either directly or indirectly.

Suitable labels, and methods for labeling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies, gold nanoparticles and the like. Variations of this basic scheme are known in the art, and include those variations that facilitate separation of the hybrids to be detected from extraneous materials and/or that amplify the signal from the labeled moiety. A number of these variations are reviewed in, e.g., Matthews and Kricka, 1988; Landegren et al., 1988; Mifflin, 1989; U.S. Pat. No. 4,868,105; and in EPO Publication No. 225,807.

As noted above, non-PCR based screening assays are also contemplated in this invention. This procedure hybridizes a nucleic acid probe (or an analog such as a methyl phosphonate backbone replacing the normal phosphodiester), to the low level DNA target. This probe may have an enzyme covalently linked to the probe, such that the covalent linkage does not interfere with the specificity of the hybridization. This enzyme-probe-conjugate-target nucleic acid complex can then be isolated away from the free probe enzyme conjugate and a substrate is added for enzyme detection. Enzymatic activity is observed as a change in color development or luminescent output resulting in a $10^3$–$10^6$ increase in sensitivity. For an example relating to the preparation of oligodeoxynucleotide-alkaline phosphatase conjugates and their use as hybridization probes, see Jablonski et al. (1986).

Two-step label amplification methodologies are known in the art. These assays work on the principle that a small ligand (such as digoxigenin, biotin, or the like) is attached to a nucleic acid probe capable of specifically binding KCNE2. Allele specific probes are also contemplated within the scope of this example and exemplary allele specific probes include probes encompassing the predisposing mutations of this patent application.

In one example, the small ligand attached to the nucleic acid probe is specifically recognized by an antibody-enzyme conjugate. In one embodiment of this example, digoxigenin is attached to the nucleic acid probe. Hybridization is detected by an antibody-alkaline phosphatase coijugate which turns over a chemiluminescent substrate. For methods for labeling nucleic acid probes according to this embodiment see Martinet al., 1990. In a second example, the small ligand is recognized by a second ligand-enzyme conjugate that is capable of specifically complexing to the first ligand. A well known embodiment of this example is the biotin-avidin type of interactions. For methods for labeling nucleic acid probes and their use in biotin-avidin based assays see Rigby et al., 1977 and Nguyen et al., 1992.

It is also contemplated within the scope of this invention that the nucleic acid probe assays of this invention will employ a cocktail of nucleic acid probes capable of detecting KCNE2. Thus, in one example to detect the presence of KCNE2 in a cell sample, more than one probe complementary to the gene is employed and in particular, the number of different probes is alternatively two, three, or five different nucleic acid probe sequences. In another example, to detect the presence of mutations in the KCNE2 gene sequence in a patient, more than one probe complementary to these genes is employed where the cocktail includes probes capable of binding to the allele-specific mutations identified in populations of patients with alterations in KCNE2. In this embodiment, any number of probes can be used, and will preferably include probes corresponding to the major gene mutations identified as predisposing an individual to LQT.

Methods of Use: Peptide Diagnosis and Diagnostic Kits

The presence of LQT can also be detected on the basis of the alteration of wild-type KCNE2 polypeptide. Such alterations can be determined by sequence analysis in accordance with conventional techniques. More preferably, antibodies (polyclonal or monoclonal) are used to detect differences in, or the absence of KCNE2 peptides. Techniques for raising and purifying antibodies are well known in the art, and any such techniques may be chosen to achieve the preparations claimed in this invention. In a preferred embodiment of the invention, antibodies will immunoprecipitate KCNE2 proteins from solution as well as react with these proteins on Western or immunoblots of polyacrylamide gels. In another preferred embodiment, antibodies will detect KCNE2 proteins in paraffin or frozen tissue sections, using immunocytochemical techniques.

Preferred embodiments relating to methods for detecting KCNE2 or its mutations include enzyme linked immunosorbent assays (ELISA), radioimmunoassays (RIA), immunoradiometric assays (IRMA) and immunoenzymatic assays (IEMA), including sandwich assays using monoclonal and/or polyclonal antibodies. Exemplary sandwich assays are described by David et al., in U.S. Pat. Nos. 4,376,110 and 4,486,530, hereby incorporated by reference.

Methods of Use: Gene Therapy

According to the present invention, a method is also provided of supplying wild-type KCNE2 function to a cell which carries a mutant KCNE2 allele, respectively. Supplying such a function should allow normal functioning of the recipient cells. The wild-type gene or a part of the gene may be introduced into the cell in a vector such that the gene remains extrachromosomal. In such a situation, the gene will be expressed by the cell from the extrachromosomal location. More preferred is the situation where the wild-type gene or a part thereof is introduced into the mutant cell in such a way that it recombines with the endogenous mutant gene present in the cell. Such recombination requires a double recombination event which results in the correction of the gene mutation. Vectors for introduction of genes both for recombination and for extrachromosomal maintenance are known in the art, and any suitable vector may be used. Methods for introducing DNA into cells such as electroporation, calcium phosphate co-precipitation and viral transduction are known in the art, and the choice of method is within the competence of the practitioner.

As generally discussed above, the KCNE2 gene or fragment, where applicable, may be employed in gene therapy methods in order to increase the amount of the expression products of such gene in cells. It may also be useful to increase the level of expression of a given LQT gene even in those heart cells in which the mutant gene is expressed at a "normal" level, but the gene product is not fully functional.

Gene therapy would be carried out according to generally accepted methods, for example, as described by Friedman (1991) or Culver (1996). Cells from a patient would be first analyzed by the diagnostic methods described above, to ascertain the production of KCNE2 polypeptide in the cells. A virus or plasmid vector (see further details below), containing a copy of the KCNE2 gene linked to expression control elements and capable of replicating inside the cells, is prepared. The vector may be capable of replicating inside the cells. Alternatively, the vector may be replication deficient and is replicated in helper cells for use in gene therapy. Suitable vectors are known, such as disclosed in U.S. Pat. No. 5,252,479 and PCT published application WO 93/07282 and U.S. Pat. Nos. 5,691,198; 5,747,469; 5,436,146 and 5,753,500. The vector is then injected into the patient. If the transfected gene is not permanently incorporated into the genome of each of the targeted cells, the treatment may have to be repeated periodically.

Gene transfer systems known in the art may be useful in the practice of the gene therapy methods of the present invention. These include viral and nonviral transfer methods. A number of viruses have been used as gene transfer vectors or as the basis for repairing gene transfer vectors, including papovaviruses (e.g., SV40, Madzak et al., 1992), adenovirus (Berkner, 1992; Berkner et al., 1988; Gorziglia and Kapikian, 1992; Quantin et al., 1992; Rosenfeld et al., 1992; Wilkinson and Akrigg, 1992; Stratford-Perricaudet et al., 1990; Schneider et al., 1998), vaccinia virus (Moss, 1992; Moss, 1996), adeno-associated virus (Muzyczka, 1992; Ohi et al., 1990; Russell and Hirata, 1998), herpesviruses including HSV and EBV (Margolskee, 1992; Johnson et al., 1992; Fink et al., 1992; Breakefield and Geller, 1987; Freese et al., 1990; Fink et al., 1996), lentiviruses (Naldini et al., 1996), Sindbis and Semliki Forest virus (Berglund et al., 1993), and retroviruses of avian (Bandyopadhyay and Temin, 1984; Petropoulos et al., 1992), murine (Miller, 1992; Miller et al., 1985; Sorge et al., 1984; Mann and Baltimore, 1985; Miller et al., 1988), and human origin (Shimada et al., 1991; Helseth et al., 1990; Page et al., 1990; Buchschacher and Panganiban, 1992). Most human gene therapy protocols have been based on disabled murine retroviruses, although adenovirus and adeno-associated virus are also being used.

Nonviral gene transfer methods known in the art include chemical techniques such as calcium phosphate coprecipitation (Graham and van der Eb, 1973; Pellicer et al., 1980); mechanical techniques, for example microinjection (Anderson et al., 1980; Gordon et al., 1980; Brinster et al., 1981; Costantini and Lacy, 1981); membrane fusion-mediated transfer via liposomes (Feigner et al., 1987; Wang and Huang, 1989; Kaneda et al., 1989; Stewart et al., 1992; Nabel et al., 1990; Lim et al., 1991); and direct DNA uptake and receptor-mediated DNA transfer (Wolff et al., 1990; Wu et al., 1991; Zenke et al., 1990; Wu et al., 1989; Wolff et al., 1991; Wagner et al., 1990; Wagner et al., 1991; Cotten et al., 1990; Curiel et al., 1992; Curiel et al., 1991). Viral-mediated gene transfer can be combined with direct in vivo gene transfer using liposome delivery, allowing one to direct the viral vectors to the tumor cells and not into the surrounding nondividing cells. Alternatively, the retroviral vector producer cell line can be injected into tumors (Culver et al., 1992). Injection of producer cells would then provide a continuous source of vector particles. This technique has been approved for use in humans with inoperable brain tumors.

In an approach which combines biological and physical gene transfer methods, plasmid DNA of any size is combined with a polylysine-conjugated antibody specific to the adenovirus hexon protein, and the resulting complex is bound to an adenovirus vector. The trimolecular complex is then used to infect cells. The adenovirus vector permits efficient binding, internalization, and degradation of the endosome before the coupled DNA is damaged. For other techniques for the delivery of adenovirus based vectors see Schneider et al. (1998) and U.S. Pat. Nos. 5,691,198; 5,747,469; 5,436,146 and 5,753,500.

Liposome/DNA complexes have been shown to be capable of mediating direct in vivo gene transfer. While in standard liposome preparations the gene transfer process is nonspecific, localized in vivo uptake and expression have been reported in tumor deposits, for example, following direct in situ administration (Nabel, 1992).

Expression vectors in the context of gene therapy are meant to include those constructs containing sequences sufficient to express a polynucleotide that has been cloned therein. In viral expression vectors, the construct contains viral sequences sufficient to support packaging of the construct. If the polynucleotide encodes KCNE2, expression will produce KCNE2. If the polynucleotide encodes an antisense polynucleotide or a ribozyme, expression will produce the antisense polynucleotide or ribozyme. Thus in this context, expression does not require that a protein product be synthesized. In addition to the polynucleotide cloned into the expression vector, the vector also contains a promoter functional in eukaryotic cells. The cloned polynucleotide sequence is under control of this promoter. Suitable eukaryotic promoters include those described above. The expression vector may also include sequences, such as selectable markers and other sequences described herein.

Gene transfer techniques which target DNA directly to heart tissue is preferred. Receptor-mediated gene transfer, for example, is accomplished by the conjugation of DNA (usually in the form of covalently closed supercoiled plasmid) to a protein ligand via polylysine. Ligands are chosen on the basis of the presence of the corresponding ligand receptors on the cell surface of the target cell/tissue type. These ligand-DNA conjugates can be injected directly into the blood if desired and are directed to the target tissue where receptor binding and internalization of the DNA-protein complex occurs. To overcome the problem of intracellular destruction of DNA, coinfection with adenovirus can be included to disrupt endosome function.

The therapy is as follows: patients who carry a KCNE2 susceptibility allele are treated with a gene delivery vehicle such that some or all of their heart precursor cells receive at least one additional copy of a functional normal KCNE2 allele. In this step, the treated individuals have reduced risk of LQT to the extent that the effect of the susceptible allele has been countered by the presence of the normal allele.

Methods of Use: Peptide Therapy

Peptides which have KCNE2 activity can be supplied to cells which carry a mutant or missing KCNE2 allele. Protein can be produced by expression of the cDNA sequence in bacteria, for example, using known expression vectors. Alternatively, KCNE2 polypeptide can be extracted from KCNE2-producing mammalian cells. In addition, the techniques of synthetic chemistry can be employed to synthesize KCNE2 protein. Any of such techniques can provide the preparation of the present invention which comprises the KCNE2 protein. The preparation is substantially free of other human proteins. This is most readily accomplished by synthesis in a microorganism or in vitro.

Active KCNE2 molecules can be introduced into cells by microinjection or by use of liposomes, for example. Alternatively, some active molecules may be taken up by cells, actively or by diffusion. Supply of molecules with KCNE2 activity should lead to partial reversal of LQT. Other molecules with KCNE2 activity (for example, peptides, drugs or organic compounds) may also be used to effect such a reversal. Modified polypeptides having substantially similar function are also used for peptide therapy.

Methods of Use: Transformed Hosts

Animals for testing therapeutic agents can be selected after mutagenesis of whole animals or after treatment of germline cells or zygotes. Such treatments include insertion of mutant KCNE2 alleles, usually from a second animal species, as well as insertion of disrupted homologous genes. Alternatively, the endogenous KCNE2 gene of the animals may be disrupted by insertion or deletion mutation or other genetic alterations using conventional techniques (Capecchi, 1989; Valancius and Smithies, 1991; Hasty et al., 1991; Shinkai et al., 1992; Mombaerts et al., 1992; Philpott et al., 1992; Snouwaert et al., 1992; Donehower et al., 1992). These transgenic, transplacement and knock-out animals, particularly knockout mice, can also be used to screen drugs that may be useful for treating or preventing LQT or other ion channel disorders or to screen drugs for their effect on ion channel activity. Cell lines can also be derived from these animals for use as cellular models, or in drug screening. After test substances have been administered to the animals, the presence of LQT must be assessed. If the test substance prevents or suppresses the appearance of LQT, then the test substance is a candidate therapeutic agent for treatment of LQT. These animal models provide an extremely important testing vehicle for potential therapeutic products. Conventional methods are employed, including those described in U.S. Pat. Nos. 5,837,492; 5,800,998 and 5,891,628, each incorporated herein by reference.

Presymptomatic diagnosis of LQT has depended on identification of QT prolongation on electrocardiograms. Unfortunately, electrocardiograms are rarely performed in young, healthy individuals. In addition, many LQT gene carriers have relatively normal QT intervals, and the first sign of disease can be a fatal cardiac arrhythmia (Vincent et al., 1992). Now that more LQT genes have been identified and have been associated with LQT, genetic testing for this disorder can be contemplated. This will require continued mutational analyses and identification of additional LQT genes. With more detailed phenotypic analyses, phenotypic differences between the varied forms of LQT may be discovered. These differences may be useful for diagnosis and treatment.

The identification of the association between the KCNE2 gene mutations and LQT permits the early presymptomatic screening of individuals to identify those at risk for developing LQT. To identify such individuals, the KCNE2 alleles are screened for mutations either directly or after cloning the alleles. The alleles are tested for the presence of nucleic acid sequence differences from the normal allele using any suitable technique, including but not limited to, one of the following methods: fluorescent in situ hybridization (FISH), direct DNA sequencing, PFGE analysis, Southern blot analysis, single stranded conformation analysis (SSCP), linkage analysis, RNase protection assay, allele specific oligonucleotide (ASO), dot blot analysis and PCR-SSCP analysis. Also useful is the recently developed technique of DNA microchip technology. For example, either (1) the nucleotide sequence of both the cloned alleles and normal KCNE2 gene or appropriate fragment (coding sequence or genomic sequence) are determined and then compared, or (2) the RNA transcripts of the KCNE2 gene or gene fragment are hybridized to single stranded whole genomic DNA from an individual to be tested, and the resulting heteroduplex is treated with Ribonuclease A (RNase A) and run on a denaturing gel to detect the location of any mismatches. Two of these methods can be carried out according to the following procedures.

The alleles of the KCNE2 gene in an individual to be tested are cloned using conventional techniques. For example, a blood sample is obtained from the individual. The genomic DNA isolated from the cells in this sample is partially digested to an average fragment size of approximately 20 kb. Fragments in the range from 18–21 kb are isolated. The resulting fragments are ligated into an appropriate vector. The sequences of the clones are then determined and compared to the normal KCNE2 gene.

Alternatively, polymerase chain reactions (PCRs) are performed with primer pairs for the 5' region or the exons of the KCNE2 gene. PCRs can also be performed with primer pairs based on any sequence of the normal KCNE2 gene. For example, primer pairs for one of the introns can be prepared and utilized. Finally, RT-PCR can also be performed on the mRNA. The amplified products are then analyzed by single stranded conformation polymorphisms (SSCP) using conventional techniques to identify any differences and these are then sequenced and compared to the normal gene sequence.

Individuals can be quickly screened for common KCNE2 gene variants by amplifying the individual's DNA using suitable primer pairs and analyzing the amplified product, e.g., by dot-blot hybridization using allele-specific oligonucleotide probes.

The second method employs RNase A to assist in the detection of differences between the normal KCNE2 gene and defective genes. This comparison is performed in steps using small (~500 bp) restriction fragments of the KCNE2 gene as the probe. First, the KCNE2 gene is digested with a restriction enzyme(s) that cuts the gene sequence into fragments of approximately 500 bp. These fragments are separated on an electrophoresis gel, purified from the gel and cloned individually, in both orientations, into an SP6 vector (e.g., pSP64 or pSP65). The SP6-based plasmids containing inserts of the KCNE2 gene fragments are transcribed in vitro using the SP6 transcription system, well known in the art, in the presence of $[\alpha-^{32}P]GTP$, generating radiolabeled RNA transcripts of both strands of the gene.

Individually, these RNA transcripts are used to form heteroduplexes with the allelic DNA using conventional techniques. Mismatches that occur in the RNA:DNA heteroduplex, owing to sequence differences between the KCNE2 fragment and the KCNE2 allele subclone from the individual, result in cleavage in the RNA strand when treated with RNase A. Such mismatches can be the result of point mutations or small deletions in the individual's allele. Cleavage of the RNA strand yields two or more small RNA fragments, which run faster on the denaturing gel than the RNA probe itself.

Any differences which are found, will identify an individual as having a molecular variant of the KCNE2 gene and the consequent presence of long QT syndrome. These variants can take a number of forms. The most severe forms would be frame shift mutations or large deletions which would cause the gene to code for an abnormal protein or one which would significantly alter protein expression. Less severe disruptive mutations would include small in-frame deletions and nonconservative base pair substitutions which would have a significant effect on the protein produced, such as changes to or from a cysteine residue, from a basic to an acidic amino acid or vice versa, from a hydrophobic to hydrophilic amino acid or vice versa, or other mutations which would affect secondary or tertiary protein structure. Silent mutations or those resulting in conservative amino acid substitutions would not generally be expected to disrupt protein function.

Genetic testing will enable practitioners to identify individuals at risk for LQT at, or even before, birth. Presymptomatic diagnosis of LQT will enable prevention of these disorders. Existing medical therapies, including beta adrenergic blocking agents, may prevent and delay the onset of problems associated with the disease. Finally, this invention changes our understanding of the cause and treatment of common heart disease like cardiac arrhythmias which account for 11% of all natural deaths. Existing diagnosis has focused on measuring the QT interval from electrocardiograms. This method is not a fully accurate indicator of the presence of long QT syndrome. The present invention is a more accurate indicator of the presence of the disease. Genetic testing and improved mechanistic understanding of LQT provide the opportunity for prevention of life-threatening arrhythmias through rational therapies. It is possible, for example, that potassium channel opening agents will reduce the risk of arrhythmias in patients with KCNE2 mutations; sodium channel blocking agents, by contrast, may be a more effective treatment for patients with mutations that alter the function of SCN5A. Finally, these studies may provide insight into mechanisms underlying common arrhythmias, as these arrhythmias are often associated with abnormal cardiac repolarization and may result from a combination of inherited and acquired factors.

Pharmaceutical Compositions and Routes of Administration

The KCNE2 polypeptides, antibodies, peptides and nucleic acids of the present invention can be formulated in pharmaceutical compositions, which are prepared according to conventional pharmaceutical compounding techniques. See, for example, *Remington's Pharmaceutical Sciences*, 18th Ed. (1990, Mack Publishing Co., Easton, Pa.). The composition may contain the active agent or pharmaceutically acceptable salts of the active agent. These compositions may comprise, in addition to one of the active substances, a pharmaceutically acceptable excipient, carrier, buffer, stabilizer or other materials well known in the art. Such materials should be non-toxic and should not interfere with the efficacy of the active ingredient. The carrier may take a wide variety of forms depending on the form of preparation desired for administration, e.g., intravenous, oral, intrathecal, epineural or parenteral.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698.

For parenteral administration, the compound may be dissolved in a pharmaceutical carrier and administered as either a solution or a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

The active agent is preferably administered in a therapeutically effective amount. The actual amount administered, and the rate and time-course of administration, will depend on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in Remington's Pharmaceutical Sciences.

Alternatively, targeting therapies may be used to deliver the active agent more specifically to certain types of cell, by the use of targeting systems such as antibodies or cell specific ligands. Targeting may be desirable for a variety of reasons, e.g. if the agent is unacceptably toxic, or if it would otherwise require too high a dosage, or if it would not otherwise be able to enter the target cells.

Instead of administering these agents directly, they could be produced in the target cell, e.g. in a viral vector such as described above or in a cell based delivery system such as described in U.S. Pat. No. 5,550,050 and published PCT application Nos. WO 92/19195, WO 94/25503, WO 95/01203, WO 95/05452, WO 96/02286, WO 96/02646, WO 96/40871, WO 96/40959 and WO 97/12635, designed for implantation in a patient. The vector could be targeted to the specific cells to be treated, or it could contain regulatory elements which are more tissue specific to the target cells. The cell based delivery system is designed to be implanted in a patient's body at the desired target site and contains a coding sequence for the active agent. Alternatively, the agent could be administered in a precursor form for conversion to the active form by an activating agent produced in, or targeted to, the cells to be treated. See for example, EP 425,731 A and WO 90/07936.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982; Sambrook et al., 1989; Ausubel et al., 1992; Glover, 1985; Anand, 1992; Guthrie and Fink, 1991; Harlow and Lane, 1988; Jakoby and Pastan, 1979; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I–IV (D. M. Weir and C. C. Blackwell, eds., 1986); Hogan et al., Manipulating the Mouse Embryo, (Cold Spring Harbor Laboratory Press, Cold Spring Harbor, N.Y., 1986).

Methods of Polymorphism Analysis

Single base extension methods are described by, e.g., U.S. Pat. Nos. 5,846,710; 6,004,744; 5,888,819 and 5,856,092. In brief, the methods work by hybridizing a primer that is complementary to a target sequence such that the 3' end of the primer is immediately adjacent to but does not span a site of potential variation in the target sequence. That is, the primer comprises a subsequence from the complement of a target polynucleotide terminating at the base that is immediately adjacent and 5' to the polymorphic site. The hybridization is performed in the presence of one or more labeled nucleotides complementary to base(s) that may occupy the site of potential variation. For example, for a biallelic polymorphism two differentially labeled nucleotides can be used. For a tetraallelic polymorphism four differentially labeled nucleotides can be used. In some methods, particularly methods employing multiple differentially labeled nucleotides, the nucleotides are dideoxynucleotides. Hybridization is performed under conditions permitting primer extension if a nucleotide complementary to a base occupying the site of variatioin in the target sequence is present. Extension incorporates a labeled nucleotide thereby generating a labeled extended primer. If multiple differentially labeled nucleotides are used and the target is heterozygous then multiple differentially labeled extended primers can be obtained. Extended primers are detected providing an indication of which base(s) occupy the site of variation in the target polynucleotide.

EXAMPLES

The present invention is further detailed in the following examples, which are offered by way of illustration and are not intended to limit the invention in any manner. Standard techniques well known in the art or the techniques specifically described below are utilized.

Example 1

Molecular Biology Methods

All cRNAs were synthesized after the genes were ligated into pBF2 with a modified MCS (pGA1) (Sesti and Goldstein, 1998). We searched the NCBI databases with the protein sequence encoded by KCNE1 using BLAST algorithms (Altschul et al., 1990) and failed to find significantly homologous genes. A reevaluation of sequences below the threshold for statistical significance identified 9 ESTs carrying a short target motif. Target amino acids in rat MinK were sites known to influence $I_{Ks}$ channel gating (T59, 162, R68, S69, K71, S75, D77) (Takumi et al., 1991; Splawski et al., 1997), ion selectivity (F55, T59) (Goldstein and Miller, 1991; Tai and Goldstein, 1998), unitary conductance (S75, D77) (Sesti and Goldstein, 1998) pore blockade (Y47,148, F55, G56, F57) (Goldstein and Miller, 1991; Wang et al., 1996; Tai and Goldstein, 1998) and those that gain exposure in the deep $I_{Ks}$ channel conduction pathway (F55, G56, F57, T59) (Wang et al., 1996; Tai and Goldstein, 1998). The rat and human sequences encoding MiRP 1 were first isolated by reverse transcription from cardiac poly(A)$^+$ mRNA (Clontech). Rapid amplification of cDNA ends was performed with a Marathon™ cDNA Kit and random and oligo(dT)-primed adult human heart and adult rat cDNA libraries screened (Clontech) to determine complete sequences. Three cDNAs for rat and human MiRP1 were isolated and sequenced on both strands. Analyses of nucleotide and protein sequences were performed with LaserGene (DNASTAR, Inc., Madison, Wis.). Alignments performed with ClustalW 1.6 with Blossum algorithms and gap opening and extension penalties of 15 and 0.1. As the gene for MinK is designated KCNE1, the new genes have been assigned KCNE2 (MiRP1), KCNE3 (MiRP2) and KCNE4

(MiRP3) by the Genome Database Nomenclature Committee (HUGO/GDB). The accession numbers for human MiRP1, rat MiRP1, human MiRP2, mouse MiRP2, and mouse MiRP3 are AF071002, AF071003, AF076531, AF076532 and AF076533, respectively.

SSCP analyses. Genomic samples were amplified by PCR and used in SSCP analysis. Three primer pairs were used in the mutation screen:

1F, 5'-CCGTTTTCCTAACCTTGTTCG-3' (SEQ ID NO:13) and 2R, 5'-AGCATCAACTTTGGCTTGGAG-3' (SEQ ID NO:14);

3F, 5'-GTCTTCCGAAGGATTTTTATTAC-3' (SEQ ID NO:15) and 4R, 5'-GTTCCCGTCTCTTGGATTTCA-3' (SEQ ID NO:16);

5F, 5'-AATGTTCTCTTTCATCATCGTG-3' (SEQ ID NO:17) and 6R, 5'-TGTCTGGACGTCAGATGTTAG-3' (SEQ ID NO:18).

PCR was carried out with 50 ng DNA in a final volume of 10 µl using a Perkin-Elmer Cetus 9600 thermocycler. PCR reactions had a final concentration of 4% formamide and 10% glycerol and were overlaid with mineral oil. Amplification conditions were 94° C. for 3 min followed by 35 cycles of 94° C. for 10 s, 55° C. for 20 s and 72° C. for 20 s, followed by extension for 5 min at 72° C. Reactions were diluted with 40 µl of 0.1% SDS/10 mM EDTA and with 30 µl of 95% formamide loading dye. The mixture was denatured at 94° C. for 5–10 min and immediately placed on ice. Three µl of each sample was electrophoresed on 5% polyacrylamide gel (acrylamide:bisacrylamide 49:1) at 4° C. and on 0.5× and 1×Mutation Detection Enhancement gels (MDE, FMC Bioproducts) at room temperature. Electrophoreses on the 5% gels were carried out at 40W for 2–3 hours and electrophoreses on 0.5× and 1×gels were run overnight at 350V or 800V, respectively. Gels were dried on 3MM filter paper and exposed to film for 18 hours at −70 C.

DNA sequencing. Aberrant and normal SSCP bands were excised from the gel and eluted in 100 µl ddH$_2$O at 65° C. for 30 min. Ten µl of the eluted DNA was used as a template in a second 100 µl PCR reaction using the original primer pair. Products were washed 3× with 400 µl ddH$_2$O in Microcon 100 microconcentrators (Amicon). DNA was directly sequenced in both directions by the dideoxy chain termination method, using the original primers, on an Applied Biosystems model 373A DNA sequencer.

Example 2

Electrophysiology Methods

Oocytes were isolated from *Xenopus laevis*, defolliculated by collagenase treatment and injected the following day with 46 nl cRNA. Whole cell currents were measured 2–4 days after injection of 1 ng HERG cRNA with or without 0.2 ng rat or human MiRP1 cRNA using a two electrode voltage clamp (Oocyte Clamp, Warner Instruments Inc., Hamden, Conn.), an IBM computer and non-commercial software. Data were sampled at 4 kHz and filtered at 1 kHz unless otherwise noted. Raw data are shown without leak correction. Single channel records were recorded using an Axopatch 200A amplifier (Axon Instruments, Foster City, Calif.), a Quadra 800 computer and ACQUIRE software (Instrutech, Great Neck, N.Y.) and stored unfiltered on VHS tape. The data were filtered through a 4 pole Bessel filter prior to analysis using TAC (Instrutech Corp., Great Neck, N.Y.) or IGOR (WaveMetrics Inc., Lake Oswego, Oreg.) packages. All experiments were performed at 22° C.

Protocols. Holding voltage in all cases −80 mV. (1) Steady-state activation; prepulse for 3 s from −80 to 40 mV in 10 mV steps, test pulse for 6 s to −100 mV; interpulse interval 5 s. (2) Activation kinetics; incremental prepulse durations from 0.005 to 3 s at 0 to 60 mV in 20 mV steps, test pulse for 3 s at −100 mV; interpulse interval 5 s. (3) Peak current; steady-state deactivation; deactivation kinetics; prepulse for 3 s to 30 mV, test pulse for 5 s from −150 to 10 mV in 10 mV steps; pulse to −120 mV for 1 s; interpulse interval 5 s. (4) Steady-state inactivation; prepulse for 3 s to 20 mV, pulse for 30 ms from to −120 to 60 mV in 10 mV steps; test pulse for 1 s at 20 mV; interpulse interval 2 s. (5) E-4031 blockade; 50 cycles were repeated: pulse for 3 s to 30 mV, test pulse for 5 s to −100 mV. (6) Isochronal and peak currents; pulse for 1 or 2 s from −80 to 20 or 40 mV in steps of 10 mV followed by a 2 s step to −40 mV with a 3 s interpulse interval. (7) Single channels were activated by a 2 s pulse from −80 to 20 mV followed by a test pulse of 4 or 6 s to voltages from −120 to −20 mV in steps of 10 mV with a 3 s interpulse interval.

Ionic conditions. Activation of channels formed only with HERG or containing both rMiRP1 and HERG subunits was assessed at various Ca$^{2+}$ concentrations by protocols 1 and 2. Treating Ca$^{2+}$ as a blocking ion we found an apparent equilibrium inhibition constant ($K_i$) for HERG channels of 0.29±0.02 mM at −100 mV, a value similar to that reported by others (Ho et al., 1998), while heteromeric channels containing rMiRP1 had an apparent $K_i$ ~3-fold lower. Initial characterizations were thus performed in a "low Ca$^{2+}$/high K$^+$" bath solution (in mM): 95 KCl, 5 NaCl, 1 MgCl$_2$, 0.3 CaCl$_2$ and 10 HEPES, pH 7.6 with NaOH. Other studies use solutions based on levels of ionized species found in human plasma (in mM): 4 KCl, 95 NaCl, 0.75 MgCl$_2$, 1 CaCl$_2$ and 10 HEPES, pH 7.6 with NaOH. For K$^+$ titrations in FIG. 4, NaCl and KCl were isotonically substituted. For cell-attached patches, pipette solution was (in mM): 100 KCl, 1 MgCl$_2$, 0.3 CaCl$_2$, 10 HEPES, pH 7.5 with KOH. For whole cell, pipettes contained (in mM): 100 KCl, 1 MgCl$_2$, 10 HEPES, 2 EGTA, pH 7.5 with KOH.

Pharmacology. Quinidine was purchased from Sigma, clarithromycin from American Bioanalytical (Natick, Mass.). Quinidine and E-4031 dissolved readily in bath solution. A 50 mM stock of clarithromycin in DMSO was diluted with bath solution for studies. Quinidine and clarithromycin were studied by protocol 1 at −40 mV with 1 mM Ca$^{2+}$, 4 mM KCl solution or as otherwise stated. E-4031 was studied by protocol 3 at −100 mV with 1 mM Ca$^{2+}$, 4 mM KCl solution for oocytes and protocol 1 at −40 mV for CHO cells. Hill coefficients were determined according to $1/(1+([drug]/K_i)^n)$.

Example 3

Biochemistry Methods rMiRP1 and HERG were epitope-tagged by replacing the terminal stop codon in each with nucleotides encoding HA residues (YPYDVPDYAX; SEQ ID NO:19) or cmyc residues (ISMEQKLISEEDLNX; SEQ ID NO:20). Transient transfection of COS cells was by DEAE-Detran, chloroquine, DMSO shock. Transfected cells were lysed in buffer A (in mM): 150 NaCl, 1% NP-40, 1% CHAPS, 0.2 PMSF, 20 NaF, 10 Na$_3$VO$_4$, 50 Tris, pH 7.4 and 0.7 µg/ml Pepstatin, before being clarified by centrifugation at 10,000g for 30 s. Immunoprecipitations were carried out with anti-cmyc monoclonal antibody 9E10 (Oncogene Research) and immobilized protein A/G (Pierce). Samples were separated by SDS-PAGE (10–16%). Western blots were performed with anti-HA monoclonal antibody 12CA5 (Boehringer) with a horseradish peroxidase-chemoluminescence coupled secondary antibody (Oncogene Research) for fluorography. Speedread Lysate 2™ (Novagen) rabbit reticulocyte lysate was used to generate protein subunits from cRNAs for rMiRP1, rMinK and HERG-cmyc. Subunits were radiolabelled with $^{35}$S-methionine (Amersham) and diluted in Buffer A containing 1.5% NP-40. Binding assays were performed by mixing equal volumes of the reaction mixtures and incubating for 2 hr on ice prior to IP as above.

Example 4

Identification and Cloning of Genes Encoding Products Related to MinK

Databases available through the National Center for Biotechnology Information (NCBI) were assessed for MinK-related sequences. Our search strategy targeted sites in MinK known to influence $I_{Ks}$ channel gating (Takumi et al., 1991; Splawski et al., 1997), ion selectivity (Goldstein and Miller, 1991; Tai and Goldstein, 1998), unitary conductance (Sesti and Goldstein, 1998), pore blockade (Goldstein and Miller, 1991; Wang et al., 1996; Tai and Goldstein, 1998) and those physically exposed in the $I_{Ks}$ channel conduction pathway (Wang et al., 1996; Tai and Goldstein, 1998). In this way, fragments of MinK-related genes were identified on 9 expressed sequence tags (ESTs) and 3 new genes cloned. As the gene for MinK is designated KCNE1, the new genes have been named KCNE2, KCNE3 and KCNE4 and their nucleotide and predicted protein sequences deposited with the NCBI.

Example 5

MiRP1 is an Ion Channel Subunit

As an EST gene fragment encoding rat MiRP1 (rMiRP1) detected an abundant single message in rat heart and skeletal muscle by Northern Blot analysis (FIG. 1A), a cardiac cDNA library was screened and multiple identical rMiRP1 clones were isolated. A predicted open reading frame of 369 bp forecasts a protein of 123 amino acids with 2 N-linked glycosylation sites, a single transmembrane segment and consensus sequences for 2 protein kinase C-mediated phosphorylation sites (FIG. 1C). This suggests MiRP1 has the same simple Type I membrane topology found for MinK— an extracellular amino-terminus followed by a single membrane-spanning stretch and a cytoplasmic carboxy-terminus (Busch et al., 1992; Blumenthal and Kaczmarek, 1994; Wang and Goldstein, 1995). Rat isolates of MiRP1 and MinK show 27% amino acid identity and 45% homology (FIG. 1C).

To test whether rMiRP1 could function as an ion channel subunit, its cRNA (1–25 ng) was injected into Xenopus laevis oocytes. Complementary RNA for MinK induces K$^+$ currents under these conditions by its association with a pore-forming subunit endogenous to the cells (Blumenthal and Kaczmarek, 1992; Wang and Goldstein, 1995; Sanguinetti et al., 1996; Tai et al., 1997). In contrast, measurements by two-electrode voltage clamp revealed no currents on days 1–14 following injection with cRNA for rMiRP1 (n=45, not shown). Moreover, cRNA for rMiRP1 had no apparent effect on channels formed by expression of KvLQT1, KCNQ2, Shaker, fast inactivation-removed (Δ6-46) Shaker, Kv1.3, Kv1.5, Kv1.6 or Kv2.1 subunits (n=15–39, not shown). Conversely, rMiRP1 had significant effects on the properties of channels formed with HERG subunits.

HERG channels open when depolarized to positive voltages that favor outward K$^+$ currents. They are described as inwardly-rectifying, however, because net ion movement through these channels is inward over a depolarization-hyperpolarization cycle when K$^+$ concentrations on both sides of the membrane are the same (a non-physiologic condition routinely used for channel characterization). As seen in recordings performed in symmetrical 100 mM KCl solution (FIG. 2), and modeled below, inward rectification results from rapid channel inactivation (Shibasaki, 1987; Sanguinetti et al., 1995; Trudeau et al., 1995; Smith et al., 1996; Wang et al., 1997; Zou et al., 1997).

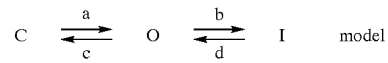

HERG channels activate from a closed to open state (C→O) upon depolarization but pass little outward current because they rapidly inactivate (O→I). With repolarization back to negative potentials, channels rapidly recover from the inactive state to the open state (O←I) and pass K$^+$ current until they close (C←O). The time spent in the open state during repolarization is significant because step c is fast compared to step d (a transition called deactivation). This is why the rate of deactivation has such a strong influence over the magnitude of K$^+$ current. Because lower Ca$^{2+}$ concentrations slow the gating transitions of native $I_{Kr}$ and HERG channels (Sanguinetti and Jurkiewicz, 1992; Ho et al., 1996) and (Sanguinetti et al., 1995; Ho et al., 1998), a 0.3 mM Ca$^{2+}$, 100 mM KCl solution was initially used to study the influence of rMiRP1 on channel function.

Activation was found to be altered by rMiRP1 using a protocol that estimates the fraction of channels that leave the closed state at equilibrium after the membrane is stepped to various test potentials (FIGS. 2A, 2C). Channels containing rMiRP1 required a more positive potential, −9±1 mV (mean±s.e.m. for 10 oocytes), to achieve half-maximal activation ($V_{1/2}$) when compared to channels formed only with HERG subunits; in contrast, no change in the slope factor was apparent (FIG. 2C). This shift in $V_{1/2}$ appeared to result from a slower rate of activation of channels formed with rMiRP1 (FIG. 2C inset, model step a).

Peak currents were also altered by rMiRP1. The size of whole-cell currents was assessed using a protocol that fully-activates channels by sustained depolarization and then measures maximal currents at various test potentials (FIG. 2B). Mean peak currents were 40% smaller for channels with rMiRP1 compared to those formed only with HERG subunits (FIG. 2D). As shown below, this resulted primarily from altered single-channel current (that is, the number of ions moving through the open channel per unit time) rather than changes in channel gating.

Inactivation (step b) was judged using a steady-state protocol (Smith et al., 1996) in which channel inactivation comes to equilibrium at various voltages during a prepulse so brief that little deactivation can occur; then, the fraction of channels in the inactive state is assessed by stepping the voltage to a test potential. Inactivation of HERG channels was the same as those containing rMiRP1 with prepulse voltages from −100 to 30 mV (FIG. 2E). The current-voltage relationships diverged only at potentials more negative than −100 mV where differences in deactivation became apparent. Recovery from inactivation (step c) remained extremely rapid in both channel types.

Deactivation of channels (step d) was markedly altered by rMiRP1. After channels were fully-activated by a depolarizing step, the speed with which channels returned to the closed state was assessed at various test potentials. Under these ionic conditions, rMiRP1 induced a 7-fold increase in deactivation rate (FIG. 2F). Thus, HERG channels did not deactivate appreciably until −100 mV and required a step 50 mV more negative to achieve the same deactivation rate as channels formed with rMiRP1. While deactivation was voltage-sensitive, the rate increase with rMiRP1 was unchanged from −100 to −150 mV (not shown).

Example 6

Figure 3A:
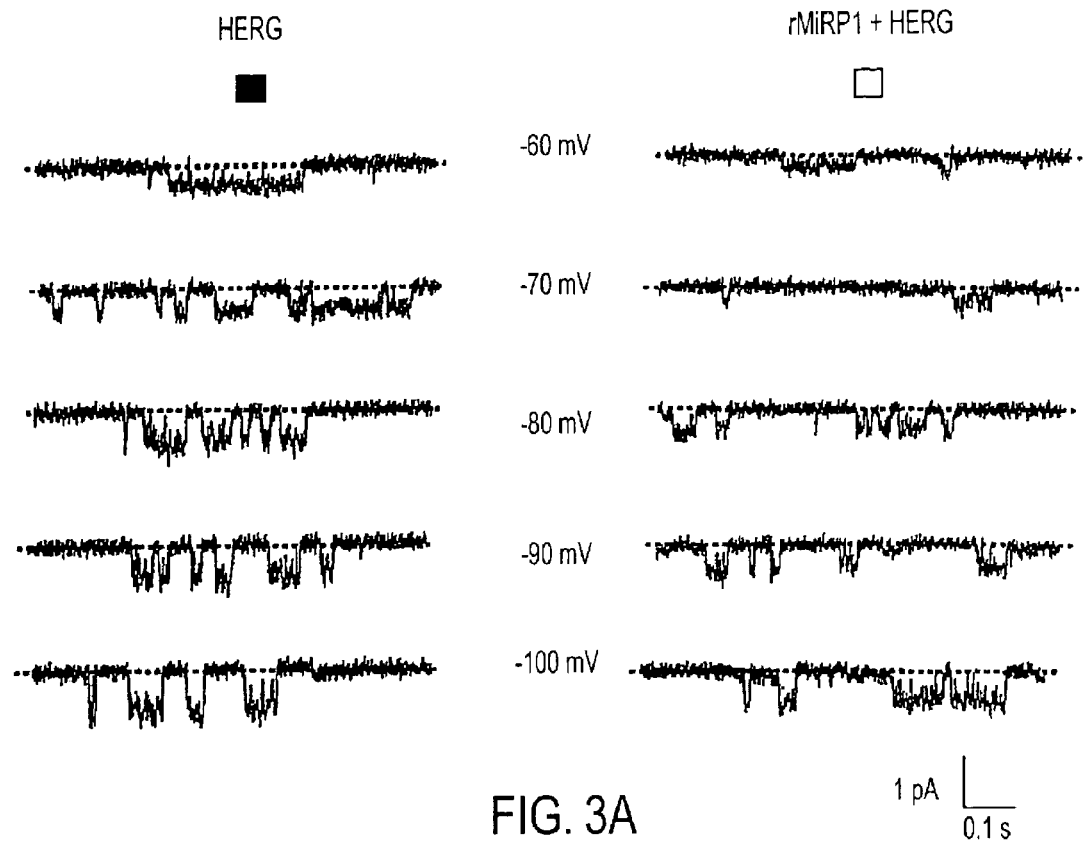
FIGS. 3A–3C show that single rMiRP1/HERG channels (□) are similar in conductance to native I$_{Kr}$ channels while HERG channels (■) are not. Performed in 0.3 mM Ca$^{2+}$, 100 mM KCl solution by protocol 7, as described in the Examples.
Figure 3B:
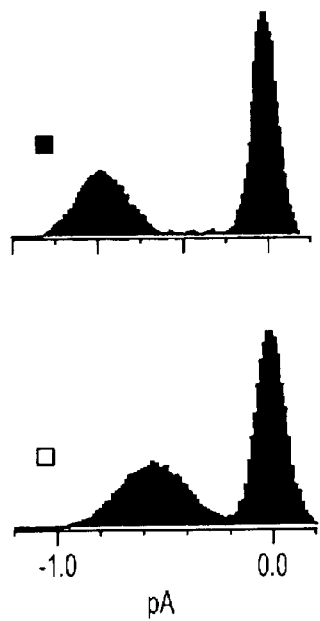
Figure 3C:
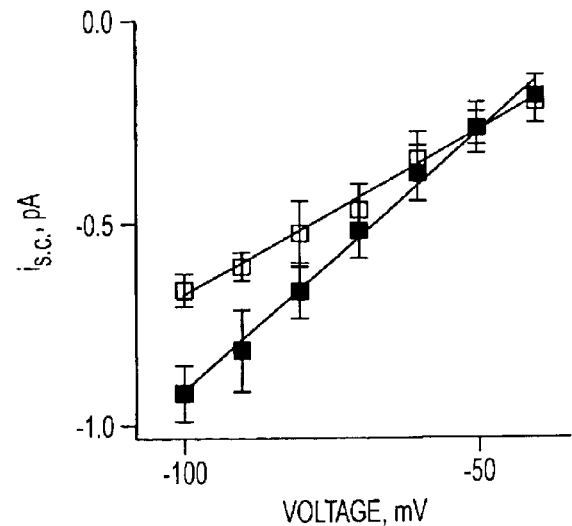

Unitary Conductance and Deactivation of rMiRP1/ HERG and Native $I_{Kr}$ Channels Single-channel analysis revealed the primary mechanism by which rMiRP1 decreased peak whole-cell currents (FIG. 2D). rMiRP1 caused a decrease in unitary current of ~40% through open channel complexes (FIGS. 3A, B). Thus, single HERG channels were found to have a slope conductance of 12.9±2 pS (FIG. 3C), as previously described (Zou et al., 1997). Channels containing rMiRP1 showed a value of 8±1 pS (FIG. 3C). This is similar to the unitary conductance value reported for native $I_{Kr}$ channels in rabbit atrioventricular node cells studied under identical conditions, 8.4 pS (Shibasaki, 1987).

Figures 4A, 4B:
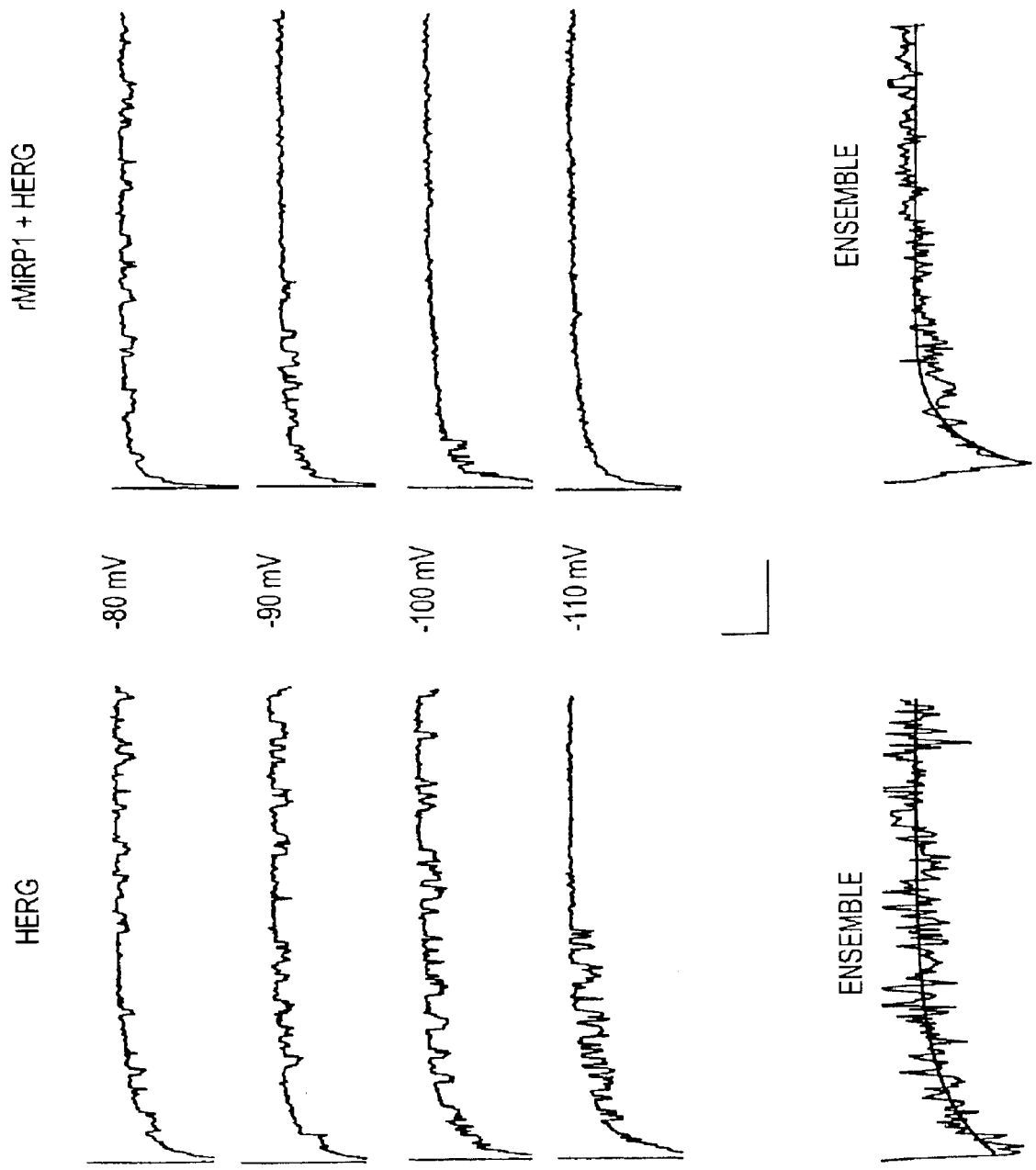
FIGS. 4A–4B show that single rMiRP1/HERG channels deactivate more rapidly than HERG channels.

The increased rate of channel deactivation seen when channels were formed with rMiRP1 and studied in whole-cell mode (FIG. 2F) was also apparent at the single-channel level (FIG. 4). While single HERG channels remained open for many seconds in patches held at −100 mV, as reported previously (Zou et al., 1997), channels formed with rMiRP1 closed rapidly (FIG. 4A). Ensemble averages of 50–70 traces emphasize the 2.3-fold acceleration of deactivation caused by formation of channels with rMiRP1 (FIG. 4B). In this way, channels formed with rMiRP1 were again like native $I_{Kr}$ channels. In human and mouse ventricular myocytes, $I_{Kr}$ channels were found to deactivate 2 to 3-fold faster than channels formed with HERG or murine ether a-go-go related gene (MERG) subunits alone (Yang et al., 1994; Sanguinetti et al., 1995; Lees-Miller et al., 1997; London et al., 1997).

Example 7

Regulation by External K$^+$ of rMiRP/HERG and Native $I_{Kr}$ Channels

Ionic conditions like those in human plasma (1 mM ionized Ca$^{2+}$, 4 mM KCl solution) were next employed. One hallmark of native $I_{Kr}$ channels and those formed only of HERG subunits is a negative slope for the current-voltage relationship at depolarized voltages; this results from channel inactivation (Sanguinetti et al., 1995; Smith et al., 1996; Spector et al., 1996). As expected, rMiRP1 had no significant effect on the shape of the current-voltage relationship (FIGS. 5A, B) since it had not altered channel inactivation (FIG. 2E). In contrast, up-regulation of outward K$^+$ currents associated with elevation of external K$^+$ concentration, another notable feature of both native $I_{Kr}$ and HERG channels (Sanguinetti and Jurkiewicz, 1992; Sanguinetti et al., 1995), was modified by rMiRP1. Channels containing rMiRP1 were less responsive than HERG channels when external K$^+$ ion was varied from 1 to 8 mM (FIG. 5C). A shallow response to external K$^+$, like that seen here with rMiRP1, was also found when native $I_{Kr}$ channels were studied in murine atrial cells or guinea pig ventricular myocytes (Shibasaki, 1987; Scamps and Carmeliet, 1989; Sanguinetti and Jurkiewicz, 1992; Sanguinetti et al., 1995; Yang and Roden, 1996). Studied in plasma-like ionic conditions and whole-cell mode, rMiRP1 was again observed to increase the rate of deactivation, ~2-fold from τ=130±8 ms for HERG channels to 61±4 ms (mean±s.e.m., protocol 3, n=5 cells) (FIG. 5D).

The combined effects of rMiRP1 on activation, deactivation and regulation by external K$^+$ ion, under these ionic conditions, produced a current-voltage relationship that was little changed in its shape compared to channels formed by HERG subunits alone (FIG. 5B). However, oocytes expressing channels with rMiRP1 passed half the inward current and one-quarter the outward current of those with HERG channels (FIGS. 5D, 5E).

Example 8

Stable Association of rMiRP1 and HERG Subunits

Subunit interaction between rMiRP and HERG was evaluated first by studying the proteins modified with epitope tags and expressed in mammalian tissue culture cells. Epitopes had no apparent effect on macroscopic channel activity (not shown). Transient expression of rMiRP1-HA in COS cells, followed by western blot analysis with anti-HA antibody, revealed three specific bands at migration distances appropriate for the mature protein and small amounts of its mono- and unglycosylated forms (FIG. 6A, lane 1); endoglycosidase F treatment resulted in collapse of the profile to one specific band at the lowest predicted mass (not shown).

Figure 6A:
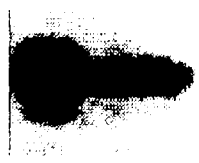
FIGS. 6A–6B show that rMiRP1 and HERG subunits form stable complexes.

Co-expression of rMiRP1-HA with HERG-cmyc allowed recovery of rMiRP1-HA by immunoprecipitation (IP) with an anti-cmyc monoclonal antibody (FIG. 6A, lane 2). Recovery was shown to be specific because anti-cmyc IP gave no signal when HERG-cmyc was expressed alone (FIG. 6A, lane 3), when rMiRP1-HA was expressed alone (FIG. 6A, lane 4) or when the channel protein connexin 43-cmyc was expressed with rMiRP1-HA (FIG. 6A, lane 5).

Figure 6B:

As reported previously, MinK and HERG-cmyc also co-assemble (McDonald et al., 1997). To compare the binding of MinK and MiRP1 to HERG-cmyc, an assay was performed using $^{35}$S-labeled MinK and MiRP1 subunits synthesized in vitro. Incubation of rMiRP1 and HERG-cmyc followed by anti-cmyc IP allowed strong recovery of rMiRP1, as judged by autoradiography (FIG. 6B, lane 1). Similarly, incubation of rMinK and HERG-cmyc allowed strong recovery of rMinK (FIG. 6B, lane 2). When rMiRP1 and rMinK were mixed in a 1:1 ratio and incubated at 5-fold molar excess with HERG-cmyc, anti-cmyc IP led to strong recovery of rMiRP1, like that seen in the absence of rMinK, while recovery of rMinK was poor (FIG. 6B, lane 3). Thus, rMinK and rMiRP1 could each assemble with HERG-cmyc. However, under these in vitro conditions, the presence of both peptides favored formation of stable rMiRP1/HERG complexes in preference to those with rMinK.

Example 9

Cloning and Function of the Human MiRP1 Gene, hKCNE2

Based on the presumed molecular correlation of MiRP1/ HERG channel complexes and native cardiac $I_{Kr}$ channels, we cloned the gene for human MiRP1 (hKCNE2) to screen for the presence of mutations in patients with cardiac arrhythmias. Multiple identical clones were isolated from a human cardiac muscle cDNA library. As in rat, transcripts were detected in heart and skeletal muscle (not shown). The human cDNA also predicted a protein of 123 amino acids with 2 N-linked glycosylation sites, a single transmembrane segment and 2 protein kinase C-mediated phosphorylation sites. Alignment of rat and human MiRP1 showed 82% identity and 97% homology (FIG. 1c).

The hKCNE2 gene was localized to chromosome 21q22.1 (accession number AP000052). This was notable because hKCNE1, the gene encoding MinK, was previously localized to this site (accession number AP000053). The 2 genes are arrayed in opposite orientation, separated by 79 kb. Their open reading frames share 34% identity and both are contained in a single exon (Splawski et al., 1998). This suggests that MiRP1 and MinK are related through gene duplication and divergent evolution.

Wild type human MiRP1, studied by transient expression in Chinese Hamster Ovary (CHO) cells using 1 mM $Ca^{2+}$, 4 mM KCl solution, had the same effects as rat MiRP1. Like channels with rMiRP1, hMiRP1/HERG complexes required depolarization to more positive potentials to achieve half-maximal activation and showed no change in slope factor compared to channels formed by HERG subunits alone (Table 1). Like rMiRP1, hMiRP1 did not alter steady-state inactivation (not shown). Like those with rMiRP1, hMiRP1/HERG complexes deactivated faster than HERG channels, ~3-fold (Table 1, $\tau_f$ at −120 mV). Finally, the unitary conductance of channels formed with hMiRP1 (in oocytes) was the same as that measured for channels with rMiRP1, 8.0±0.7 pS (n=11 patches, not shown, as in FIG. 3C).

relaxation to equilibrium block with subsequent test pulses (Carmeliet, 1992; Carmeliet, 1993).

As expected, HERG channels expressed in CHO cells and bathed in E-4031 showed minimal inhibition on the first test pulse (FIG. 7A). In marked contrast, channels formed with hMiRP1 were significantly inhibited on the first pulse, like native $I_{Kr}$ channels (FIG. 7B). The fraction of unblocked current in the first pulse by 1 μM E-4031 was 0.9±0.1 for HERG channels and 0.6±0.2 for channels formed with hMiRP1 and HERG (n=9 cells).

Figure 7C:
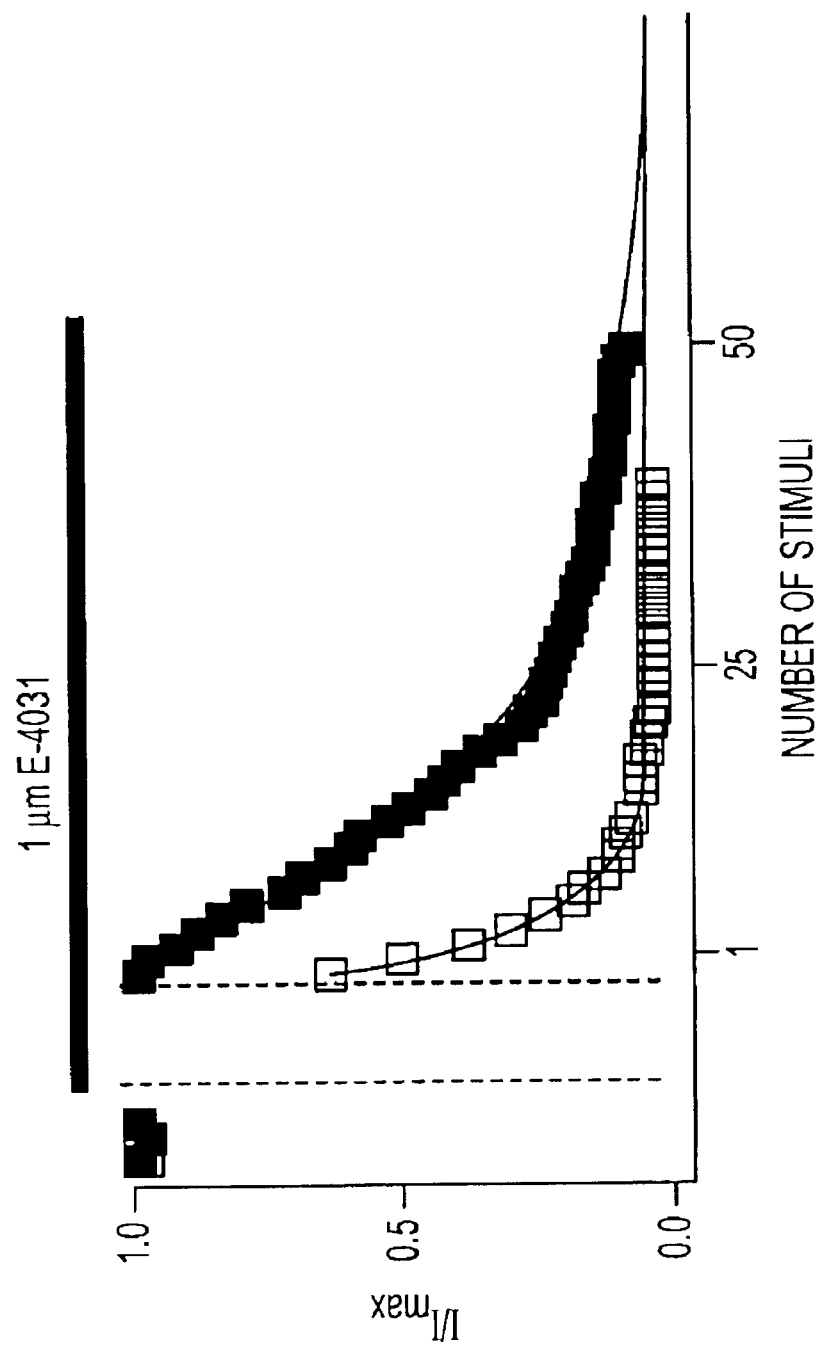

HERG channels in CHO cells reached equilibrium slowly with repetitive pulses (FIG. 7C); relaxation was best-approximated by a single exponential decay with a time constant (τ) of 26±9 pulse cycles (n=9 cells). Block of channels with hMiRP1 was best-described as an initial fast block followed by a single exponential decay with τ=4±1 pulse cycles (n=7 cells, FIG. 7C). Thus, mixed channel complexes reproduced the characteristic biphasic blocking kinetics observed with native $I_{Kr}$ channels (Carmeliet, 1992; Carmeliet, 1993).

Methanesulfonanilide potency varies widely with cell type and ionic condition (Snyders and Chaudhary, 1996; Yang and Roden, 1996; Yang et al., 1997). Others have found block of HERG channels by E-4031 to be weak in oocytes, $K_i$=588 nM (Trudeau et al., 1995) and strong in mammalian tissue culture cells, $K_i$=7.7 nM (Zhou et al., 1998). In oocytes, we also find E-4031 block of HERG channels to be poor, $K_i$=1,250±200 nM; channels formed with rMiRP1 and HERG were ~3-fold more sensitive, $K_i$=380±60 (FIG. 5F). In CHO cells, HERG channels were strongly blocked by E-4031, $K_i$=8.8±0.8 nM; again, channels formed with hMiRP1 were ~2-fold more sensitive, $K_i$=4.6±0.6 nM (n=6 cells). Native $I_{Kr}$ channels in ferret

TABLE 1

Activation and Deactivation parameters of hMiRP1/HERG Channels and Channels Formed Only With HERG Subunits

| channel (# of cells) | activation $V_{1/2}$ mV | activation slope, mV | deactivation $\tau_f$ s | deactivation $\tau_s$, s | deactivation ratio $I_f/(I_s + I_f)$ |
|---|---|---|---|---|---|
| HERG (11) | −25 ± 5 | 9.1 ± 1.4 | 241 ± 119 | 782 ± 376 | 0.59 ± 0.19 |
| WT hMiRP1 (21) | −21 ± 6 | 9.5 ± 1.0 | 80 ± 26 | 483 ± 491 | 0.82 ± 0.03 |
| T8A hMiRP1 (15) | −29 ± 6 | 9.4 ± 1.7 | 100 ± 40 | 590 ± 370 | 0.83 ± 0.05 |
| Q9E hMiRP1 (14) | −12 ± 4 | 7.6 ± 0.4 | 100 ± 27 | 750 ± 451 | 0.80 ± 0.11 |
| M54T hMiRP1 (10) | −21 ± 6 | 7.2 ± 2.0 | 37 ± 8 | 266 ± 35 | 0.81 ± 0.06 |

Activation kinetics were estimated in macropatches in 1.0 mM $Ca^{2+}$, 4 mM KCl solution. Currents were measured and fitted for activation parameters as in FIG. 2; for deactivation, a double exponential function ($I_O + I_f e^{(-t/\tau)}{}_f + I_s e^{(-t/\tau)}{}_s$) and protocol 3 were used (−120 mV).
When blockade was studied in 1 mM $Ca^{2+}$, 1 mM KCl solution, channels with wild type hMiRP1 showed a $V_{1/2}$ = −20 ± 5 mV and slope = 9.2 ± 2 while Q9E-hMiRP1 channels had a $V_{1/2}$ = −12 ± 5 mV and slope = 7.6 ± 1 (n = 7–13 cells).

Example 10 hMiRP1/HERG and Native $I_{Kr}$ Channels Exhibit Biphasic Class III Block Kinetics A fundamental discrepancy between cloned HERG and native $I_{Kr}$ channels is their disparate responses to methanesulfonanilide Class III antiarrhythmics like E-403 1. Closed HERG channels exposed to the agents show little inhibition with an initial test pulse and achieve equilibrium blockade slowly with repetitive activating pulses or prolonged depolarization (Spector et al., 1996; Zhou et al., 1998). In contrast, native $I_{Kr}$ channels show 2 phases of blockade—significant inhibition with the initial test pulse and ready cardiac myocytes were found to be sensitive to E-4031, $K_i$=10.3 nM (Liu et al., 1996).

Example 11

Mutations in Human MiRP1 are Associated with Arrhythmia

To test the hypothesis that MiRP1 mutants cause cardiac arrhythmia, we screened a panel of 20 patients with drug-induced arrhythmia and 230 patients with inherited or sporadic arrhythmias and no mutations in their KVLQT1, HERG, SCN5A or KCNE1 genes. A control population of 1,010 individuals was also evaluated. Analysis by SSCP and DNA sequencing revealed 3 abnormalities and 1 polymorphism.

Q9E-hMiRP1. One of 20 patients with drug-induced arrhythmia had a C to G transversion at nucleotide +25 (nucleotide 98 of SEQ ID NO:1) of hKCNE2 producing a Q9 to E substitution in the putative extracellular domain of hMiRP1. This mutation was not identified in 1,010 control individuals. The patient is a 76 year old African American female with a history of high blood pressure, non-insulin dependent diabetes and stroke. Two baseline electrocardiograms showed QT intervals corrected for heart rate that were borderline prolonged (QTc=460 ms). Echocardiography revealed concentric left ventricular hypertrophy with mild to moderate diffuse hypokinesis but no ventricular dilatation. The patient was admitted to the hospital with pneumonia and treated with 7 doses of intravenous erythromycin, 500 mg every 6 hours and then switched to oral clarithromycin, 500 mg every 12 hours. After 2 doses of clarithromycin electrocardiography showed a QTc of 540 ms. The patient developed TdP and VF, requiring defibrillation. At the time, she was hypokalemic with a serum potassium level of 2.8 meq/L.

M54T-hMiRP1. One of 230 patients with inherited or sporadic arrhythmias had a T to C transition at nucleotide +161 (nucleotide 234 of SEQ ID NO:1) causing substitution of M54 to T in the predicted transmembrane segment. This mutation was not identified in 1,010 control individuals. This patient is a 38 year old Caucasian female who was in good health. She was on no medications. This individual had VF while jogging. Her resuscitation required defibrillation. The results from echocardiography and cardiac catheterization with electrophysiologic studies and right ventricular biopsy were normal. Subsequent electrocardiograms showed an atypical response to exercise with QTc intervals ranging from 390 to 500 ms. An automatic internal defibrillator was placed.

I57T-hMiRP1. Another of the 230 patients with inherited or sporadic arrhythmias had a T to C transition at +170 (nucleotide 243 of SEQ ID NO:1) causing an I57 to T substitution in the predicted transmembrane segment. This patient is a 48 year old Hispanic female who is in good health and has no history of TdP or VF. Her resting electrocardiogram shows a prolonged QT interval (QTc=470 ms). She is a member of a multi-generational family now under genetic, clinical and biophysical evaluation.

T8A-hMiRP1. In 18 out of 1,260 individuals screened, an A to G polymorphism at nucleotide +22 (nucleotide 95 of SEQ ID NO:1) produced a T8 to A change in the putative extracellular domain of MiRP1. The change was found in 1 patient with quinidine-induced arrhythmia, 1 with inherited or sporadic arrhythmia and 16 controls.

Example 12

Arrhythmia-associated hMiRP1 Mutants Decrease K$^+$ Flux

Figures 8A, 8B:
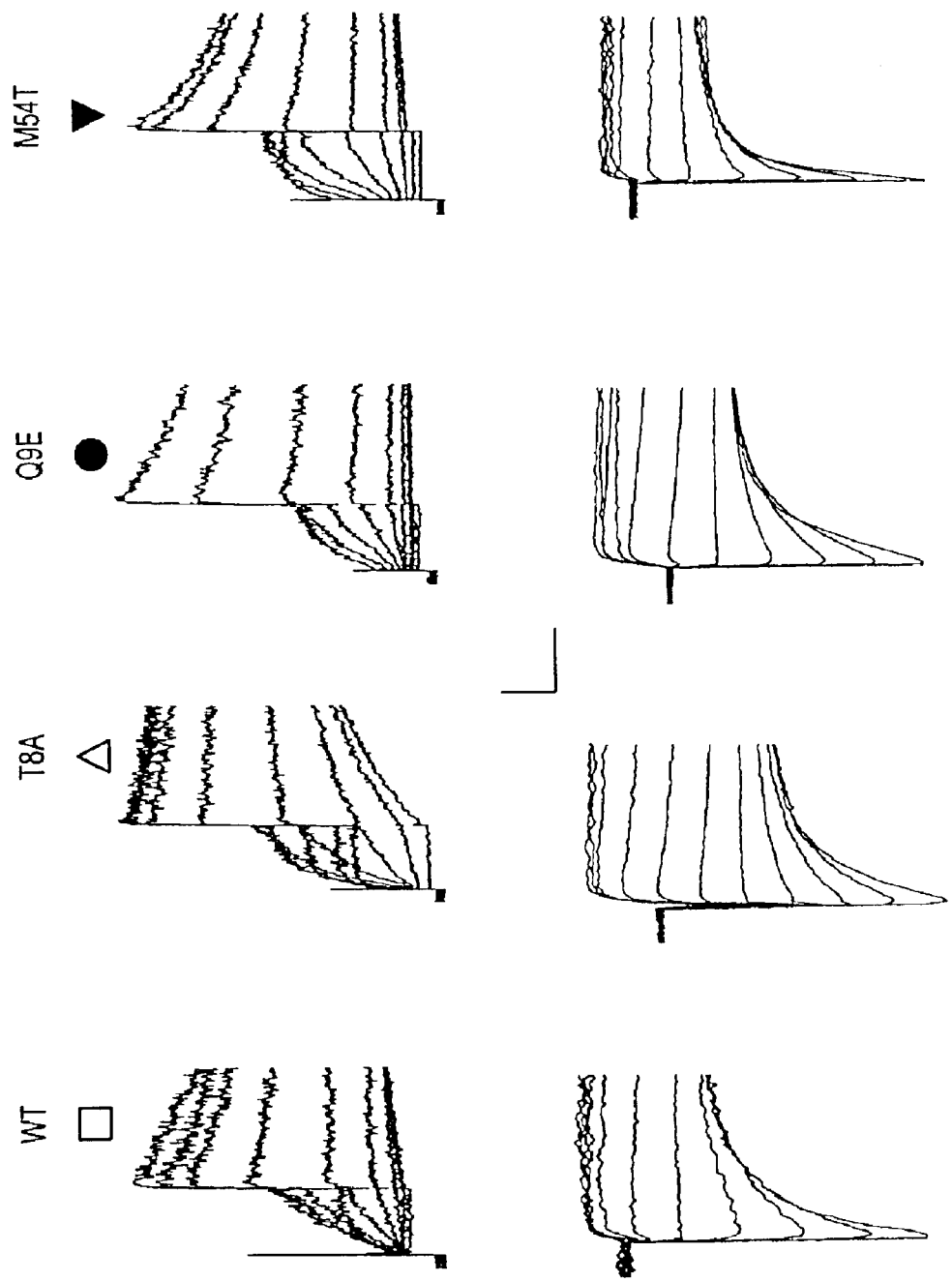
FIGS. 8A–8D show that function of channels with wild type or arrhythmia-associated hMiRP1 subunits.
Figure 8C:
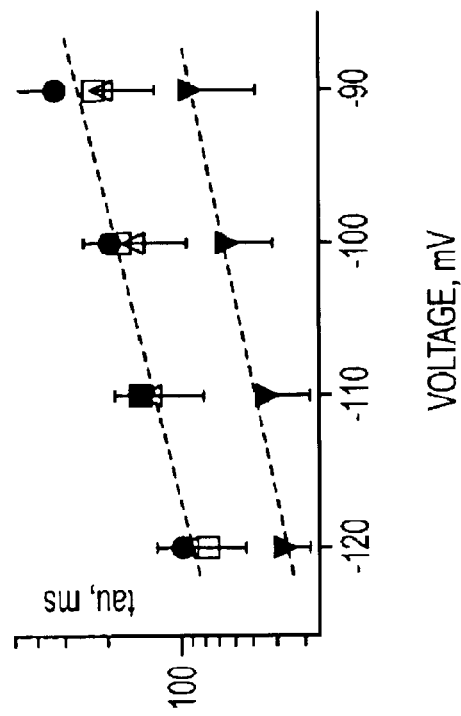
Figure 8D:
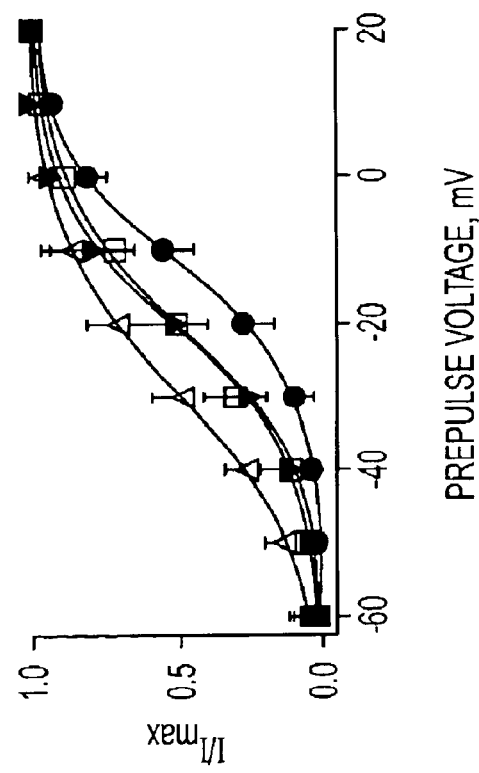

Wild type hMiRP1/HERG channels and those formed with Q9E, M54T, I57T or T8A-hMiRP1 were compared by transient expression in CHO cells using 1 mM Ca$^{2+}$, 4 mM KCl solution. Mutant channels formed with Q9E-hMiRP1 and HERG were like those formed with wild type subunits in their steady-state inactivation and rate of deactivation (FIGS. 8B, 8D; Table 1). However, this mutant increased the voltage-dependence of channel activation. Thus, Q9E-hMiRP1 channels required depolarization to more positive potentials to achieve half-maximal activation and had a diminished slope factor compared to wild type (FIG. 5C; Table 1). An increase in voltage-dependence yields fewer open channels for a given depolarizing step and, therefore, decreased K$^+$ flux. In the heart, diminished K$^+$ current is predicted to slow phase 3 repolarization. This lengthens the cardiac action potential duration and is reflected on the surface electrocardiogram as a prolonged QT interval.

Mutant channels formed with M54T-hMiRP1 were like wild type in their steady-state inactivation (not shown). However, this mutant also increased the voltage-dependence of activation, in this case by diminishing the activation slope factor without altering V$_{1/2}$ (FIG. 8C; Table 1). In addition, channels formed with this mutant showed a speeded rate of closing; these channels deactivated ~3-fold faster than those with wild type hMiRP1 and 6–7 fold faster than channels formed by HERG subunits alone (FIG. 8D; Table 1). As before, increased voltage-dependence results in fewer open channels for a given voltage step; faster deactivation indicates that mutant channels, if they do open, will close more rapidly than wild type. In the heart, both these effects would reduce K$^+$ current, prolonging the cardiac action potential and the QT interval measured on an electrocardiogram.

I57T-hMiRP1 also diminished K$^+$ flux through MiRP1/HERG channel complexes and will be considered in detail elsewhere (Splawski et al., 1999).

The T8A-hMiRP1 variant was isolated from 18 of 1260 individuals screened. While channels containing the variant were similar to those with wild type MiRP1, they showed decreased voltage-dependence for activation, opening more readily upon depolarization (FIGS. 5B, 8C, 8D; Table 1). The variant was found in 2 patients with arrhythmia, 1 with quinidine-induced QT prolongation (500 ms). Because quinidine is known to inhibit cardiac I$_{Kr}$ channels (Roden et al., 1986), we compared blockade of channels formed with wild type or T8A-hMiRP1. Quinidine sensitivity of the 2 channel types was not significantly different; wild type channels exhibited an equilibrium constant (K$_i$) of 0.79±0.18 µM while T8A-hMiRP1 channels had a K$_i$=0.84±0.10 µM with Hill coefficients of 1.1±0.07 and 1.0±0.05, respectively (n=7 cells).

Example 13

Increased Blockade by Clarithromycin of Channels Formed with Q9E-hMiRP1

Figure 9A:
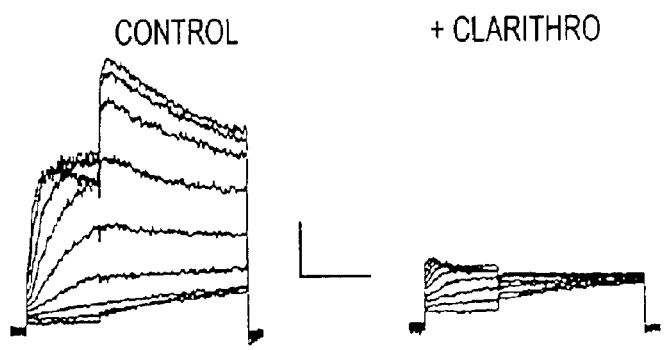
FIGS. 9A–9C show that Q9E-hMiRP1 is associated with clarithromycin-induced arrhythmia and increased drug sensitivity. Unless indicated, 1 mM $Ca^{2+}$, 4 mM KCl solution (Examples) was used.
Figure 9B:
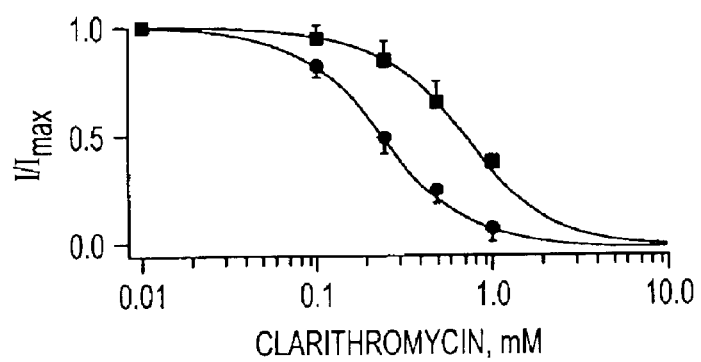
Figure 9C:
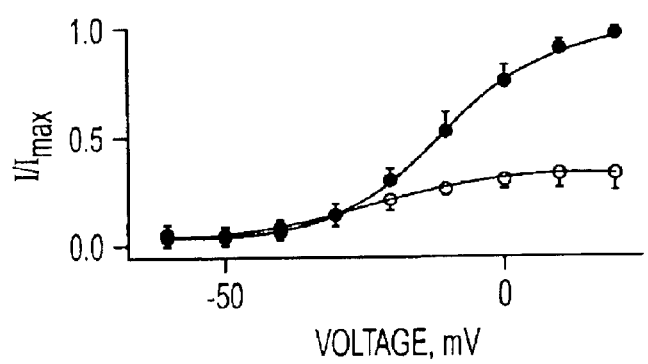

Q9E-hMiRP1, associated with clarithromycin-induced TdP and VF, assembles with HERG to form channels with increased sensitivity to blockade by this macrolide antibiotic. The dose leading to half-block of peak outward current for channels formed with wild type hMiRP1 was 0.72±0.18 mM, similar to that measured for channels formed only with HERG (0.75±0.31 mM). In contrast, channels formed with Q9E-hMiRP1 exhibited a K$_i$ of 0.24±0.04 mM (FIGS. 9A, 9B). Blockade was observed only at voltages positive to the threshold for activation and increased as the prepulse potential became more positive (FIG. 9C). This is consistent with block of open channels, a mechanism thought to underlie inhibition of I$_{Kr}$ channels by Class III antiarrhythmic agents (Spector et al., 1996; Wang et al., 1997). However, clarithromycin also caused a 10 mV shift to more positive potentials in the V$_{1/2}$ (with no change in slope factor) for both wild type and Q9E-hMiRP1 channels (FIG. 9C). At present, the mechanism of clarithromycin inhibition is best described as state-dependent.

As native I$_{Kr}$ channels show increasing sensitivity to Class III agents with lowered external K$^+$ (Yang and Roden, 1996) we re-assessed clarithromycin block when bath K$_i$ concentration was reduced from 4 to 1 mM. While changing the solution had no effect on activation of either channel (Table 1), the blocking potency of clarithromycin was increased ~20% for both channels formed with wild type MiRP1 and those with Q9E-hMiRP1 (wild type $K_i$=0.59±0.1, for Q9E-hMiRP1 $K_i$=0.20±0.07 mM, n=6 cells each, not shown). Thus, channels formed with Q9E-hMiRP1 are more sensitive to clarithromycin blockade and inhibition is intensified by intercurrent hypokalemia.

Example 14

Generation of Polyclonal Antibody Against KCNE2

Segments of KCNE2 coding sequence are expressed as fusion protein in *E. coli*. The overexpressed protein is purified by gel elution and used to immunize rabbits and mice using a procedure similar to the one described by Harlow and Lane (1988). This procedure has been shown to generate Abs against various other proteins (for example, see Kraemer et al., 1993).

Briefly, a stretch of KCNE2 coding sequence is cloned as a fusion protein in plasmid PET5A (Novagen, Inc., Madison, Wis.). After induction with IPTG, the overexpression of a fusion protein with the expected molecular weight is verified by SDS/PAGE. Fusion protein is purified from the gel by electroelution. Identification of the protein as the KCNE2 fusion product is verified by protein sequencing at the N-terminus. Next, the purified protein is used as immunogen in rabbits. Rabbits are immunized with 100 µg of the protein in complete Freund's adjuvant and boosted twice in 3 week intervals, first with 100 µg of immunogen in incomplete Freund's adjuvant followed by 100 µg of immunogen in PBS. Antibody containing serum is collected two weeks thereafter.

This procedure is repeated to generate antibodies against the mutant forms of the KCNE2 gene product. These antibodies, in conjunction with antibodies to wild type KCNE2, are used to detect the presence and the relative level of the mutant forms in various tissues and biological fluids.

The above procedure is also used to generate polyclonal antibodies specific for KCNE3 and KCNE4.

Example 15

Generation of Monoclonal Antibodies Specific for KCNE2

Monoclonal antibodies are generated according to the following protocol. Mice are immunized with immunogen comprising intact KCNE2 or KCNE2 peptides (wild type or mutant) conjugated to keyhole limpet hemocyanin using glutaraldehyde or EDC, as is well known.

The immunogen is mixed with an adjuvant. Each mouse receives four injections of 10 to 100 µg of immunogen and after the fourth injection blood samples are taken from the mice to determine if the serum contains antibody to the immunogen. Serum titer is determined by ELISA or RIA. Mice with sera indicating the presence of antibody to the immunogen are selected for hybridoma production.

Spleens are removed from immune mice and a single cell suspension is prepared (see Harlow and Lane, 1988). Cell fusions are performed essentially as described by Kohler and Milstein (1975). Briefly, P3.65.3 myeloma cells (American Type Culture Collection, Rockville, Md.) are fused with immune spleen cells using polyethylene glycol as described by Harlow and Lane (1988). Cells are plated at a density of 2×10⁵ cells/well in 96 well tissue culture plates. Individual wells are examined for growth and the supernatants of wells with growth are tested for the presence of KCNE2 specific antibodies by ELISA or RIA using wild type or mutant KCNE2 target protein. Cells in positive wells are expanded and subcloned to establish and confirm monoclonality.

Clones with the desired specificities are expanded and grown as ascites in mice or in a hollow fiber system to produce sufficient quantities of antibody for characterization and assay development.

The above procedure is also used to generate monoclonal antibodies specific for KCNE3 and KCNE4.

Example 16

Sandwich Assay for KCNE2

Monoclonal antibody is attached to a solid surface such as a plate, tube, bead or particle. Preferably, the antibody is attached to the well surface of a 96-well ELISA plate. 100 µL sample (e.g., serum, urine, tissue cytosol) containing the KCNE2 peptide/protein (wild-type or mutants) is added to the solid phase antibody. The sample is incubated for 2 hrs at room temperature. Next the sample fluid is decanted, and the solid phase is washed with buffer to remove unbound material. 100 µL of a second monoclonal antibody (to a different determinant on KCNE2 peptide/protein) is added to the solid phase. This antibody is labeled with a detector molecule (e.g., $^{125}$I, enzyme, fluorophore, or a chromophore) and the solid phase with the second antibody is incubated for two hrs at room temperature. The second antibody is decanted and the solid phase is washed with buffer to remove unbound material.

The amount of bound label, which is proportional to the amount of KCNE2 peptide/protein present in the sample, is quantified. Separate assays are performed using monoclonal antibodies which are specific for the wild-type KCNE2 as well as monoclonal antibodies specific for each of the mutations identified in KCNE2.

The above procedure is also used to assay for KCNE3 and KCNE4 using the appropriate KCNE3 or KCNE4 antibodies.

Example 17

Assay to Screen Drugs Affecting the KCNE2 K⁺ Channel

With the knowledge that KCNE2 coassembles to form a cardiac $I_{Ks}$ potassium channel, it is now possible to devise an assay to screen for drugs which will have an effect on this channel. The gene KCNE2 is cotransfected into oocytes or mammalian cells and coexpressed as described above. The cotransfection is performed using any combination of wild-type or specifically mutated KCNE2. When one of the genes used for cotransfection contains a mutation which causes LQT a change in the induced current is seen as compared to cotransfection with wild-type genes only. A drug candidate is added to the bathing solution of the transfected cells to test the effects of the drug candidates upon the induced current. A drug candidate, which alters the induced current such that it is closer to the current seen with cells cotransfected with wild-type KCNE2, is useful for treating LQT.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Altschul, S. F. et al. (1990). *J. Mol. Biol.* 215403–10.
Altschul S. F. et al. (1997). *Nucl. Acids Res.* 25:3389–3402.
Anand, R. (1992). *Techniques for the Analysis of Complex Genomes*, (Academic Press).
Anderson, W. F. et al. (1980). *Proc. Natl. Acad. Sci. USA* 77:5399–5403.
Anderson, M. A. and Gussella, J. F. (1984). *In Vitro* 20:856–858.
Antzelevitch, C. and Sicouri, S. (1994). *J. Am. Col. Card.* 23:259–277.
Antzelevitch, C. et al. (1996). *J Am Coll Cardiol* 28:1836–48.
Attali, B. et al. (1993). *Nature* 365:850–852.
Attwell, D. et al. (1979). *Pflugers Arch.* 379:137–142.
Ausubel, F. M. et al. (1992). *Current Protocols in Molecular Biology*, (John Wiley & Sons, New York, N.Y.).
Balser, J. P. et al. (1990). *J. Gen. Physiol.* 96:835–863.
Balser, J. R. et al. (1991). *Circ. Res.* 69:519–529.
Bandyopadhyay P K and Temin H M (1984). *Mol. Cell. Biol.* 4:749–754.
Barhanin J, et al. (1996). *Nature* 384:78–80.
Bartel P L, et al. (1993). "Using the 2-hybrid system to detect protein-protein interactions." In *Cellular Interactions in Development: A Practical Approach*, Oxford University Press, pp. 153–179.
Bazzett H (1920). *Heart* 7:353–370.
Beaucage S L and Caruthers M H (1981). *Tetra. Letts.* 22:1859–1862.
Berglund P, et al. (1993). *Biotechnology* 11:916–920.
Berkner K L, et al. (1988). *BioTechniques* 6:616–629.
Berkner K L (1992). *Curr. Top. Microbiol. Immunol.* 158:39–66.
Blumenthal, E. M. and Kaczmarek, L. K. (1992). *Neurochemical Research* 17:869–76.
Blumenthal, E. M. and Kaczmarek, L. K. (1994). *J. Neurosci.* 14:3097–105.
Borman S (1996). *Chemical & Engineering News*, December 9 issue, pp. 42–43.
Breakefield X O and Geller A I (1987). *Mol. Neurobiol.* 1:337–371.
Brinster R L, et al. (1981). *Cell* 27:223–231.
Bruggemann A, et al. (1993). *Nature* 365:445–448.
Buchschacher G L and Panganiban A T (1992). *J. Virol.* 66:2731–2739.
Buckler A J, et al. (1991). *Proc. Natl. Acad Sci. USA* 88:4005–4009.
Burn T C, et al. (1995). *Gene* 161:183–187.
Busch A E, et al. (1992). *Science* 255:1705–1707.
Busch, A. E. et al. (1997). *Br J Pharmacol* 122:187–9.
Capecchi M R (1989). *Science* 244:1288.
Cardiac Arrhythmia Suppression Trial II Investigators (1992). *N. Engl. J. Med.* 327:227–233.
Cariello N F (1988). *Am. J. Human Genetics* 42:726–734.
Carlsson, L. et al. (1997). *J. Pharmacol. Exp. Ther.* 282:220–7.
Carmeliet, E. (1992). *J. Pharmacol. Exp. Ther.* 262:809–17.
Carmeliet, E. (1993). *Circ Res* 73:857–68.
Chee M, et al. (1996). *Science* 274:610–614.
Chen, J. et al. (1999). *Biophys. J.* 76:A331.
Chevray P M and Nathans D N (1992). *Proc. Natl. Acad. Sci. USA* 89:5789–5793.
Chin H M, et al. (1991). *Genomics* 11:914–919.
Church D M, et al. (1994). *Nat. Genet.* 6:98–105.
Compton J (1991). *Nature* 350:91–92.
Conner B J, et al. (1983). *Proc. Natl. Acad Sci. USA* 80:278–282.
Costantini F and Lacy E (1981). *Nature* 294:92–94.
Cotten M, et al. (1990). *Proc. Natl. Acad. Sci. USA* 87:4033–4037.
Cotton R G, et al. (1988). *Proc. Natl. Acad. Sci. USA* 85:4397–4401.
Covarrubias M, et al. (1991). *Neuron* 7:763–773.
Cui J, et al. (1994). *J. Gen. Physiol.* 104:87–105.
Culver K W, et al. (1992). *Science* 256:1550–1552.
Culver K (1996). *Gene Therapy: A Primer for Physicians*, 2nd Ed., Mary Ann Liebert.
Curiel D T, et al. (1991). *Proc. Natl. Acad. Sci. USA* 88:8850–8854.
Curiel D T, et al. (1992). *Hum. Gene Ther.* 3:147–154.
Curan M E, et al. (1995). *Cell* 80:795–804.
Daleau, P. et al. (1995). *Circulation* 91:3010–6.
DeRisi J, et al. (1996). *Nat. Genet.* 14:457–460.
Deutscher M (1990). *Meth Enzymology* 182:83–89 (Academic Press, San Diego, Calif.).
Donehower L A, et al. (1992). *Nature* 356:215.
Drici, M. D. et al. (1998). *JAMA* 280:1774–6.
Duggal P et al. (1998). *Circulation* 97:142–146.
Ebert, S. N. et al. (1998). *J Womens Health* 7:547–57.
Editorial (1996). *Nature Genetics* 14:367–370.
Eichelbaum, M. et al. (1996). *Clin. Exp. Pharmacol. Physiol.* 23: 983–985.
Elghanian R, et al. (1997). *Science* 277:1078–1081.
Ellenbogen, K. A. et al. (1996). *J Am Coll Cardiol* 28:130–6.
*Enhancers and Eukaryotic Gene Expression*, Cold Spring Harbor Press, Cold Spring Harbor, N.Y. (1983).
Erickson J, et al. (1990). *Science* 249:527–533.
Fahy E, et al. (1991). *PCR Methods Appl.* 1:25–33.
Felgner P L, et al. (1987). *Proc. Natl. Acad. Sci. USA* 84:7413–7417.
Fields S and Song O-K (1989). *Nature* 340:245–246.
Fiers W, et al. (1978). *Nature* 273:113–120.
Fink D J, et al. (1992). *Hum. Gene Ther.* 3:11–19.
Fink D J, et al. (1996). *Ann. Rev. Neurosci.* 19:265–287.
Finkelstein J, et al. (1990). *Genomics* 7:167–172.
Fodor S P A (1997). *Science* 277:393–395.
Freese A, et al. (1990). *Biochem. Pharmacol.* 40:2189–2199.
Friedman T (1991). In *Therapy for Genetic Diseases*, T. Friedman, ed., Oxford University Press, pp. 105–121.
Gellens M, et al. (1992). *Proc. Natl. Acad. Sci. USA* 89:554–558.
George A L, et al. (1995). *Cytogenet. Cell. Genet.* 68:67–70.
Glover D (1985). *DNA Cloning*, I and II (Oxford Press).
Goding (1986). *Monoclonal Antibodies: Principles and Practice*, 2d ed. (Academic Press, N.Y.).
Godowski P J, et al. (1988). *Science* 241:812–816.
Goldstein S A N and Miller C (1991). *Neuron* 7:403–408.
Gordon J W, et al. (1980). *Proc. Natl. Acad. Sci. USA* 77:7380–7384.
Gozglia M and Kapikian A Z (1992). *J. Virol.* 66:4407–4412.
Graham F L and van der Eb A J (1973). *Virology* 52:456–467.
Green E D and Olson M V (1990). *Proc. Natl. Acad. Sci. USA* 87:1213–1217.
Grompe M (1993). *Nature Genetics* 5:111–117.
Grompe M, et al. (1989). *Proc. Natl. Acad. Sci. USA* 86:5855–5892.
Guthrie G and Fink G R (1991). *Guide to Yeast Genetics and Molecular Biology* (Academic Press).
Gyapay G, et al. (1994). *Nat. Genet.* 7:246–339.
Hacia J G, et al. (1996). *Nature Genetics* 14:441–447.
Harlow E and Lane D (1988). *Antibodies: A Laboratory Manual* (Cold Spring Harbor Laboratory, Cold Spring Harbor, N.Y.).

Hasty P K, et al. (1991). *Nature* 350:243.
Hausdorff S F, et al. (1991). *Biochem.* 30:3341–3346.
Heginbotham L, et al. (1994). *Biophys. J.* 66:1061–1067.
Helseth E, et al. (1990). *J. Virol.* 64:2416–2420.
Ho, W. K. et al. (1998). *J Physiol (Lond)* 507:631–8.
Hodgson J (1991). *Bio/Technology* 9:19–21.
Hohnloser, S. H., and Woosley, R. L. (1994). *Sotalol N Engl J Med* 331:31–8.
Howarth, F. C. et al. (1996). *Pflugers Arch* 431:713–22.
Huse W D, et al. (1989). *Science* 246:1275–1281.
Innis M A, et al. (1990). *PCR Protocols: A Guide to Methods and Applications* (Academic Press, San Diego, Calif.).
Jablonski E, et al. (1986). *Nucl. Acids Res.* 14:6115–6128.
Jakoby W B and Pastan I H (eds.) (1979). *Cell Culture, Methods in Enzymology* Vol. 58 (Academic Press, Inc., Harcourt Brace Jovanovich (N.Y.)).
January C T and Riddle J M (1989). *Circ. Res.* 6:977–990.
Jervell A and Lange-Nielsen F (1957). *Am. Heart J.* 54:59–68.
Jiang C, et al. (1994). *Nat. Genet.* 8:141–147.
Johnson P A, et al. (1992). *J. Virol.* 66:2952–2965.
Johnson, et al. (1993). "Peptide Turn Mimetics" in *Biotechnology and Pharmacy*, Pezzuto et al., eds., Chapman and Hall, New York.
Kaczmarek, L. K., and Blumenthal, E. M. (1997). *Physiol Rev* 77:627–41.
Kaneda Y, et al. (1989). *J. Biol. Chem.* 264:12126–12129.
Kanehisa M (1984). *Nucl. Acids Res.* 12:203–213.
Kannel W B, et al. (1987). *Am. Heart J.* 113:799–804.
Katapadi, K, et al. (1997). *Angiology* 48:821–6.
Keating M T, et al. (1991a). *Science* 252:704–706.
Keating M T, et al. (1991b). *Am. J. Hum. Genet.* 49:1335–1339.
Keating, M. T., and Sanguinetti, M. C. (1996). *Curr Opin Genet Dev* 6:326–33.
Kinszler K W, et al. (1991). *Science* 251:1366–1370.
Kohler G and Milstein C (1975). *Nature* 256:495–497.
Kraemer F B, et al. (1993). *J. Lipid Res.* 34:663–672.
Kubo T, et al. (1988). *FEBS Lett.* 241:119.
Kundu, S., et al. (1997). *Ann Emerg Med* 30:542–4.
Kwiatkowski T J, et al. (1990). *Nucl. Acids Res.* 18:7191–7192.
Kyte J and Doolittle R F (1982). *J. Mol. Biol.* 157:105–132.
Landegren U, et al. (1988). *Science* 242:229–237.
Lathrop, G M, et al. (1985). *Am. J. Hum. Genet.* 37:482–498.
Lee J E, et al. (1995). *Science* 268:836–844.
Lee, K. L. et al. (1998). *Am J Med* 104:395–6.
Lees-Miller, J. P. et al. (1997). *Circ Res* 81:719–26.
Lesage F, et al. (1993). *Receptors and Channels* 1:143–152.
Li G-R, et al. (1996). *Circ. Res.* 78:689–696.
Lim C S, et al. (1991). *Circulalion* 83:2007–2011.
Linder, M. W. et al. (1997). *Clin. Chem.* 43:254–266.
Lipshutz R I, et al. (1995). *BioTechniques* 19:442–447.
Liu D W and Antzelevitch C (1995). *Circ. Res.* 76:351–365.
Liu, S, et al. (1996). *Biophys J* 70,2704–15.
Lockhart D J, et al. (1996). *Nature Biotechnology* 14:1675–1680.
London, B. et al. (1997). *Circ Res* 81:870–8.
MacKinnon R (1991). *Nature* 350:232–235.
MacKinnon R, et al. (1993). *Science* 262:757–759.
Madzak C, et al. (1992). *J. Gen. Virol.* 73:1533–1536.
Magovcevic I, et al. (1992). *Genomics* 12:125–129.
Makkar, R. R. et al. (1993). *JAMA* 270:2590–7.
Maniatis T, et al. (1982). *Molecular Cloning: A Laboratory Manual* (Cold Spring Harbor Laboratory, Cold Spring Harbor, N.Y.).
Mann R and Baltimore D (1985). *J. Virol.* 54:401407.
Marchuk D, et al. (1991). *Nucl. Acids Res.* 19:1154.
Margolskee R F (1992). *Cur. Top. Microbiol. Immunol.* 158:67–95.
Martin R, et al. (1990). *BioTechniques* 9:762–768.
Matsuura H, et al. (1987). *Pflugers Arch* 410:596–603.
Matteucci M D and Caruthers M H (1981). *J. Am. Chem. Soc.* 103:3185.
Matthews J A and Kricka L J (1988). *Anal. Biochem.* 169:1.
McDonald, T. V. et al. (1997). *Nature* 388:289–92.
Merrifield B (1963). *J. Am. Chem. Soc.* 85:2149–2156.
Metzger D, et al. (1988). *Nature* 334:31–36.
Mifflin T E (1989). *Clinical Chem.* 35:1819–1825.
Miller A D (1992). *Curr. Top. Microbiol. Immunol.* 158:1–24.
Miller A D, et al. (1985). *Mol. Cell. Biol.* 5:431–437.
Miller A D, et al. (1988). *J. Virol.* 62:4337–4345.
Modrich P (1991). *Ann. Rev. Genet.* 25:229–253.
Mombaerts P, et al. (1992). *Cell* 68:869.
Moss A J and McDonald J (1971). *N. Engl. J. Med.* 285:903–904.
Moss A J, et al. (1991). *Circulation* 84:1136–1144.
Moss B (1992). *Curr. Top. Microbiol. Immunol.* 158:25–38.
Moss B (1996). *Proc. Natl. Acad. Sci. USA* 93:11341–11348.
Muzyczka N (1992). *Curr. Top. Microbiol. Immunol.* 158:97–129.
Nabel E G, et al. (1990). *Science* 249:1285–1288.
Nabel (1992). *Hum. Gene Ther.* 3:399–410.
Naldini L, et al. (1996). *Science* 272:263–267.
Newton C R, et al. (1989). *Nucl. Acids Res.* 17:2503–2516.
Neyroud N, et al. (1997). *Nat. Genet.* 15:186–189.
Nguyen Q, et al. (1992). *BioTechniques* 13:116–123.
Novack D F, et al. (1986). *Proc. Natl. Acad. Sci. USA* 83:586–590.
Ochman H, et al. (1988). *Genetics* 120:621–623.
Ohi S, et al. (1990). *Gene* 89:279–282.
Orita M, et al. (1989). *Proc. Natl. Acad. Sci. USA* 86:2766–2770.
Page K A, et al. (1990). *J. Virol.* 64:5270–5276.
Pellicer A, et al. (1980). *Science* 209:1414–1422.
Petropoulos C J, et al. (1992). *J. Virol.* 66:3391–3397.
Philpott K L, et al. (1992). *Science* 256:1448.
Pongs O, et al. (1988). *EMBO J.* 7:1087–1095.
Quantin B, et al. (1992). *Proc. Natl. Acad. Sci. USA* 8:2581–2584.
*Remington's Pharmaceutical Science*, 18th Ed. (1990, Mack Publishing Co., Easton, Pa.).
Rettig J, et al. (1994). *Nature* 369:289–294.
Rigby P W J, et al. (1977). *J. Mol. Biol.* 113:237–251.
Roden, D. M. (1998). *Pace-Pacing and Clinical Electrophysiology* 21:1029–1034.
Roden, D. M. et al. (1986). *Am Heart J* 111:1088–93.
Romano C (1965). Lancet 1658–659.
Romano C, et al. (1963). *Clin Pediatr.* 45:656–683.
Rosenfeld M A, et al. (1992). *Cell* 68:143–155.
Ruano G and Kidd K K (1989). *Nucl. Acids Res.* 17:8392.
Russell M W, et al. (1995). *Am. J. Hum. Genet.* 57:503–507.
Russell D and Hirata R (1998). *Nature Genetics* 18:323–328.
Sambrook J, et al. (1989). *Molecular Cloning: A Laboratory Manual*, 2nd Ed. (Cold Spring Harbor Laboratory, Cold Spring Harbor, N.Y.).
Sanguinetti M C and Jurkiewicz N K (1990). *J. Gen. Physiol.* 96:195–215.
Sanguinetti, M. C., and Jurkiewicz, N. K. (1992). *Pflugers Archiv* 420:180–6.

Sanguinetti M C, et al. (1995). *Cell* 81:299–307.
Sanguinetti M C, et al. (1996a). *Proc. Natl. Acad. Sci. USA* 93:2208–2212.
Sanguinetti M C, et al. (1996b). *Nature* 384:80–83.
Scamps, F., and Carmeliet, E. (1989). *Am J Physiol* 257:C1086–92.
Scharf S J, et al. (1986). *Science* 233:1076–1078.
Schneider G, et al. (1998). *Nature Genetics* 18:180–183.
Schott J, et al. (1995). *Am. J. Hum. Genet.* 57:1114–1122.
Schultze-Bahr E, et al. (1997). *Nat. Genet.* 17:267–268.
Schwartz P J, et al. (1975). *Am. Heart J.* 109:378–390.
Schwartz P J, et al. (1994). "The long QT syndrome." In *Cardiac Electrophysiology: from cell to bedside*, D. P. Zipes and J. Jalife eds. (W.B. Sanders Company) pp. 788–811.
Scopes R (1982). *Protein Purification: Principles and Practice*, (Springer-Verlag, N.Y.).
Seino S, et al. (1992). *Genomics* 13:1375–1377.
Sesti, F., and Goldstein, S. A. N. (1998). *J. Gen. Phys.* 112:651–64.
Sheffield V C, et al. (1989). *Proc. Natl. Acad. Sci. USA* 86:232–236.
Sheffield V C, et al. (1991). *Am. J. Hum. Genet.* 49:699–706.
Shenk T E, et al. (1975). *Proc. Natl. Acad. Sci. USA* 72:989–993.
Shi G, et al. (1996). *Neuron* 16:843–852.
Shibasaki, T. (1987). *J Physiol* 387:227–250.
Shimada T, et al. (1991). *J. Clin. Invest.* 88:1043–1047.
Shinkai Y, et al. (1992). *Cell* 68:855.
Shoemaker D D, et al. (1996). *Nature Genetics* 14:450–456.
Smith P L, et al. (1996). *Nature* 379:833–836.
Snouwaert J N, et al. (1992). *Science* 257:1083.
Snyders, D. J., and Chaudhary, A. (1996). *Mol Pharmacol* 49:949–55.
Sorge J, et al. (1984). *Mol. Cell. Biol.* 4:1730–1737.
Spargo C A, et al. (1996). *Mol. Cell. Probes* 10:247–256.
Spector, P. S. et al. (1996). *Circ Res* 78:499–503.
Spector P S, et al. (1996). *J. Gen. Physiol.* 107:611–619.
Splawski I, et al. (1997a). *N. Engl. J. Med.* 336:1562–1567.
Splawski I, et al. (1997b). *Nat. Genet.* 17:338–340.
Splawski, I. et al. (1998). *Genomics* 51:86–97.
Stemberg N (1990). *Proc. Natl. Acad. Sci. USA* 87:103–107.
Stewart M J, et al. (1992). *Hum. Gene Ther.* 3:267–275.
Stratford-Perricaudet L D, et al. (1990). *Hum. Gene Ther.* 1:241–256.
Surawicz B (1989). *J. Am. Coll. Cardiol.* 14:172–184.
Swanson R, et al. (1993). *Seminars in the Neurosciences* 5:117–124.
Tai, K.-K. et al. (1997). *J. Biol. Chem.* 272:1654–1658.
Tai, K. K., and Goldstein, S. A. N. (1998). *Nature* 391:605–608.
Takumi T, et al. (1988). *Science* 242:1042–1045.
Takumi T, et al. (1991). *J. Biol. Chem.* 266:22192–22198.
Tanigami A, et al. (1992). *Am. J. Hum. Genet.* 50:56–64.
Tokino T, et al. (1991). *Am. J. Hum. Genet.* 48:258–268.
Tyson J, et al. (1997). *Hum. Mol. Genet.* 6:2179–2185.
Valancius V and Sithies O (1991). *Mol. Cell Biol.* 11:1402.
Veldkamp, M. W. et al. (1995). *Circulation* 92:3497–504.
Vetter D E, et al. (1996). *Neuron* 17:1251–1264.
Vincent G M, et al. (1992). *N. Engl. J. Med.* 327:846–852.
Wagner E, et al. (1991). *Proc. Natl. Acad. Sci. USA* 88:4255–4259.
Wagner E, et al. (1990). *Proc. Natl. Acad. Sci. USA* 87:3410–3414.
Walker G T, et al., (1992). *Nucl. Acids Res.* 20:1691–1696.
Wang K W and Goldstein S A (1995). *Neuron* 14:1303–1309.
Wang K W, et al. (1996). *Neuron* 16:571–577.
Wang C Y and Huang L (1989). *Biochemistry* 28:9508–9514.
Wang Q and Keating M T (1994). *BioTechniques* 17:282–284.
Wang Q, et al. (1995a). *Cell* 80:805–811.
Wang Q, et al. (1995b). *Hum. Mol. Genet.* 4:1603–1607.
Wang Q, et al. (1996). *Nat. Genet.* 12:17–23.
Wang, S. et al. (1997). *J Physiol* 502:45–60.
Wang, S. et al. (i 997). *FEBS Lett* 417:43–7.
Ward O C (1964). *J. Ir. Med. Assoc.* 54:103–106.
Warmke J E and Ganetzky B (1994). *Proc. Natl. Acad. Sci.* 91:3438–3442.
Wartell R M, et al. (1990). *Nucl. Acids Res.* 18:2699–2705.
Weinstein L S et al. (1988). *FEBS Letters* 232:333–340.
Wells J A (1991). *Methods Enymol.* 202:390411.
Wetmur J G and Davidson N (1968). *J. Mol. Biol.* 31:349–370.
White M B, et al. (1992). *Genomics* 12:301–306.
White R and Lalouel J M (1988). *Annu. Rev. Genet.* 22:259–279.
Wilkinson G W and Akrigg A (1992). *Nucleic Acids Res.* 20:2233–2239.
Willich S N, et al. (1987). *Am. J. Cardiol.* 60:801–806.
Wolff J A, et al. (1990). *Science* 247:1465–1468.
Wolff J A, et al. (1991). *BioTechniques* 11:474–485.
Wollnik, B. et al. (1997). *Hum Mol Genet* 6:1943–9.
Woosley, R. L. et al. (1993). *JAMA* 269:1532–6.
Wu D Y and Wallace R B (1989). *Genomics* 4:560–569.
Wu C H, et al. (1989). *J. Biol. Chem.* 264:16985–16987.
Wu G Y, et al. (1991). *J. Biol. Chem.* 266:14338–14342.
Wymore R S, et al. (1994). *Genomics* 20:191202.
Yang, T., and Roden, D. M. (1996). *Circulation* 93:407–11.
Yang, T. et al. (1994). *Circ Res* 75:870–8.
Yang, T. et al. (1997). *Circ Res* 80:782–9.
Yang W P, et al. (1997). *Proc. Natl. Acad. Sci. USA* 94:4017–4021.
Yang, Y., and Sigworth, F. (1998). *J. Gen. Physiol.* 112:665–678.
Zenke M, et al. (1990). *Proc. Natl. Acad. Sci. USA* 87:3655–3659.
Zhou, Z. et al. (1998). *Biophys J* 74:230–41.
Zipes D P (1987). *Am. J. Cardiol.* 59:26E–31E.
Zou, A. et al. (1997). *Am J Physiol* 272:H1309–14.

Patents and Published Patent Applications

European Patent Application Publication No. 0332435.
EPO Publication No.225,807.
Hitzeman et al., EP 73,675A.
EP 425,731A.
WO 84/03564.
WO 90/07936.
WO 92/19195.
WO 93/07282.
WO 94/25503.
WO 95/01203.
WO 95/05452.
WO 96/02286.
WO 96/02646.
WO 96/11698.
WO 96/40871.
WO 96/40959.
WO 97/02048.
WO 97/12635.
U.S. Pat. No. 3,817,837.
U.S. Pat. No. 3,850,752.
U.S. Pat. No. 3,939,350.

| U.S. Pat. No. 3,996,345. | U.S. Pat. No. 5,270,184. |
| U.S. Pat. No. 4,275,149. | U.S. Pat. No. 5,409,818. |
| U.S. Pat. No. 4,277,437. | U.S. Pat. No. 5,436,146. |
| U.S. Pat. No. 4,366,241. | U.S. Pat. No. 5,455,166. |
| U.S. Pat. No. 4,376,110. | U.S. Pat. No. 5,550,050. |
| U.S. Pat. No. 4,486,530. | U.S. Pat. No. 5,691,198. |
| U.S. Pat. No. 4,554,101. | U.S. Pat. No. 5,735,500. |
| U.S. Pat. No. 4,683,195. | U.S. Pat. No. 5,747,469. |
| U.S. Pat. No. 4,683,202. | U.S. Pat. No. 5,846,710. |
| U.S. Pat. No. 4,816,567. | U.S. Pat. No. 5,856,092. |
| U.S. Pat. No. 4,868,105. | U.S. Pat. No. 5,888,819. |
| U.S. Pat. No. 5,252,479. | U.S. Pat. No. 6,004,744. |

What is claimed is:

1. An isolated nucleic acid coding for a human MiRP1 polypeptide, said polypeptide having the amino acid sequence set forth in SEQ ID NO:2 or an isolated nucleic acid which is the full complement of said nucleic acid coding for a human MiRP1 polypeptide.

2. An in vitro cell transfected with the nucleic acid of claim 1.

3. A vector comprising the nucleic acid of claim 1.

4. An in vitro cell transfected with the vector of claim 3.

5. The nucleic acid of claim 1 which is an RNA.

6. An isolated nucleic acid coding for a mutated form of the MiRP1 polypeptide sequence set forth in SEQ ID NO:2, wherein said mutated form comprises SEQ ID NO:2 except for an amino acid change selected from the group consisting of an Ala at amino acid 8; a Glu at amino acid 9; a Thr at amino acid 54; and a Thr at amino acid 57.

7. An in vitro cell transfected with the isolated nucleic acid of claim 6.

8. A vector comprising the isolated nucleic acid of claim 6.

9. An in vitro cell transfected with the vector of claim 8.

10. An isolated nucleic acid comprising (a) a mutated form of the nucleotide sequence set forth in SEQ ID NO:1 or (b) the full complement of said mutated form, wherein said mutated form comprises nucleotides 74–442 of SEQ ID NO:1 except for a nucleotide change selected from the group consisting of: an A to a G at nucleotide 95; a C to a G at nucleotide 98; a T to a C at nucleotide 234; and a T to a C at nucleotide 243.

11. An isolated nucleic acid encoding a human MiRP1 polypeptide having (a) the nucleotide sequence set forth in SEQ ID NO:1 or (b) a nucleic acid which is the full complement to said sequence.

12. The isolated nucleic acid of claim 11 which is an RNA.

13. An isolated nucleic acid which comprises nucleotides 24 to 442 of SEQ ID NO:1.

* * * * *

SEQUENCE LISTING

<160> NUMBER OF SEQ ID NOS: 22

<210> SEQ ID NO 1
<211> LENGTH: 732
<212> TYPE: DNA
<213> ORGANISM: Homo sapiens
<220> FEATURE:
<221> NAME/KEY: CDS
<222> LOCATION: (74)..(442)

<400> SEQUENCE: 1

```
caaatccaga aaagatccgt tttcctaacc ttgttcgcct attttattat ttaaattgca      60
gcaggaggga agc atg tct act tta tcc aat ttc aca cag acg ctg gaa      109
            Met Ser Thr Leu Ser Asn Phe Thr Gln Thr Leu Glu
              1               5                  10 gac gtc ttc cga agg att ttt att act tat atg gac aat tgg cgc cag      157
Asp Val Phe Arg Arg Ile Phe Ile Thr Tyr Met Asp Asn Trp Arg Gln
         15                  20                  25 aac aca aca gct gag caa gag gcc ctc caa gcc aaa gtt gat gct gag      205
Asn Thr Thr Ala Glu Gln Glu Ala Leu Gln Ala Lys Val Asp Ala Glu
     30                  35                  40 aac ttc tac tat gtc atc ctg tac ctc atg gtg atg att gga atg ttc      253
Asn Phe Tyr Tyr Val Ile Leu Tyr Leu Met Val Met Ile Gly Met Phe
 45                  50                  55                  60 tct ttc atc atc gtg gcc atc ctg gtg agc act gtg aaa tcc aag aga      301
Ser Phe Ile Ile Val Ala Ile Leu Val Ser Thr Val Lys Ser Lys Arg
                     65                  70                  75 cgg gaa cac tcc aat gac ccc tac cac cag tac att gta gag gac tgg      349
Arg Glu His Ser Asn Asp Pro Tyr His Gln Tyr Ile Val Glu Asp Trp
                 80                  85                  90 cag gaa aag tac aag agc caa atc ttg aat cta gaa gaa tcg aag gcc      397
Gln Glu Lys Tyr Lys Ser Gln Ile Leu Asn Leu Glu Glu Ser Lys Ala
             95                 100                 105 acc atc cat gag aac att ggt gcg gct ggg ttc aaa atg tcc ccc         442
Thr Ile His Glu Asn Ile Gly Ala Ala Gly Phe Lys Met Ser Pro
        110                 115                 120 tgataaggga gaaaggcacc aagctaacat ctgacgtcca gacatgaaga gatgccagtg     502
ccacgaggca aatccaaatt gtctttgctt agaagaaagt gagttccttg ctctttgttg     562
agaattttca tggagattat gtggttggcc aataaagata gatgacattt caatctcagt     622
gatttatgct tgcttgttgg agcaatattt tgtgctgaag acctctttta ctttccgggc     682
aagtgaatgt cattttaatc aatatcaatg atgaaaataa agccaaattt               732
```

<210> SEQ ID NO 2
<211> LENGTH: 123
<212> TYPE: PRT

<213> ORGANISM: Homo sapiens

<400> SEQUENCE: 2

```
Met Ser Thr Leu Ser Asn Phe Thr Gln Thr Leu Glu Asp Val Phe Arg
 1               5                  10                  15

Arg Ile Phe Ile Thr Tyr Met Asp Asn Trp Arg Gln Asn Thr Thr Ala
                20                  25                  30

Glu Gln Glu Ala Leu Gln Ala Lys Val Asp Ala Glu Asn Phe Tyr Tyr
            35                  40                  45

Val Ile Leu Tyr Leu Met Val Met Ile Gly Met Phe Ser Phe Ile Ile
        50                  55                  60

Val Ala Ile Leu Val Ser Thr Val Lys Ser Lys Arg Arg Glu His Ser
 65                 70                  75                  80

Asn Asp Pro Tyr His Gln Tyr Ile Val Glu Asp Trp Gln Glu Lys Tyr
                85                  90                  95

Lys Ser Gln Ile Leu Asn Leu Glu Glu Ser Lys Ala Thr Ile His Glu
            100                 105                 110

Asn Ile Gly Ala Ala Gly Phe Lys Met Ser Pro
        115                 120
```

<210> SEQ ID NO 3
<211> LENGTH: 468
<212> TYPE: DNA
<213> ORGANISM: Rattus norvegicus
<220> FEATURE:
<221> NAME/KEY: CDS
<222> LOCATION: (35)..(403)

<400> SEQUENCE: 3

```
cctgtgagga atctctcatc ctcaaggggg aaac atg acc act tta gcc aac ttg      55
                                    Met Thr Thr Leu Ala Asn Leu
                                     1               5 acg cag acc ctg gag gat gcc ttc aaa aag gtt ttc att act tat atg      103
Thr Gln Thr Leu Glu Asp Ala Phe Lys Lys Val Phe Ile Thr Tyr Met
            10                  15                  20 gac agc tgg agg agg aac aca aca gcc gaa caa cag gcg ctc cag gcc      151
Asp Ser Trp Arg Arg Asn Thr Thr Ala Glu Gln Gln Ala Leu Gln Ala
    25                  30                  35 aga gtg gat gcc gag aac ttc tac tac gtc atc ctg tac ctc atg gtg      199
Arg Val Asp Ala Glu Asn Phe Tyr Tyr Val Ile Leu Tyr Leu Met Val
40                  45                  50                  55 atg atc ggc atg ttc gcc ttc atc gtg gtg gcc atc ctg gtg agc acg      247
Met Ile Gly Met Phe Ala Phe Ile Val Val Ala Ile Leu Val Ser Thr
                60                  65                  70 gtg aag tcg aag cgg cgg gag cac tcc cag gac ccg tac cac cag tac      295
Val Lys Ser Lys Arg Arg Glu His Ser Gln Asp Pro Tyr His Gln Tyr
            75                  80                  85 atc gtg gag gat tgg cag cag aag tat agg agt cag atc ttg cat ctg      343
Ile Val Glu Asp Trp Gln Gln Lys Tyr Arg Ser Gln Ile Leu His Leu
        90                  95                 100 gaa gac tcc aag gcc acc atc cat gag aac ctg ggg gcg acg ggg ttc      391
Glu Asp Ser Lys Ala Thr Ile His Glu Asn Leu Gly Ala Thr Gly Phe
   105                 110                 115 aca gtg tca ccc tgataaagaa cgagagtcca tctgcccagg aagggtgct           443
Thr Val Ser Pro
120 tctgccgcct tgaagcccca cttgc                                          468
```

<210> SEQ ID NO 4

<211> LENGTH: 123
<212> TYPE: PRT
<213> ORGANISM: Rattus norvegicus

<400> SEQUENCE: 4

```
Met Thr Thr Leu Ala Asn Leu Thr Gln Thr Leu Glu Asp Ala Phe Lys
 1               5                  10                  15

Lys Val Phe Ile Thr Tyr Met Asp Ser Trp Arg Arg Asn Thr Thr Ala
             20                  25                  30

Glu Gln Gln Ala Leu Gln Ala Arg Val Asp Ala Glu Asn Phe Tyr Tyr
         35                  40                  45

Val Ile Leu Tyr Leu Met Val Met Ile Gly Met Phe Ala Phe Ile Val
     50                  55                  60

Val Ala Ile Leu Val Ser Thr Val Lys Ser Lys Arg Arg Glu His Ser
 65                  70                  75                  80

Gln Asp Pro Tyr His Gln Tyr Ile Val Glu Asp Trp Gln Gln Lys Tyr
                 85                  90                  95

Arg Ser Gln Ile Leu His Leu Glu Asp Ser Lys Ala Thr Ile His Glu
            100                 105                 110

Asn Leu Gly Ala Thr Gly Phe Thr Val Ser Pro
            115                 120
```

<210> SEQ ID NO 5
<211> LENGTH: 492
<212> TYPE: DNA
<213> ORGANISM: Homo sapiens
<220> FEATURE:
<221> NAME/KEY: CDS
<222> LOCATION: (93)..(401)

<400> SEQUENCE: 5

```
aaagggactc cttgaaactg attgagagcc cagtggattt gccagcagtt tgagcttcta     60
ccgagtcttc ccccacctca atccctgttg ct atg gag act acc aat gga acg     113
                                    Met Glu Thr Thr Asn Gly Thr
                                     1               5 gag acc tgg tat gag agc ctg cat gcc gtg ctg aag gct cta aat gcc     161
Glu Thr Trp Tyr Glu Ser Leu His Ala Val Leu Lys Ala Leu Asn Ala
         10                  15                  20 act ctt cac agc aat ttg ctc tgc cgg cca ggg cca ggg ctg ggg cca     209
Thr Leu His Ser Asn Leu Leu Cys Arg Pro Gly Pro Gly Leu Gly Pro
     25                  30                  35 gac aac cag act gaa gag agg cgg gcc agc cta cct ggc cgt gat gac     257
Asp Asn Gln Thr Glu Glu Arg Arg Ala Ser Leu Pro Gly Arg Asp Asp
 40                  45                  50                  55 aac tcc tac atg tac att ctc ttt gtc atg ttt cta ttt gct gta act     305
Asn Ser Tyr Met Tyr Ile Leu Phe Val Met Phe Leu Phe Ala Val Thr
                 60                  65                  70 gtg ggc agc ctc atc ctg gga tac acc cgc tcc cgc aaa gtg gac aag     353
Val Gly Ser Leu Ile Leu Gly Tyr Thr Arg Ser Arg Lys Val Asp Lys
             75                  80                  85 cgt agt gac ccc tat cat gtg tat atc aag aac cgt gtg tct atg atc     401
Arg Ser Asp Pro Tyr His Val Tyr Ile Lys Asn Arg Val Ser Met Ile
         90                  95                 100 taacacgaga gggctgggac ggtggaagac caagacacct ggggattgcg tctggggcct     461
ccagaactct gctgtggact gcatcaggtc t                                   492
```

<210> SEQ ID NO 6
<211> LENGTH: 103
<212> TYPE: PRT

<213> ORGANISM: Homo sapiens

<400> SEQUENCE: 6

```
Met Glu Thr Thr Asn Gly Thr Glu Thr Trp Tyr Glu Ser Leu His Ala
 1               5                  10                  15

Val Leu Lys Ala Leu Asn Ala Thr Leu His Ser Asn Leu Leu Cys Arg
             20                  25                  30

Pro Gly Pro Gly Leu Gly Pro Asp Asn Gln Thr Glu Gly Arg Arg Ala
         35                  40                  45

Ser Leu Pro Gly Arg Asp Asp Asn Ser Tyr Met Tyr Ile Leu Phe Val
     50                  55                  60

Met Phe Leu Phe Ala Val Thr Val Gly Ser Leu Ile Leu Gly Tyr Thr
 65                  70                  75                  80

Arg Ser Arg Lys Val Asp Lys Arg Ser Asp Pro Tyr His Val Tyr Ile
                 85                  90                  95

Lys Asn Arg Val Ser Met Ile
                100
```

<210> SEQ ID NO 7
<211> LENGTH: 972
<212> TYPE: DNA
<213> ORGANISM: Mus musculus
<220> FEATURE:
<221> NAME/KEY: CDS
<222> LOCATION: (241)..(549)

<400> SEQUENCE: 7

```
atcctggaaa cttgataatc aatgactctc taggagttgg aaatccgggg actcaaggaa      60
gagaaacaaa acaccagtgt ttctgtctgt gcccatttgg aaccaagaga tgcaccttgc     120
aaggaactga ggggttgtgg gacatccacg aagagatcct caaagatgtc tcagagccag     180
cagagtctct gaactgtttg atcacattcc agctcttccc atacctcaat atctgttgct     240 atg gag act tcc aac ggg act gag acc tgg tac atg agc ctc cat gct       288
Met Glu Thr Ser Asn Gly Thr Glu Thr Trp Tyr Met Ser Leu His Ala
 1               5                  10                  15 gtg ctg aag gct ctg aac aca acc ctt cac agt cac ttg ctc tgc cgg       336
Val Leu Lys Ala Leu Asn Thr Thr Leu His Ser His Leu Leu Cys Arg
             20                  25                  30 cct ggg cca gga cca ggg cca gac aat caa act gag gat cgt cgg gct       384
Pro Gly Pro Gly Pro Gly Pro Asp Asn Gln Thr Glu Asp Arg Arg Ala
         35                  40                  45 agc ctt cct ggt cgt aat gac aac tcc tac atg tat att ctc ttt gtc       432
Ser Leu Pro Gly Arg Asn Asp Asn Ser Tyr Met Tyr Ile Leu Phe Val
     50                  55                  60 atg ttc cta ttt gcc gtc act gtg ggc agt ctc atc ctg gga tat acc       480
Met Phe Leu Phe Ala Val Thr Val Gly Ser Leu Ile Leu Gly Tyr Thr
 65                  70                  75                  80 cgt tca cgc aaa gtg gac aaa cgt agt gac ccc tat cat gtg tac atc       528
Arg Ser Arg Lys Val Asp Lys Arg Ser Asp Pro Tyr His Val Tyr Ile
                 85                  90                  95 aag aac cgt gtg tct atg atc tgatgtgagg aacctgaaga caatggaaga          579
Lys Asn Arg Val Ser Met Ile
                100 ttacaatgtc tgaggattgt cttctggtgc ctccggaact caactcaacc atatcaagcc     639 acagtgtatc tatgtaagat caacaggaaa ctggtaagag gattaggtca ttattaggac     699 cagagaagag ggactgatag gcccagtctt gtggatgaga cattttttcga gacacagatg    759 cgcattataa actcagagcc catgaacaca tatatataaa gtatgacaa ccagcaagta     819
```

-continued

```
gaagaggaag ctgtggcgaa gggaaatggg gcagaaagat gctctggata tataatcttt      879
taatgtatga tcttcaacat gagaaacctt gataaaactg agaatgctac ttaaaaaaaa      939
aaaaaaaaaa aaaaaatttt ccgcggccgc aag                                   972
```

<210> SEQ ID NO 8
<211> LENGTH: 103
<212> TYPE: PRT
<213> ORGANISM: Mus musculus

<400> SEQUENCE: 8

```
Met Glu Thr Ser Asn Gly Thr Glu Thr Trp Tyr Met Ser Leu His Ala
 1               5                  10                  15

Val Leu Lys Ala Leu Asn Thr Thr Leu His Ser His Leu Leu Cys Arg
            20                  25                  30

Pro Gly Pro Gly Pro Gly Pro Asp Asn Gln Thr Glu Asp Arg Arg Ala
        35                  40                  45

Ser Leu Pro Gly Arg Asn Asp Asn Ser Tyr Met Tyr Ile Leu Phe Val
    50                  55                  60

Met Phe Leu Phe Ala Val Thr Val Gly Ser Leu Ile Leu Gly Tyr Thr
65                  70                  75                  80

Arg Ser Arg Lys Val Asp Lys Arg Ser Asp Pro Tyr His Val Tyr Ile
                85                  90                  95

Lys Asn Arg Val Ser Met Ile
            100
```

<210> SEQ ID NO 9
<211> LENGTH: 1932
<212> TYPE: DNA
<213> ORGANISM: Homo sapiens
<220> FEATURE:
<221> NAME/KEY: CDS
<222> LOCATION: (604)..(1113)

<400> SEQUENCE: 9

```
gaaccctctt ggactggacg atttgggaat tcaaaacttg ggacaaactg tcagccttgg       60
taagtcagca aggctacact ttgctttcag aaacatttaa agagggaca ttttttgccaa     120 ttaatagatg aatttttttc ctttatttc ttcctgcttt tctttgttct aaggaaacat      180
tgttttgaat ttaaaatagt ttggttttgg aaacacaatg taaactttgt ttctgctcag     240
ttaaaatacg tttcccagtt ttaaagatac tatttactgt atgctcctgt cttacattga     300
tttttttttt aatcaaagta atactgctca ctacaaacag gacaaatgtg tacactaaaa     360 aaaaaaaaa agtccttctt acttttccca gtgaaccttc ccgggcttct ctcccgtgca      420
ctccaagccc tcatagctca ctcttgtcag ctgtttggct tatgctattt ctttcatgca     480 ctttaagct tttttggtat tgcagttcca caaacctcgt gctcccccac ctccctggcc      540
caggacctgg gggagagtct aacctgcggc ttttcccag cccctgctgt ggaggcagcc      600 tca atg ctg aaa atg gag cct ctg aac agc acg cac ccc ggc acc gcc       648
    Met Leu Lys Met Glu Pro Leu Asn Ser Thr His Pro Gly Thr Ala
     1               5                  10                  15 gcc tcc agc agc ccc ctg gag tcc cgt gcg gcc ggt ggc ggc agc ggc       696
Ala Ser Ser Ser Pro Leu Glu Ser Arg Ala Ala Gly Gly Gly Ser Gly
            20                  25                  30 aat ggc aac gag tac ttc tac att ctg gtt gtc atg tcc ttc tac ggc       744
Asn Gly Asn Glu Tyr Phe Tyr Ile Leu Val Val Met Ser Phe Tyr Gly
        35                  40                  45
```

```
att ttc ttg atc gga atc atg ctg ggc tac atg aaa tcc aag agg cgg        792
Ile Phe Leu Ile Gly Ile Met Leu Gly Tyr Met Lys Ser Lys Arg Arg
        50                  55                  60 gag aag aag tcc agc ctc ctg ctg tac aaa gac gag gag cgg ctc            840
Glu Lys Lys Ser Ser Leu Leu Leu Tyr Lys Asp Glu Glu Arg Leu
 65                  70                  75 tgg ggg gag gcc atg aag ccg ctg ccc gtg gtg tcg ggc ctg agg tcg        888
Trp Gly Glu Ala Met Lys Pro Leu Pro Val Val Ser Gly Leu Arg Ser
 80                  85                  90                  95 gtg cag gtg ccc ctg atg ctg aac atg ctg cag gag agc gtg gcg ccc        936
Val Gln Val Pro Leu Met Leu Asn Met Leu Gln Glu Ser Val Ala Pro
                100                 105                 110 gcg ctg tcc tgc acc ctc tgt tcc atg gaa ggg gac agc gtg agc tcc        984
Ala Leu Ser Cys Thr Leu Cys Ser Met Glu Gly Asp Ser Val Ser Ser
            115                 120                 125 gag tcc tcc tcc ccg gac gtg cac ctc acc att cag gag gag ggg gca        1032
Glu Ser Ser Ser Pro Asp Val His Leu Thr Ile Gln Glu Glu Gly Ala
        130                 135                 140 gac gat gag ctg gag gag acc tcg gag acg ccc ctc aac gag agc agc        1080
Asp Asp Glu Leu Glu Glu Thr Ser Glu Thr Pro Leu Asn Glu Ser Ser
145                 150                 155 gaa ggg tcc tcg gag aac atc cat cag aat tcc tagcaccccc gggacccctg     1133
Glu Gly Ser Ser Glu Asn Ile His Gln Asn Ser
160                 165                 170 ccggtggctc catcagccag caaccttaga gagggaaag acagttttca agtgtctggt       1193
ttcactttca cagtgcggct gccactttga agagacccctt ggtaaacccc tgattcgggg    1253
tggggtgggg gactaggctc agccggaacc agcaccttca aggagtccgg gaggtgcctg     1313
tggtttgcac ccaccactga aaaagccgcg aagatgcgca gcgcgtacac tgactttggg     1373
gcctgggtgt tggggttct gatcagaatt gggcgggatg atatgtttgc cattttctca      1433
ctggatgccc tggtagctc ctgcagggtc tgcctgttcc cagggctgcc gaatgcttta      1493
ggacacgctg agagactagt tgtgatttgc tattttgcct agagctttgt ccttctagat     1553
ctgattggct gtaagtatct ctactgtgta cctgtggcat ccttcacag tgggttacaa      1613 gcttcttttg gattagaggg ggattttga tgggagaaag ctggagatct gaacccagcc      1673
catttgcaca ctataagaaa aaaagtaac ttttaaacct gttaacattg gccgggtta       1733 taagagatga tcttctattt tgaccttttg tctaacttat gaccttgaac tctgacctgt     1793
gaccatgcag catcacatga tggcatgacg ttctttggat cagaagagct tccccagaat     1853
ctaacctgca ctcccgatgg tggttcagga gactcttcct gatctttcta gaagggtaa     1913 agtggggttg aacaaggcc                                                  1932
```

<210> SEQ ID NO 10
<211> LENGTH: 170
<212> TYPE: PRT
<213> ORGANISM: Homo sapiens

<400> SEQUENCE: 10

```
Met Leu Lys Met Glu Pro Leu Asn Ser Thr His Pro Gly Thr Ala Ala
 1               5                  10                  15

Ser Ser Ser Pro Leu Glu Ser Arg Ala Ala Gly Gly Ser Gly Asn
             20                  25                  30

Gly Asn Glu Tyr Phe Tyr Ile Leu Val Val Met Ser Phe Tyr Gly Ile
         35                  40                  45

Phe Leu Ile Gly Ile Met Leu Gly Tyr Met Lys Ser Lys Arg Arg Glu
     50                  55                  60
```

```
Lys Lys Ser Ser Leu Leu Leu Tyr Lys Asp Glu Arg Leu Trp
 65                  70                  75                  80

Gly Glu Ala Met Lys Pro Leu Pro Val Val Ser Gly Leu Arg Ser Val
                 85                  90                  95

Gln Val Pro Leu Met Leu Asn Met Leu Gln Glu Ser Val Ala Pro Ala
            100                 105                 110

Leu Ser Cys Thr Leu Cys Ser Met Glu Gly Asp Ser Val Ser Ser Glu
        115                 120                 125

Ser Ser Ser Pro Asp Val His Leu Thr Ile Gln Glu Glu Gly Ala Asp
    130                 135                 140

Asp Glu Leu Glu Glu Thr Ser Glu Thr Pro Leu Asn Glu Ser Ser Glu
145                 150                 155                 160

Gly Ser Ser Glu Asn Ile His Gln Asn Ser
                165                 170

<210> SEQ ID NO 11
<211> LENGTH: 2499
<212> TYPE: DNA
<213> ORGANISM: Mus musculus
<220> FEATURE:
<221> NAME/KEY: CDS
<222> LOCATION: (86)..(595)

<400> SEQUENCE: 11
aacatcctca gatttggccg tttaagagtt ccacacttgg gacaaactgt cagcttttga      60
tcccggctgt gtgagcggca attca atg ctg agg atg gag cct ctg aac agc     112
                            Met Leu Arg Met Glu Pro Leu Asn Ser
                              1               5 aca tac ccc agc gct gca gcc tcc agc agc ccc ctc gag tcc cat gtg     160
Thr Tyr Pro Ser Ala Ala Ala Ser Ser Ser Pro Leu Glu Ser His Val
 10                  15                  20                  25 cct agt aac agc agt ggt aat ggc aat gaa tac ttc tat att ttg gtc     208
Pro Ser Asn Ser Ser Gly Asn Gly Asn Glu Tyr Phe Tyr Ile Leu Val
                 30                  35                  40 gtt atg tcc ttc tat ggc gtt ttc ctg atc gga atc atg ctg ggc tac     256
Val Met Ser Phe Tyr Gly Val Phe Leu Ile Gly Ile Met Leu Gly Tyr
             45                  50                  55 atg aaa tcc aag agg cgg gag aag aag tcc agc ctt ctg ctg ttg tac     304
Met Lys Ser Lys Arg Arg Glu Lys Lys Ser Ser Leu Leu Leu Leu Tyr
         60                  65                  70 aaa gac gag gag agg ctg tgg ggg gag gct atg aag ccg cta cct atg     352
Lys Asp Glu Glu Arg Leu Trp Gly Glu Ala Met Lys Pro Leu Pro Met
 75                  80                  85 atg tcc ggc ttg agg tca ggg cag gtg ccc atg atg ctg aat atg ctg     400
Met Ser Gly Leu Arg Ser Gly Gln Val Pro Met Met Leu Asn Met Leu
 90                  95                 100                 105 cag gag agt gtg gcg ccg gca ctg tcc tgc act ctt tgc tcg atg gaa     448
Gln Glu Ser Val Ala Pro Ala Leu Ser Cys Thr Leu Cys Ser Met Glu
                110                 115                 120 ggg gac agt gtg agc tcc gag tcc tcc tct cct gat gtg cac ctt ccc     496
Gly Asp Ser Val Ser Ser Glu Ser Ser Ser Pro Asp Val His Leu Pro
            125                 130                 135 atc cag gag gag ggg gct gat gac gag ctg gag gag acc tcc gag acg     544
Ile Gln Glu Glu Gly Ala Asp Asp Glu Leu Glu Glu Thr Ser Glu Thr
        140                 145                 150 cct ctc aac gac agc agt gaa ggc tct tcc gag aac atc cac cag aat     592
Pro Leu Asn Asp Ser Ser Glu Gly Ser Ser Glu Asn Ile His Gln Asn
    155                 160                 165
```

```
tcc tagcacccac caggtgctag gaggtagctc cgtaagctac acttgacaga        645
Ser
170 gggaagacac ttgccaagtg ccgggtttcg cttttgctct gcggctgcca cattgaacag  705 actgagggca agctccaaaa tggggcaggg agagacaagg ctcagctgca gtccttgagg  765 ttcctgtggg actcatctct gaaaaagtcc cagagacata cagcatgacc attgactctg  825 gggcctgggt ggtggtgggt ctgtggtcag catctggctg gataatgtgg tgttttttca  885 ctggaggccc tgggtaactt ctgcagcatc tgtctgtgcc cagggctgac aactgcccag  945 ggcaggctga aggactcgtt tcgatttgct aattttccta gagctttgtt cttctagatc 1005 tgatgggctg taagtatctt taatgtgtgc ctgtggcatt cgattagaga cagttatata 1065 tttcacttgg aggtgggaga agctgaaga gagaacccag attgtttgca caatgcaaag  1125 ggagaaggta attcgtacac atgtctgaat tagctgggag tataagctat gacctcatct 1185 gagcttttgt ctcacctgtg agcttgaact ctacagcatt gcaggtgagc atggctttct 1245 ttgccagtca gcttcctcat aaccaagcct gcattcggga tggctgttca tggtggtcct 1305 cctgaccttc acagattggg taatggtggg gttatacaag gccaaatcat tgacagctct 1365 gctgcagctc ttttttcccag cctagttttc tgaggccaga aaggacacat gtgggcctca 1425 taatatgggg ttttgtcacg tagctggacc ctggaagggc atacttaggc gagatcgagc 1485 agagctgggg ttcaagcaat gtgcttcctg gtctgagccc tgacactcat tcactgtgag 1545 gttctgggca tgtcatcaca agattctgcc tacatgaggc tcctgaggct gtgcagcccc 1605 aggggctgg gaggacatct ttagactttg tactgtgtga taaatcctcc acagcctggt 1665 gtgaggaagt ttggagcaag tatttcccct ttggccgctt agtctggaga agatgtgtt  1725 gacttaaaga cacagttgga gactttggat atgtgtagct ggggaattcg aggctggatc 1785 atcggccttc cttactgtgg ctttcccagg atgcgactga agaagctggc agcatagttt 1845 cctctgcaga gtcgtgtgga tgggaggatg ttaacacacc caaccgaggg aaagagaaat 1905 ttaaagggag ctactcaaga gctttgcagc aggctcttgt gcccttagaa accagaagg  1965 aagcagaaaa ctccccaaag gtcaagtttg cctctagtgc aaaaccttct taattttat  2025 ttatctgaac tctccctgga ttgagacaga gcagtcacta atgtccccat gaggggttaa 2085 cactataagg agctgttttt ttcaatcagt tttgacacag agatagaaag gtaatttatg 2145 ttagaggcgg aaaggggccc tctgttcact ttaagattca gagtgtggat caactccaaa 2205 gggggccgtt taagttgaaa gaagccaagt taagtttggc ctcgtgcctg gaatcacttg 2265 aattctgaaa ctttactgcg acagacatgt gcgttgtcac attttccatt gcttaatcct 2325 ggtttggtgc aagtctgtct gcgcctgtta caaagtgatg tatatacttc cttccagtat 2385 gctgagttgt agacaattgt ctggtgtatt taatggtttg taattttcac gatattttt  2445 aatttaaata aacacatttt cgatatgaaa aaaaaaaaa aaaaaaaaa aatt         2499
```

<210> SEQ ID NO 12
<211> LENGTH: 170
<212> TYPE: PRT
<213> ORGANISM: Mus musculus

<400> SEQUENCE: 12

Met Leu Arg Met Glu Pro Leu Asn Ser Thr Tyr Pro Ser Ala Ala Ala
1               5                   10                  15

Ser Ser Ser Pro Leu Glu Ser His Val Pro Ser Asn Ser Ser Gly Asn
            20                  25                  30

```
Gly Asn Glu Tyr Phe Tyr Ile Leu Val Val Met Ser Phe Tyr Gly Val
            35                  40                  45

Phe Leu Ile Gly Ile Met Leu Gly Tyr Met Lys Ser Lys Arg Arg Glu
 50                  55                  60

Lys Lys Ser Ser Leu Leu Leu Tyr Lys Asp Glu Glu Arg Leu Trp
 65                  70                  75                  80

Gly Glu Ala Met Lys Pro Leu Pro Met Met Ser Gly Leu Arg Ser Gly
                    85                  90                  95

Gln Val Pro Met Met Leu Asn Met Leu Gln Glu Ser Val Ala Pro Ala
                   100                 105                 110

Leu Ser Cys Thr Leu Cys Ser Met Glu Gly Asp Ser Val Ser Ser Glu
               115                 120                 125

Ser Ser Ser Pro Asp Val His Leu Pro Ile Gln Glu Gly Ala Asp
    130                 135                 140

Asp Glu Leu Glu Glu Thr Ser Glu Thr Pro Leu Asn Asp Ser Ser Glu
145                 150                 155                 160

Gly Ser Ser Glu Asn Ile His Gln Asn Ser
                165                 170
```

```
<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence:PCR primer
      for mutation screening

<400> SEQUENCE: 13
ccgttttcct aaccttgttc g                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence:PCR primer
      for mutation screening

<400> SEQUENCE: 14
agcatcaact ttggcttgga g                                              21

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence:PCR primer
      for mutation screening

<400> SEQUENCE: 15
gtcttccgaa ggatttttat tac                                            23

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence:PCR primer
      for mutation screening

<400> SEQUENCE: 16
gttcccgtct cttggatttc a                                              21
```

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence:PCR primer
      for mutation screening

<400> SEQUENCE: 17
aatgttctct ttcatcatcg tg                                              22

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence:PCR primer
      for mutation screening

<400> SEQUENCE: 18
tgtctggacg tcagatgtta g                                               21

<210> SEQ ID NO 19
<211> LENGTH: 09
<212> TYPE: PRT
<213> ORGANISM: Artificial Sequence
<220> FEATURE:
<223> OTHER INFORMATION: Description of Artificial Sequence:HA residues
      for epitope mapping

<400> SEQUENCE: 19

Tyr Pro Tyr Asp Val Pro Asp Tyr Ala
  1               5

<210> SEQ ID NO 20
<211> LENGTH: 14
<212> TYPE: PRT
<213> ORGANISM: Artificial Sequence
<220> FEATURE:
<223> OTHER INFORMATION: Description of Artificial Sequence:cmyc
      residues for epitope-mapping

<400> SEQUENCE: 20

Ile Ser Met Glu Gln Lys Leu Ile Ser Glu Glu Asp Leu Asn
  1               5                  10

<210> SEQ ID NO 21
<211> LENGTH: 130
<212> TYPE: PRT
<213> ORGANISM: rattus norvgecicus

<400> SEQUENCE: 21

Met Ala Leu Ser Asn Ser Thr Thr Val Leu Pro Phe Leu Ala Ser Leu
  1               5                  10                  15

Trp Gln Glu Thr Asp Glu Pro Gly Gly Asn Met Ser Ala Asp Leu Ala
                 20                  25                  30

Arg Arg Ser Gln Leu Arg Asp Ser Lys Leu Glu Ala Leu Tyr Ile
             35                  40                  45

Leu Met Val Leu Gly Phe Phe Gly Phe Phe Thr Leu Gly Ile Met Leu
     50                  55                  60

Ser Tyr Ile Arg Ser Lys Lys Leu Glu His Ser His Asp Pro Phe Asn
 65                  70                  75                  80

Val Tyr Ile Glu Ser Asp Ala Trp Gln Glu Lys Gly Lys Ala Leu Phe

-continued

```
                    85                  90                  95
Gln Ala Arg Val Leu Glu Ser Phe Arg Ala Cys Tyr Val Ile Glu Asn
                100                 105                 110

Gln Ala Ala Val Glu Gln Pro Ala Thr His Leu Pro Glu Leu Lys Pro
            115                 120                 125

Leu Ser
    130

<210> SEQ ID NO 22
<211> LENGTH: 129
<212> TYPE: PRT
<213> ORGANISM: homo sapiens

<400> SEQUENCE: 22

Met Ile Leu Ser Asn Thr Thr Ala Val Thr Pro Phe Leu Thr Lys Leu
1               5                   10                  15

Trp Gln Glu Thr Val Gln Gln Gly Gly Asn Met Ser Gly Leu Ala Arg
                20                  25                  30

Arg Ser Pro Arg Ser Gly Asp Gly Lys Leu Glu Ala Leu Tyr Val Leu
            35                  40                  45

Met Val Leu Gly Phe Phe Gly Phe Phe Thr Leu Gly Ile Met Leu Ser
    50                  55                  60

Tyr Ile Arg Ser Lys Lys Leu Glu His Ser Asn Asp Pro Phe Asn Val
65                  70                  75                  80

Tyr Ile Glu Ser Asp Ala Trp Gln Glu Lys Asp Lys Ala Tyr Val Gln
                85                  90                  95

Ala Arg Val Leu Glu Ser Tyr Arg Ser Cys Tyr Val Val Glu Asn His
            100                 105                 110

Leu Ala Ile Glu Gln Pro Asn Thr His Leu Pro Glu Thr Lys Pro Ser
            115                 120                 125

Pro
```